US012559501B2

(12) United States Patent
Kim et al.

(10) Patent No.: US 12,559,501 B2
(45) Date of Patent: Feb. 24, 2026

(54) COMPOUND AND ORGANIC LIGHT EMITTING DEVICE COMPRISING THE SAME

(71) Applicant: LG Chem, Ltd., Seoul (KR)

(72) Inventors: Shin Sung Kim, Daejeon (KR); Jaechol Lee, Daejeon (KR); Yongwook Kim, Daejeon (KR); Young Kwang Kim, Daejeon (KR); Byeong Yun Lim, Daejeon (KR); Beomshin Cho, Daejeon (KR); Hyunju Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 855 days.

(21) Appl. No.: 17/801,887

(22) PCT Filed: Jul. 19, 2021

(86) PCT No.: PCT/KR2021/009267

§ 371 (c)(1),
(2) Date: Aug. 24, 2022

(87) PCT Pub. No.: WO2022/045583

PCT Pub. Date: Mar. 3, 2022

(65) Prior Publication Data

US 2023/0115435 A1 Apr. 13, 2023

(30) Foreign Application Priority Data

Aug. 25, 2020 (KR) ........................ 10-2020-0107117
Jul. 13, 2021 (KR) ........................ 10-2021-0091852

(51) Int. Cl.

*C07D 491/22* (2006.01)
*C09K 11/06* (2006.01)
*H10K 85/60* (2023.01)
*H10K 50/11* (2023.01)

(52) U.S. Cl.

CPC ............ *C07D 491/22* (2013.01); *C09K 11/06* (2013.01); *H10K 85/657* (2023.02); *C09K 2211/1018* (2013.01); *H10K 50/11* (2023.02)

(58) Field of Classification Search

None

See application file for complete search history.

(56) References Cited

U.S. PATENT DOCUMENTS

| | | | |
|---|---|---|---|
| 2004/0251816 | A1 | 12/2004 | Leo et al. |
| 2013/0087768 | A1 | 4/2013 | Kim et al. |
| 2015/0325798 | A1 | 11/2015 | Cho et al. |
| 2019/0189927 | A1 | 6/2019 | Lee et al. |
| 2020/0207713 | A1 | 7/2020 | Lee et al. |
| 2020/0343452 | A1 | 10/2020 | Lee et al. |

FOREIGN PATENT DOCUMENTS

| | | | | | |
|---|---|---|---|---|---|
| CN | 106220638 | A | * | 12/2016 | ......... C07D 491/048 |
| CN | 106397398 | A | * | 2/2017 | ......... H10K 85/6572 |
| CN | 106467544 | A | * | 3/2017 | ............ C07F 7/0812 |
| CN | 107652307 | A | * | 2/2018 | ................ C07F 7/10 |
| CN | 109574996 | A | | 4/2019 | |
| CN | 110903294 | A | | 3/2020 | |
| CN | 110903295 | A | | 3/2020 | |
| CN | 111377956 | A | | 7/2020 | |
| CN | 112645968 | A | * | 4/2021 | ................ C07F 5/02 |
| KR | 20000051826 | A | | 8/2000 | |
| KR | 2013-0110051 | A | | 10/2013 | |
| KR | 101380335 | B1 | | 4/2014 | |
| KR | 20150129928 | A | | 11/2015 | |
| KR | 101803143 | B1 | | 11/2017 | |
| KR | 20180013713 | A | | 2/2018 | |
| KR | 20190035135 | A | | 4/2019 | |
| KR | 20190078117 | A | | 7/2019 | |
| KR | 2022-0026478 | A | | 3/2022 | |
| WO | 2003012890 | A2 | | 2/2003 | |
| WO | 2017023126 | A1 | | 2/2017 | |
| WO | 2019-172647 | A1 | | 9/2019 | |
| WO | 2020057480 | A1 | | 3/2020 | |
| WO | 2020-149610 | A1 | | 7/2020 | |

OTHER PUBLICATIONS

Search report from International Applicaiton No. PCT/KR2021/009267, mailed Nov. 1, 2021.
Extended European Search Report for Application No. 21861882.5 dated Nov. 13, 2023. 6 pgs.

* cited by examiner

*Primary Examiner* — Robert S Loewe
(74) *Attorney, Agent, or Firm* — Lerner David LLP

(57) ABSTRACT

The present disclosure provides a novel compound of Chemical Formula 1 and an organic light emitting device including the same:

[Chemical Formula 1]

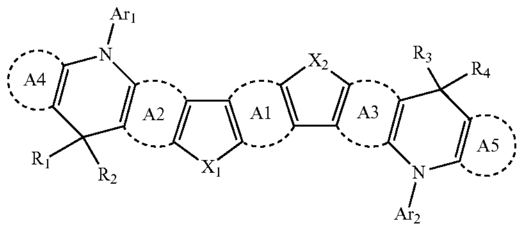

$X_1$, $X_2$, A4, A5, $Ar_1$, $Ar_2$, and $R_1$ to $R_4$ are described herein.

14 Claims, 1 Drawing Sheet

[FIG. 1]
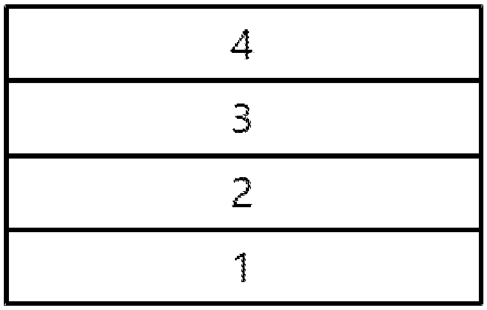
[FIG. 2]
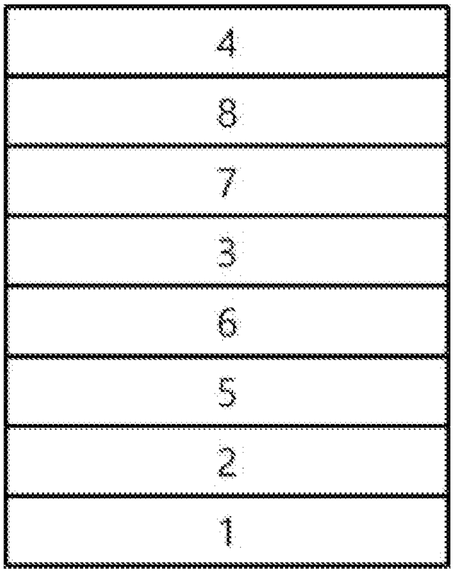

COMPOUND AND ORGANIC LIGHT EMITTING DEVICE COMPRISING THE SAME

CROSS-REFERENCE TO RELATED APPLICATION(S)

The present application is a national stage entry under 35 U.S.C. § 371 of International Application No. PCT/KR2021/009267 filed on Jul. 19, 2021, which claims priority from Korean Patent Application No. 10-2020-0107117 filed on Aug. 25, 2020 and Korean Patent Application No. 10-2021-0091852 filed on Jul. 13, 2021, all the disclosures of which are incorporated herein by reference.

TECHNICAL FIELD

The present disclosure relates to a novel compound and an organic light emitting device comprising the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

For the organic materials used in the organic light emitting devices as described above, the development of new materials is continuously required.

Meanwhile, recently, in order to reduce process costs, an organic light emitting device using a solution process, particularly an inkjet process, has been developed instead of a conventional deposition process. In the initial stage of development, attempts have been made to develop organic light emitting devices by coating all organic light emitting device layers by a solution process, but current technology has limitations. Therefore, only HIL, HTL, and EML are processed by a solution process, and a hybrid process utilizing traditional deposition processes is being studied as a subsequent process.

Therefore, the present disclosure provides a novel material for an organic light emitting device that can be used for an organic light emitting device and at the same time, can be used for a solution process.

PRIOR ART LITERATURE

Patent Literature (Patent Literature 1) Korean Unexamined Patent Publication No. 10-2000-0051826

DISCLOSURE

Technical Problem

It is an object of the present disclosure to provide a novel compound and an organic light emitting device comprising the same.

Technical Solution

According to an aspect of the present disclosure, there is provided a compound represented by the following Chemical Formula 1:

[Chemical Formula 1]

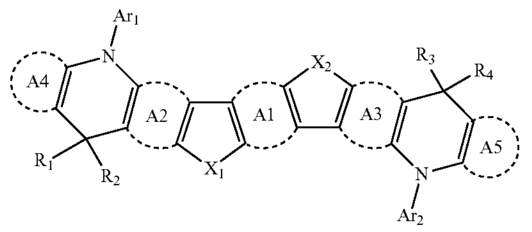

in Chemical Formula 1, $X_1$ and $X_2$ are each independently O, S, Se, or Te;

A1 to A3 are each independently a substituted or unsubstituted $C_{6-60}$ aromatic ring fused with two adjacent rings, A4 and A5 are each independently a substituted or unsubstituted $C_{6-60}$ aromatic ring fused with one adjacent ring, $Ar_1$ and $Ar_2$ are each independently a substituted or unsubstituted $C_{6-60}$ aryl; or a substituted or unsubstituted $C_{2-60}$ heteroaryl containing at least one selected from the group consisting of Si, N, O and S, and $R_1$ to $R_4$ are each independently hydrogen; deuterium; halogen; a substituted or unsubstituted $C_{1-60}$ alkyl; a substituted or unsubstituted $C_{3-60}$ cycloalkyl; a substituted or unsubstituted $C_{6-60}$ aryl; or a substituted or unsubstituted $C_{2-60}$ heteroaryl containing at least one selected from the group consisting of N, O and S.

According to another aspect of the present disclosure, there is provided an organic light emitting device comprising: a first electrode; a second electrode that is provided opposite to the first electrode; and one or more organic material layers that are provided between the first electrode and the second electrode, wherein one or more layers of the organic material layers include the compound represented by Chemical Formula 1.

Advantageous Effects

The above-mentioned compound represented by Chemical Formula 1 can be used as a material of an organic material layer of an organic light emitting device, can be used in a solution process, and can improve the efficiency, achieve low driving voltage and/or improve lifetime characteristics in the organic light emitting device. In particular, the compound represented by the Chemical Formula 1 may be used as a hole injection material, hole transport material and/or light emitting material.

DESCRIPTION OF DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 3, an electron transport layer 7, an electron injection layer 8, and a cathode 4.

BEST MODE

Hereinafter, embodiments of the present disclosure will be described in more detail to facilitate understanding of the invention.

The present disclosure provides the compound represented by Chemical Formula 1.

As used herein, the notation  and  mean a bond linked to another substituent group.

As used herein, the term "substituted or unsubstituted" means being substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; an arylsily group; and a heterocyclic group containing at least one of N, O and S atoms, or being substituted with a substituent to which two or more substituents of the above-exemplified substituents are linked, or being unsubstituted. For example, "a substituent in which two or more substituents are linked" may be a biphenyl group. Namely, a biphenyl group may be an aryl group, or it may also be interpreted as a substituent in which two phenyl groups are linked.

In the present disclosure, the carbon number of a carbonyl group is not particularly limited, but is preferably 1 to 40. Specifically, the carbonyl group may be a substituent group having the following structural formulas, but is not limited thereto.

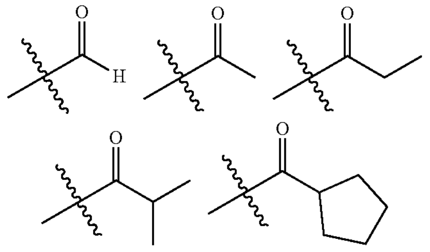

-continued

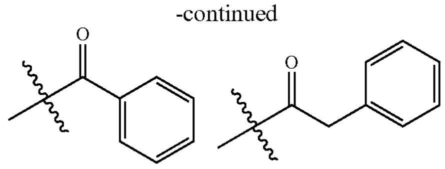

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a substituent group having the following structural formulas, but is not limited thereto.

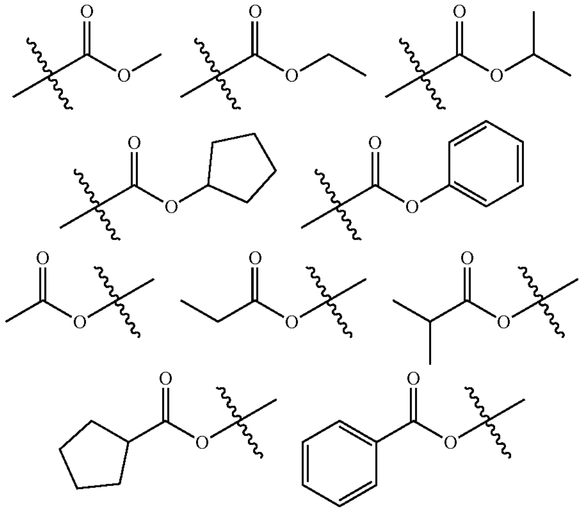

In the present disclosure, the carbon number of an imide group is not particularly limited, but is preferably 1 to 25. Specifically, the imide group may be a substituent group having the following structural formulas, but is not limited thereto.

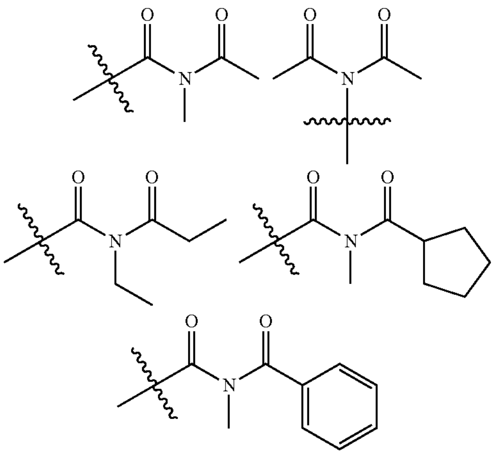

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group, or the like, but is not limited thereto.

In the present disclosure, the fluorenyl group may be substituted, and two substituents may be linked with each other to form a spiro structure. In the case where the fluorenyl group is substituted,

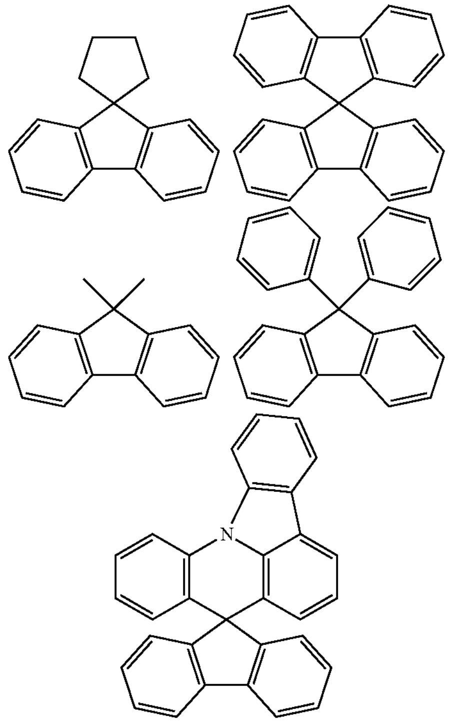

and the like can be formed. However, the structure is not limited thereto.

In the present disclosure, a heterocyclic group is a heterocyclic group containing at least one of O, N, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the above-mentioned examples of the aryl group. In the present disclosure, the alkyl group in the aralkyl group, the alkylaryl group and the alkylamine group is the same as the above-mentioned examples of the alkyl group. In the present disclosure, the heteroaryl group in the heteroarylamine may be applied to the above-mentioned description of the heterocyclic group. In the present disclosure, the alkenyl group in the aralkenyl group is the same as the above-mentioned examples of the alkenyl group. In the present disclosure, the alkenyl group in the aralkenyl group is the same as the above-mentioned examples of the alkenyl group. In the present disclosure, the above-mentioned description of the aryl group may be applied except that the arylene is a divalent group. In the present disclosure, the above-mentioned description of the heterocyclic group can be applied except that the heteroarylene is a divalent group. In the present disclosure, the above-mentioned description of the aryl group or cycloalkyl group may be applied except that the hydrocarbon ring is not a monovalent group but formed by combining two substituent groups. In the present disclosure, the above-mentioned description of the heterocyclic group may be applied, except that the heterocyclic group is not a monovalent group but formed by combining two substituent groups.

(Compound)

The present disclosure provides the compound represented by Chemical Formula 1.

Preferably, the Chemical Formula 1 may be represented by any one of the following Chemical Formulas 1-1 to 1-17:

1-1

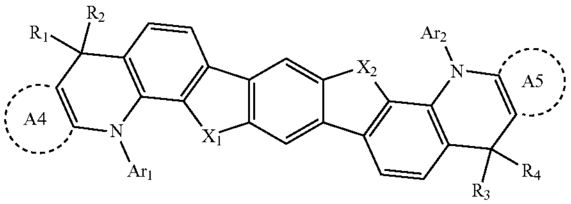

1-2

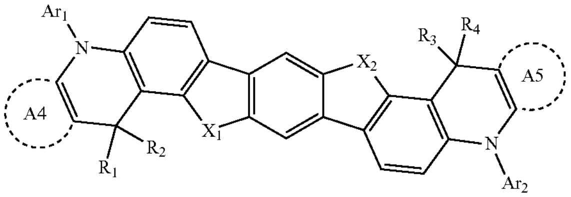

1-3

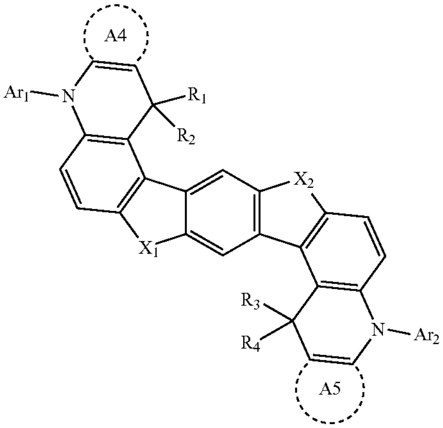

-continued 1-4

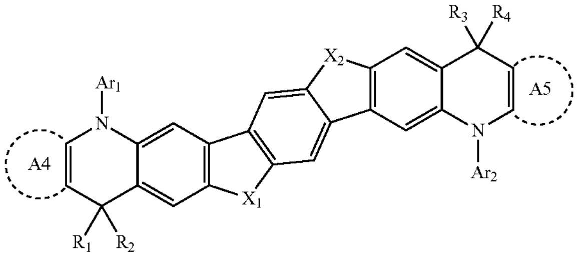

1-5

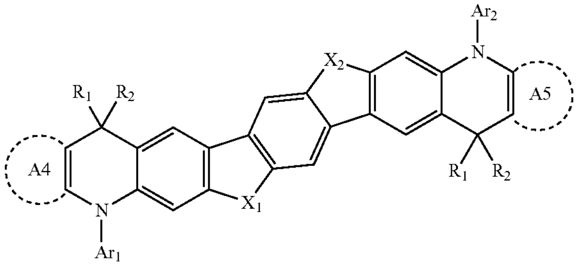

1-6

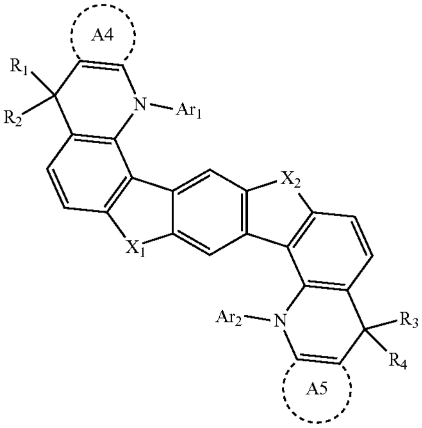

1-7

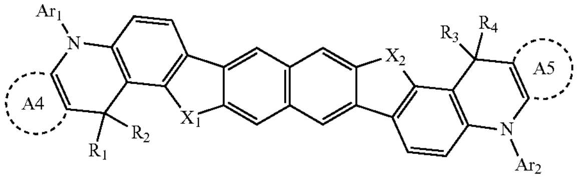

1-8

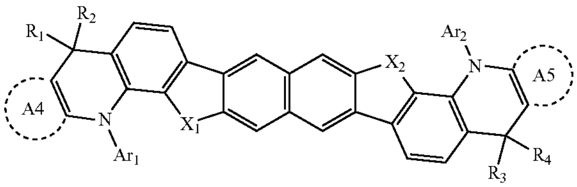

-continued
1-9
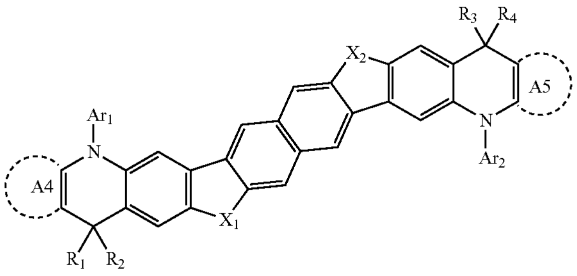
1-10
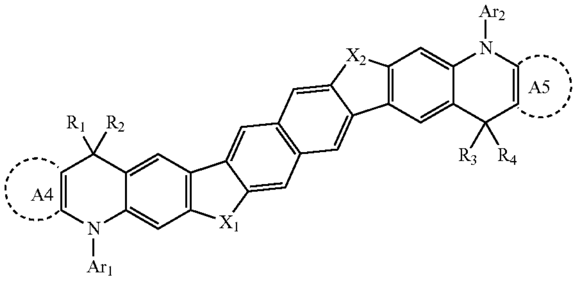
1-11
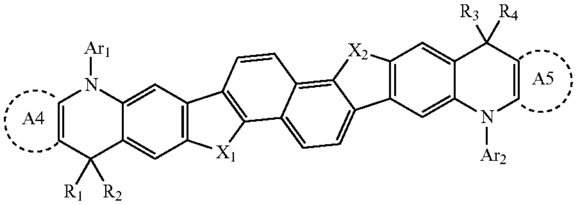
1-12
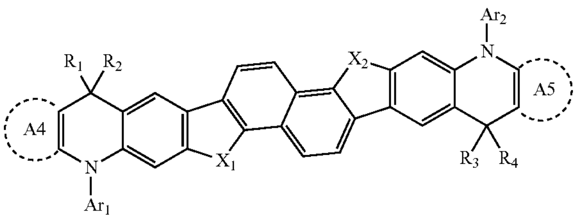
1-13
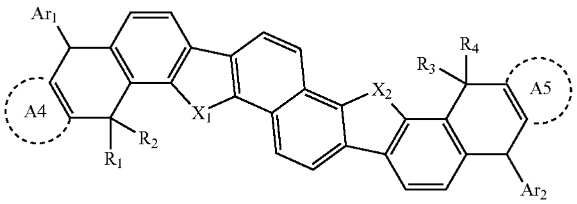
1-14
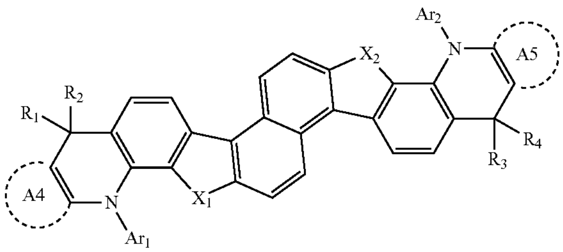
-continued
1-15
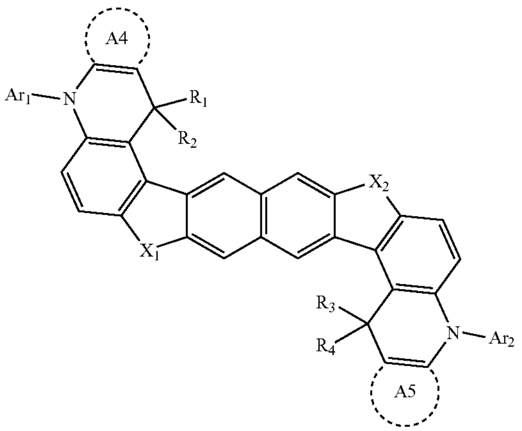
1-16
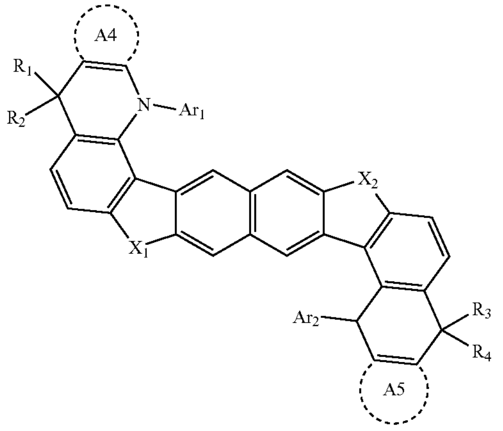
1-17
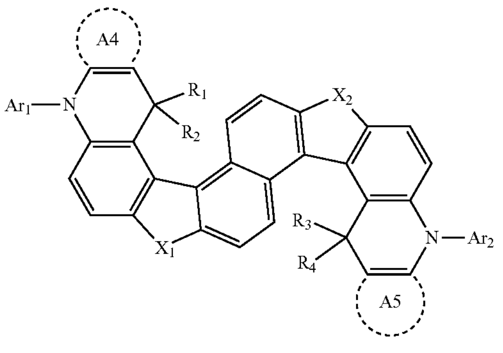
in Chemical Formula 1-1 to Chemical Formula 1-17,
$X_1$, $X_2$, A4, A5, $Ar_1$, $Ar_2$, and $R_1$ to $R_4$ are as defined in Chemical Formula 1.
Preferably, the Chemical Formula 1 may be represented by any one of the following Chemical Formulas 1-A to 1-F:

[Chemical Formula 1-A]

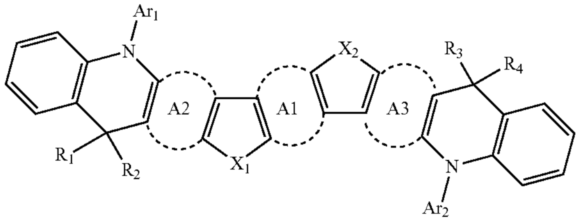

[Chemical Formula 1-B]

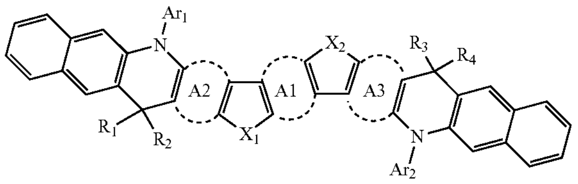

[Chemical Formula 1-C]

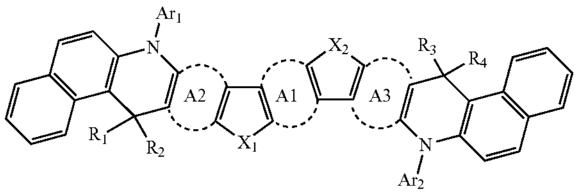

[Chemical Formula 1-D]

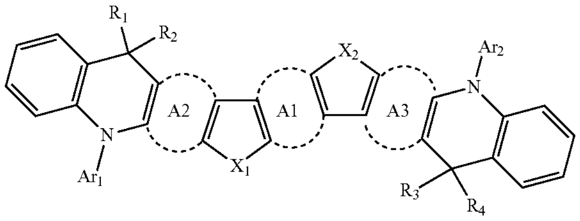

[Chemical Formula 1-E]

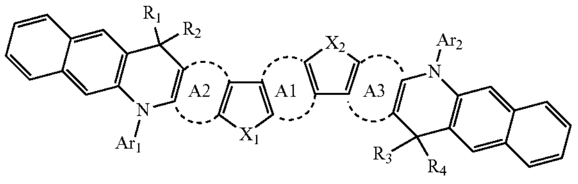

[Chemical Formula 1-F]

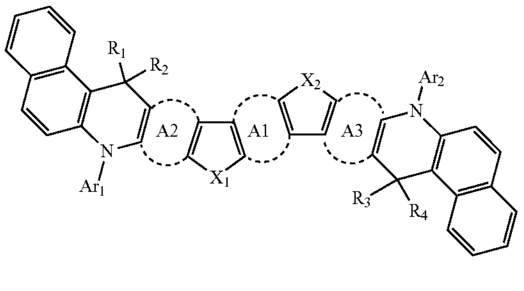

in Chemical Formula 1-A to Chemical Formula 1-F, $X_1$, $X_2$, A1 to A3, $Ar_1$, $Ar_2$, and $R_1$ to $R_4$ are as defined in Chemical Formula 1.

Further, preferably, the Chemical Formula 1 may be represented by any one of the following Chemical Formula 1-A-1, Chemical Formula 1-A-2, or Chemical Formula 1-B-1:

[Chemical Formula 1-A-1]

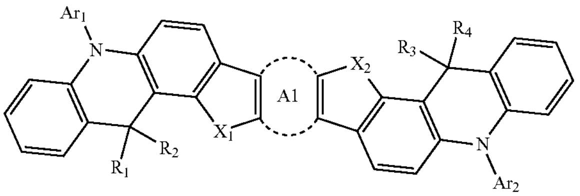

[Chemical Formula 1-A-2]

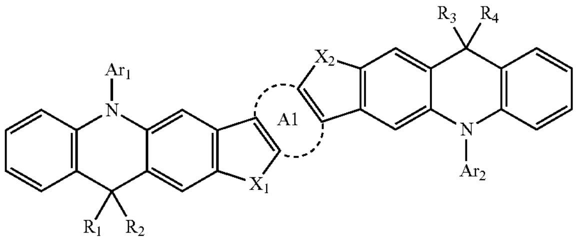

[Chemical Formula 1-B-1]

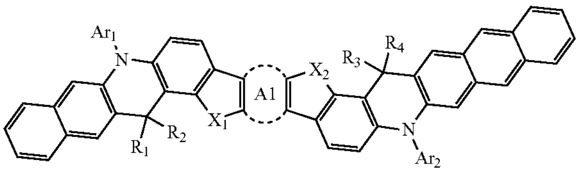

in Chemical Formula 1-A-1, Chemical Formula 1-A-2 and Chemical Formula 1-B-1,

A1 is a benzene ring or a naphthalene ring fused with two adjacent rings, and $X_1$, $X_2$, $Ar_1$, $Ar_2$ and $R_1$ to $R_4$ are as defined in Chemical Formula 1.

Preferably, $X_1$ and $X_2$ may be each independently O, S, or Se.

Preferably, $X_1$ and $X_2$ may be identical to each other.

Preferably, A1 to A3 may be each independently a substituted or unsubstituted $C_{6-20}$ aromatic ring fused with two adjacent rings, and more preferably, A1 to A3 may be each independently a benzene ring or a naphthalene ring fused with two adjacent rings.

Preferably, A4 and A5 may be each independently a substituted or unsubstituted $C_{6-20}$ aromatic ring fused with one adjacent ring, and more preferably, A4 and A5 may be each independently a benzene ring or a naphthalene ring fused with one adjacent ring.

Preferably, A2 and A3 may be identical to each other, and A4 and A5 may be identical to each other.

Preferably, $Ar_1$ and $Ar_2$ may be each independently a substituted or unsubstituted $C_{6-20}$ aryl; or a substituted or unsubstituted $C_{2-20}$ heteroaryl containing any one or more selected from the group consisting of Si, N, O and S. More preferably, $Ar_1$ and $Ar_2$ may be each independently phenyl, biphenylyl, naphthyl, dimethylfluorenyl, dimethyl dibenzosilolyl, dimethyl benzofluorenyl, benzofuranyl, benzothiophenyl, dibenzofuranyl, dibenzothiophenyl, or pyridinyl, and the $Ar_1$ and $Ar_2$ may be each independently unsubstituted; or substituted with any one or more substituent groups selected from the group consisting of butyl, tert-butyl, trimethylsilyl and triphenylsilyl. Most preferably, $Ar_1$ and $Ar_2$ may be each independently any one selected from the group consisting of:

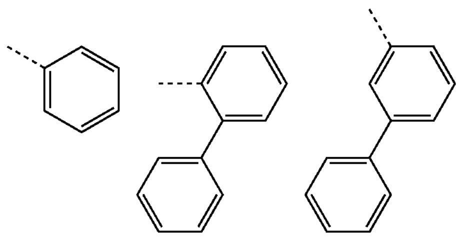
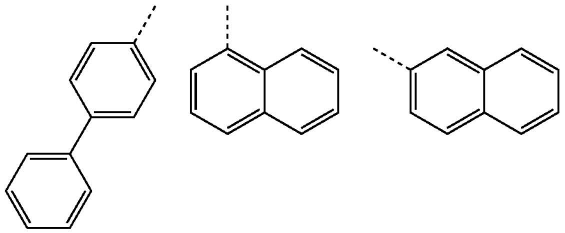
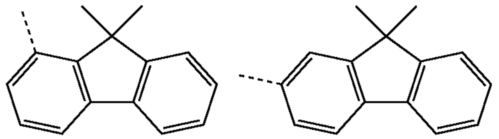
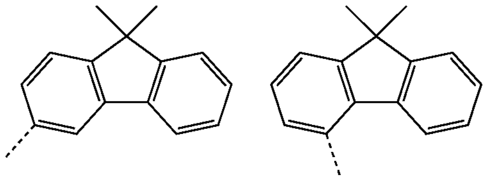
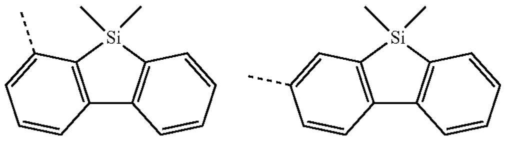
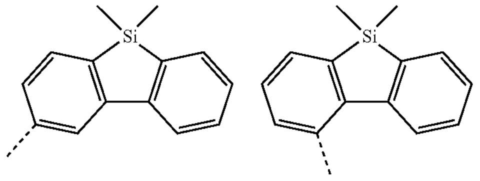
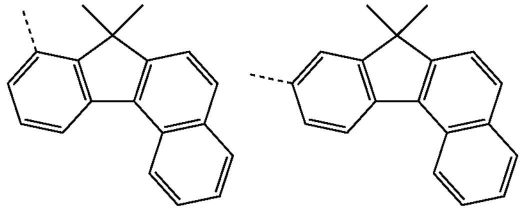
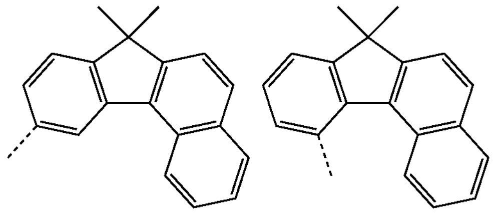
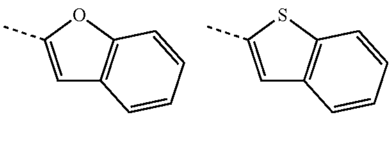

-continued

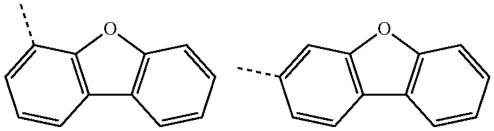
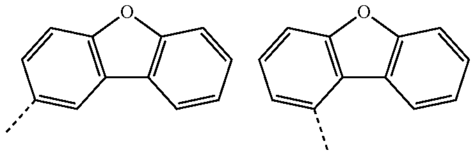
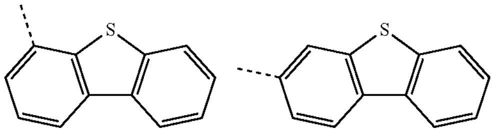
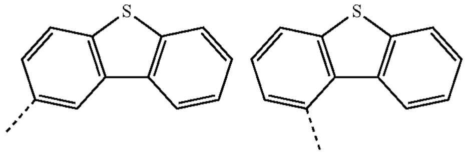
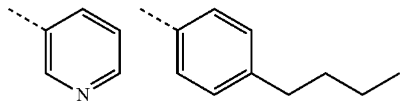
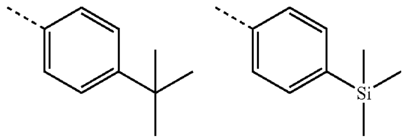
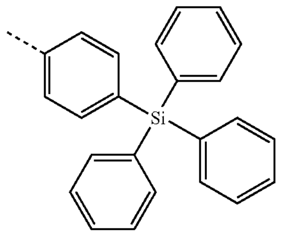

Preferably, $Ar_1$ and $Ar_2$ may be identical to each other.

Preferably, $R_1$ to $R_4$ may be each independently hydrogen; deuterium; halogen; a substituted or unsubstituted $C_{1-10}$ alkyl; a substituted or unsubstituted $C_{3-20}$ cycloalkyl; a substituted or unsubstituted $C_{6-20}$ aryl; or a substituted or unsubstituted $C_{2-20}$ heteroaryl containing any one or more selected from the group consisting of N, O and S. More preferably, $R_1$ to $R_4$ may be each independently hydrogen, deuterium, methyl, or hexyl.

Preferably, $R_1$ and $R_3$ may be identical to each other, and $R_2$ and $R_4$ may be identical to each other.

More preferably, A2 and A3 may be identical to each other, A4 and A5 may be identical to each other, $Ar_1$ and $Ar_2$ may be identical to each other, $R_1$ and $R_3$ may be identical to each other, $R_2$ and $R_4$ may be identical to each other, and most preferably, $X_1$ and $X_2$ may be identical to each other, A2 and A3 may be identical to each other, A4 and A5 may be identical to each other, $Ar_1$ and $Ar_2$ may be identical to each other, $R_1$ and R3 may be identical to each other, and $R_2$ and $R_4$ may be identical to each other.

Representative examples of the compound represented by Chemical Formula 1 are as follows:

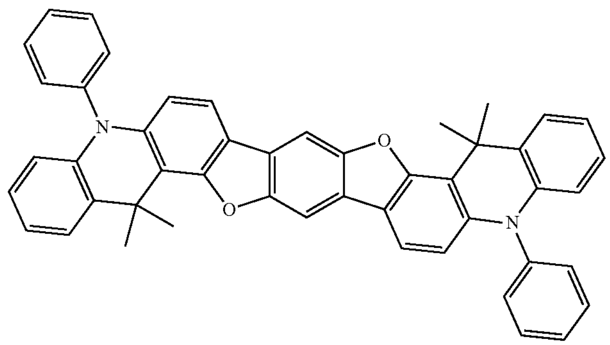
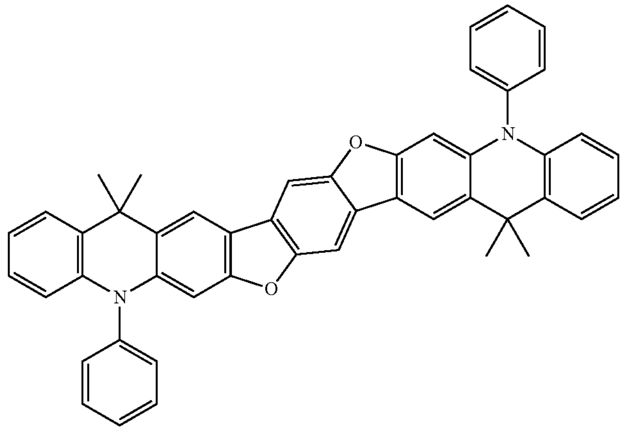
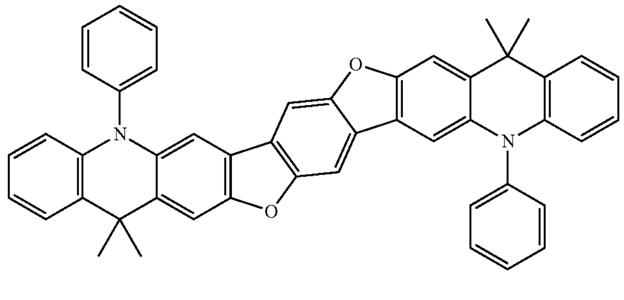
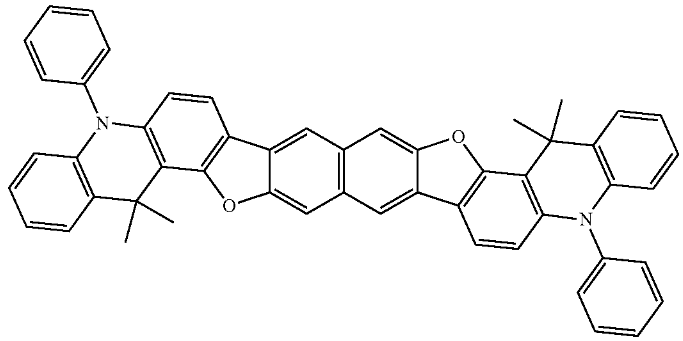

-continued
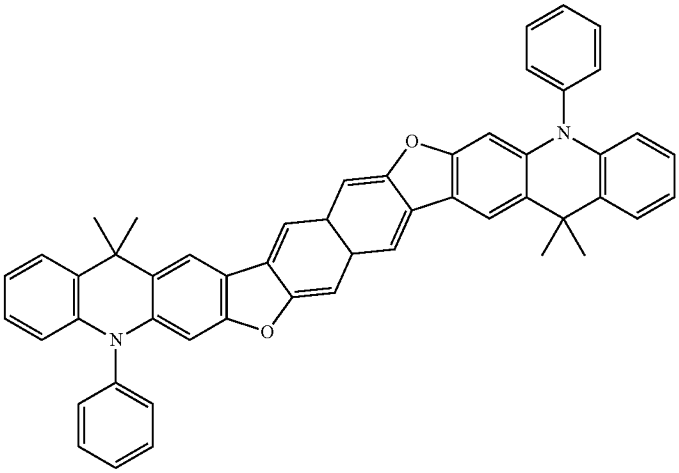
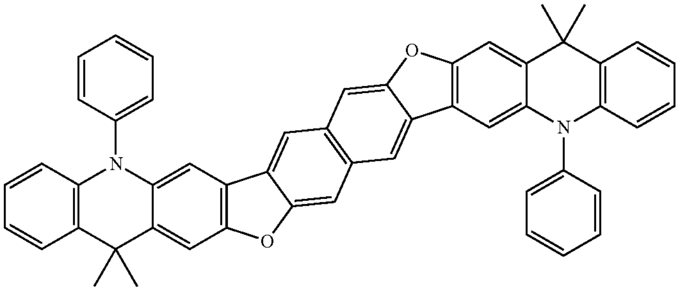
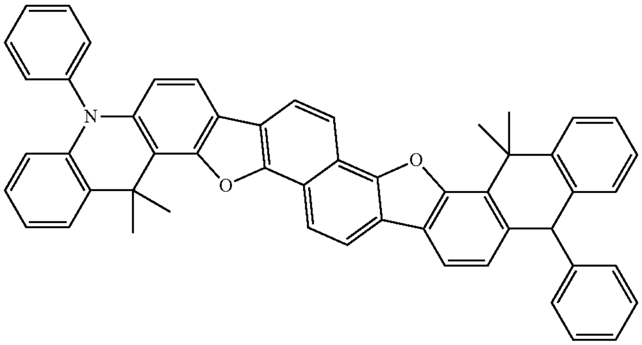
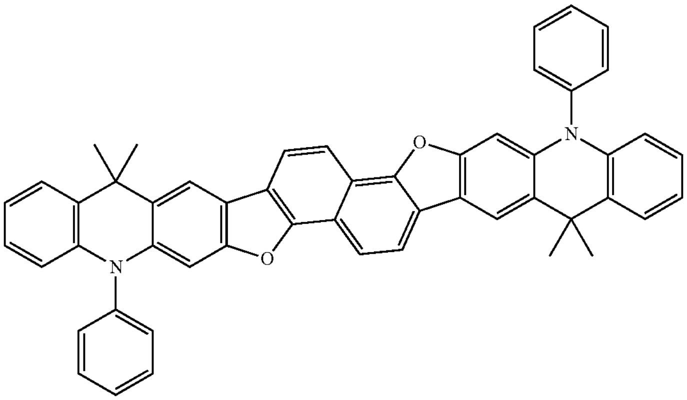

-continued
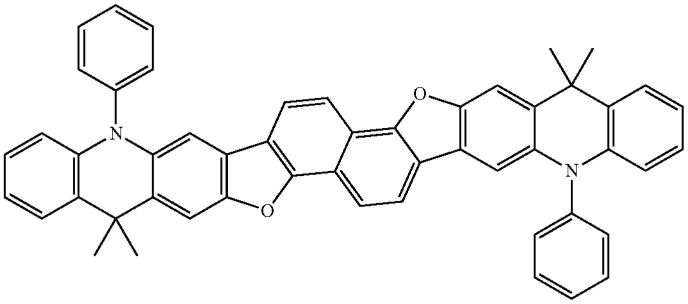
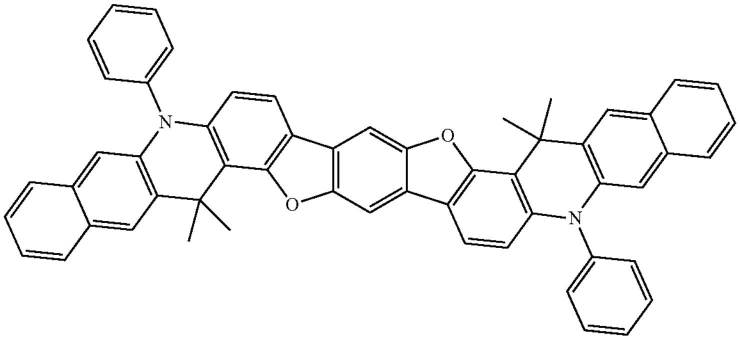
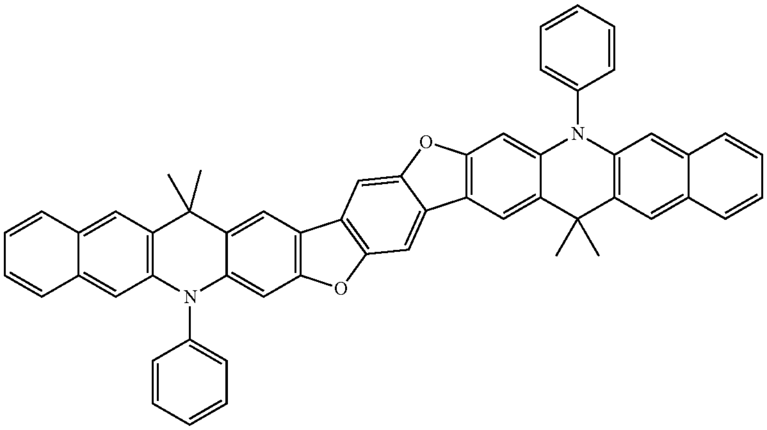
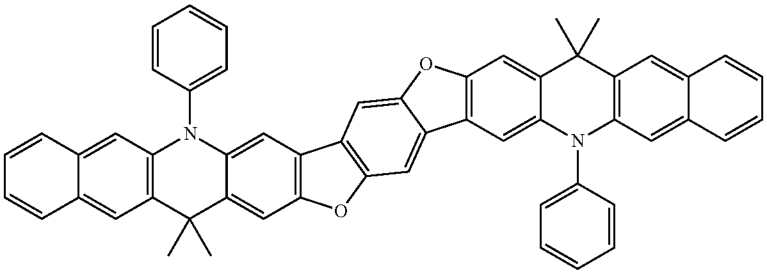
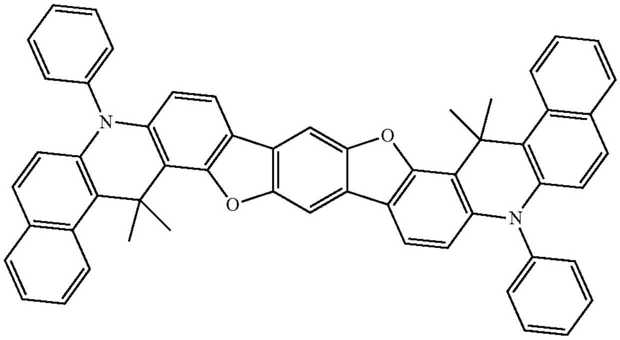

-continued
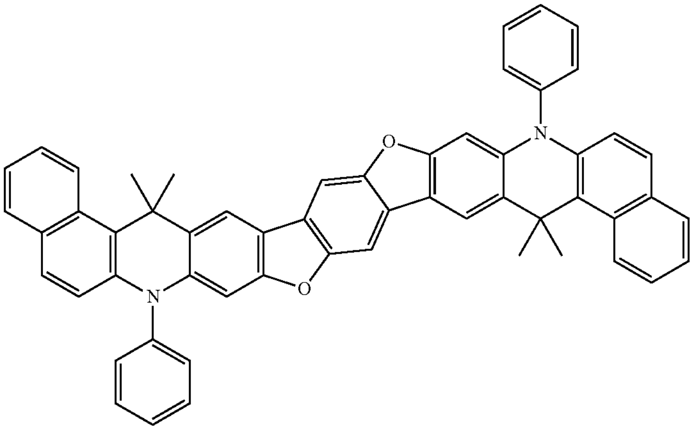
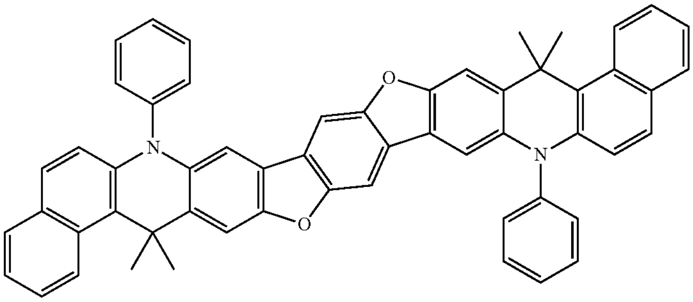
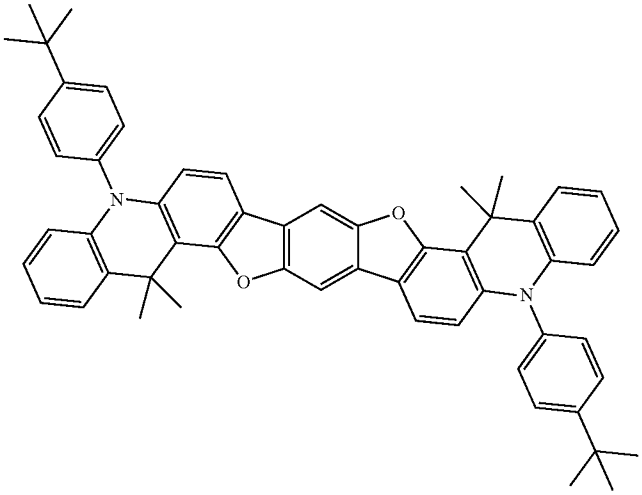
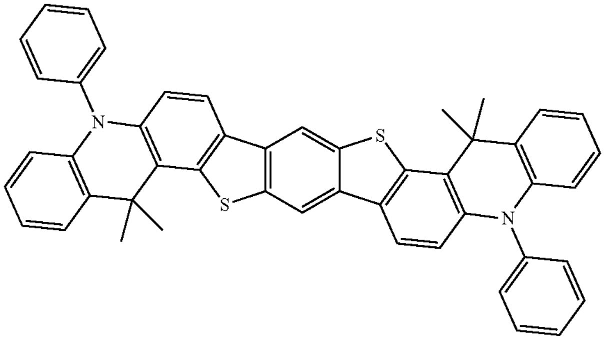

-continued
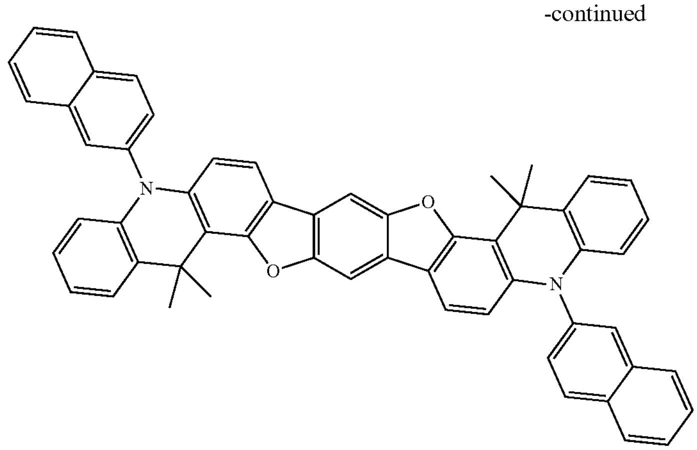
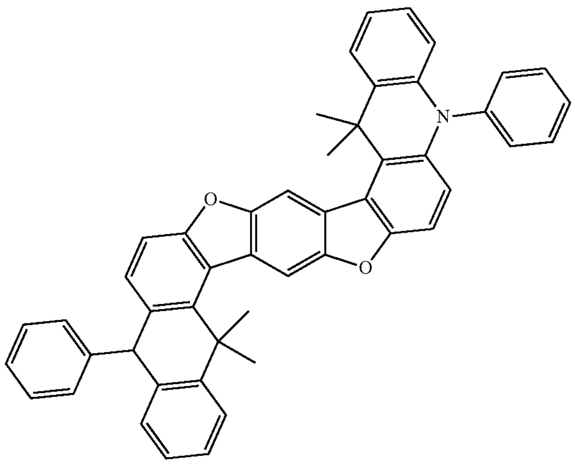
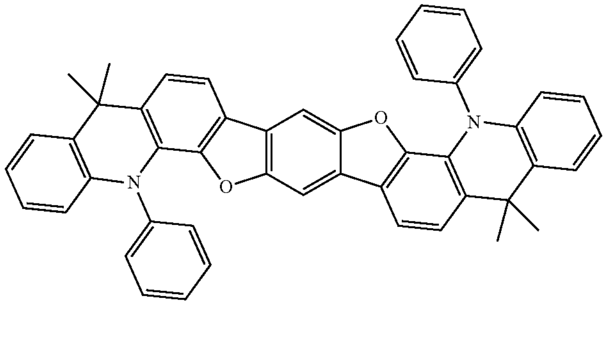
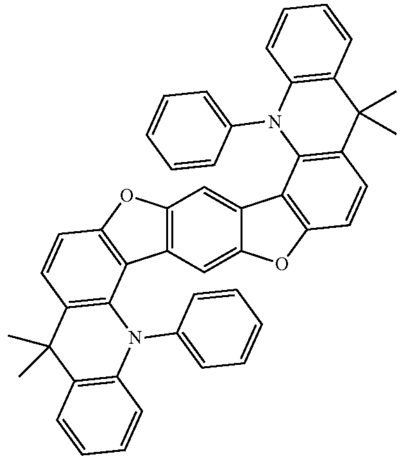

-continued
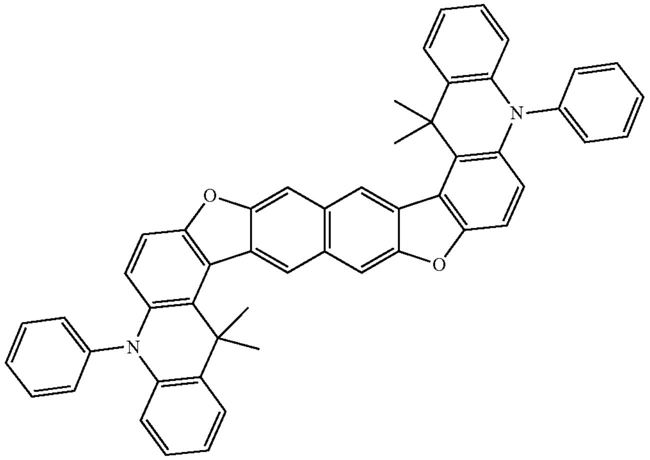
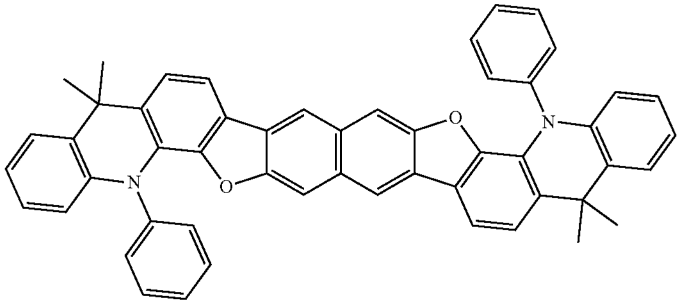
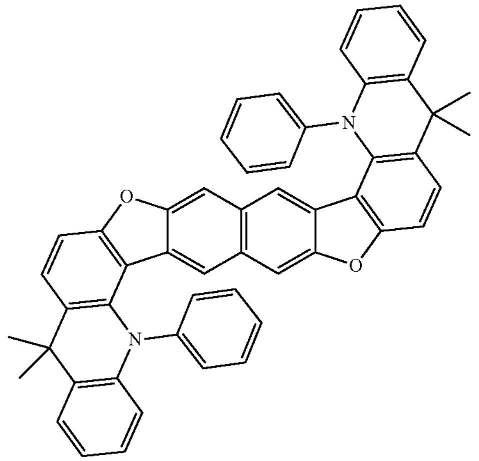
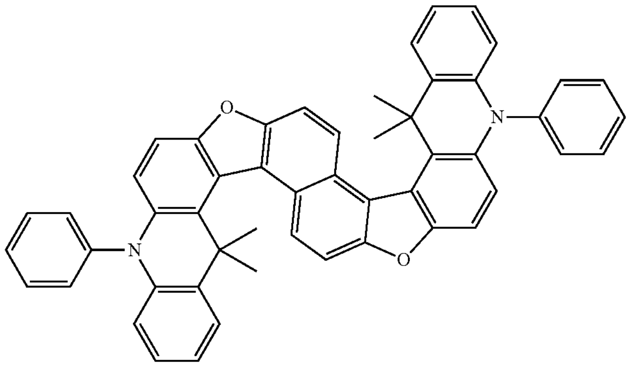

-continued
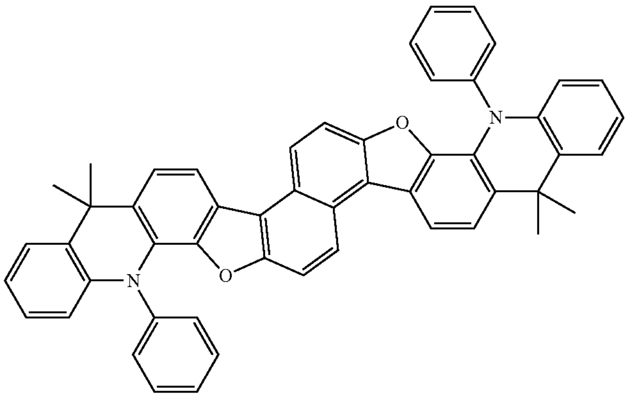
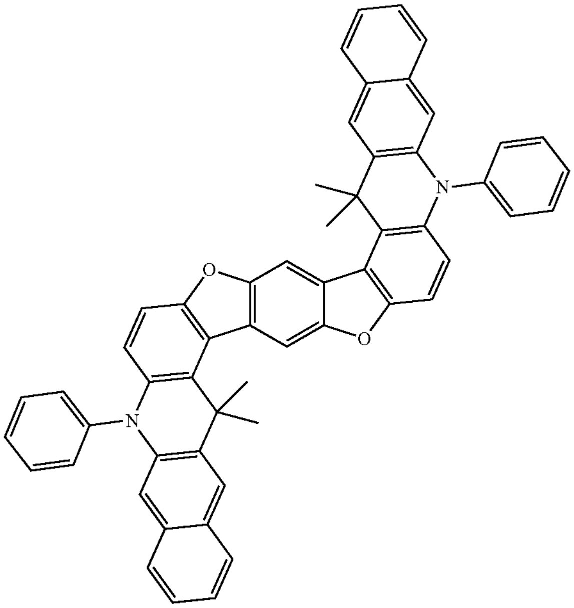
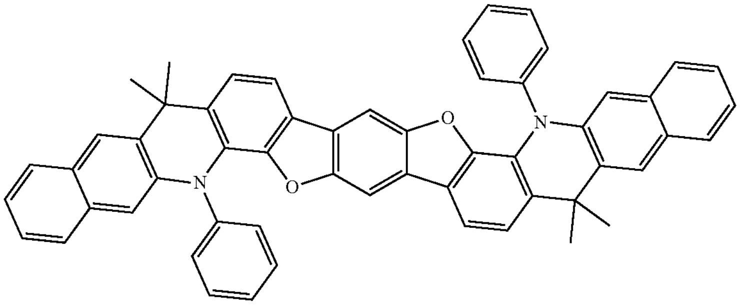

-continued
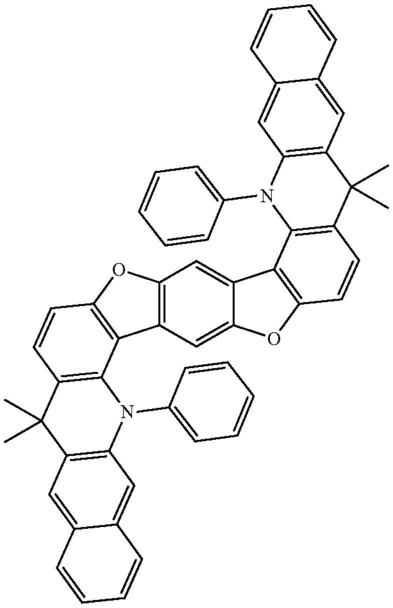
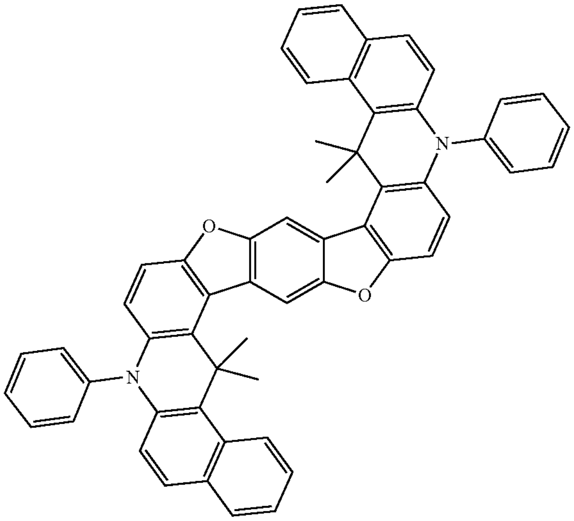
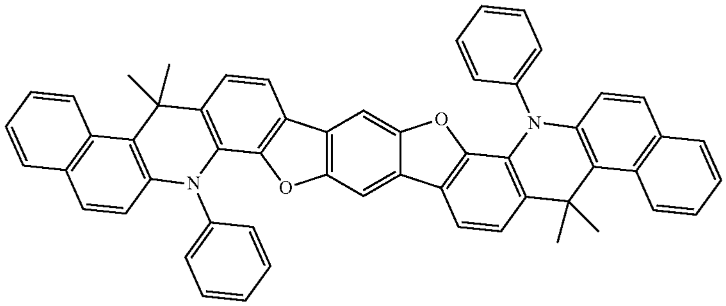
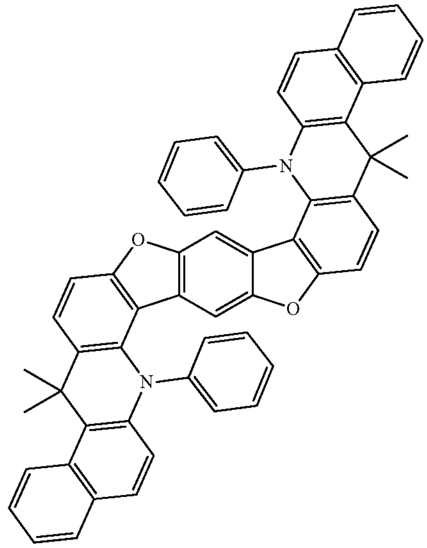
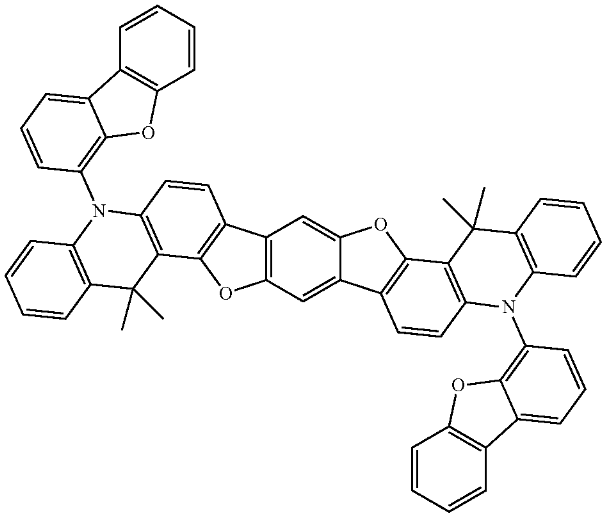

-continued
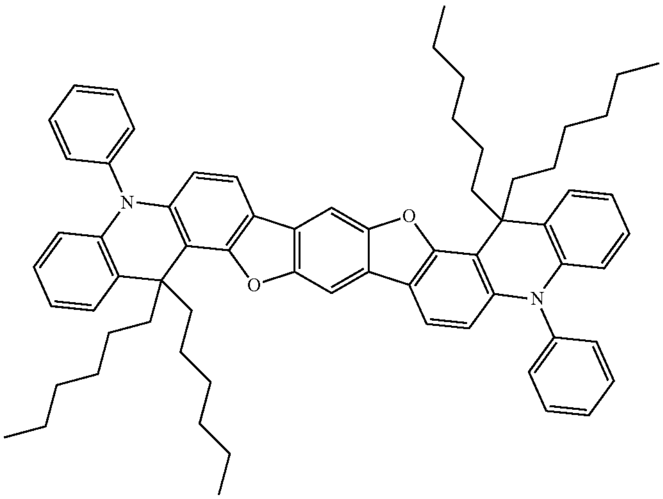
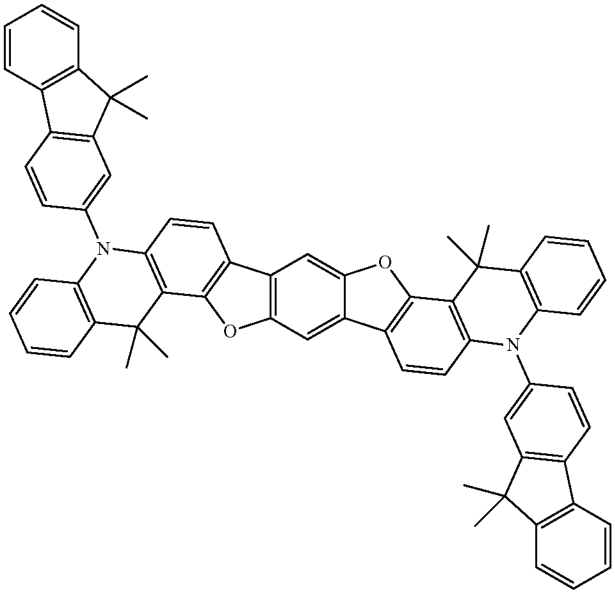
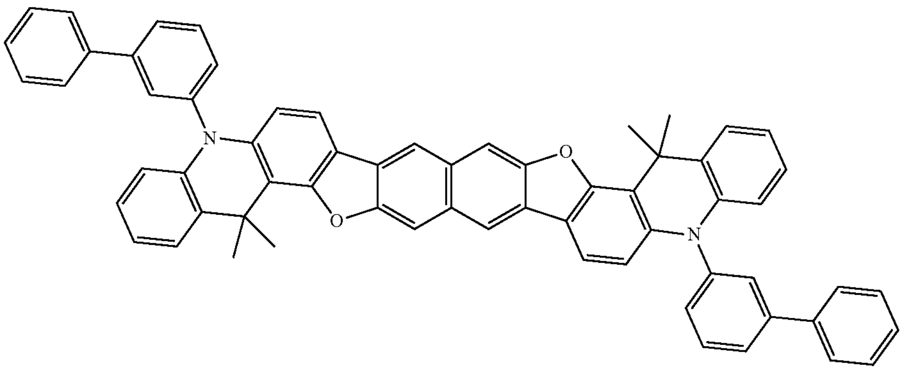

-continued
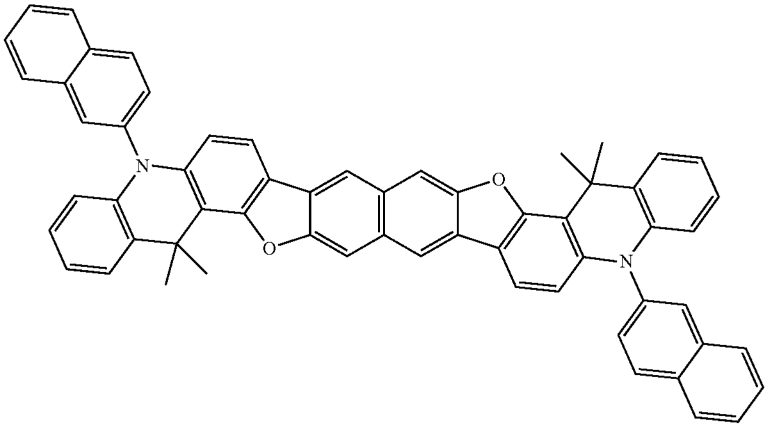
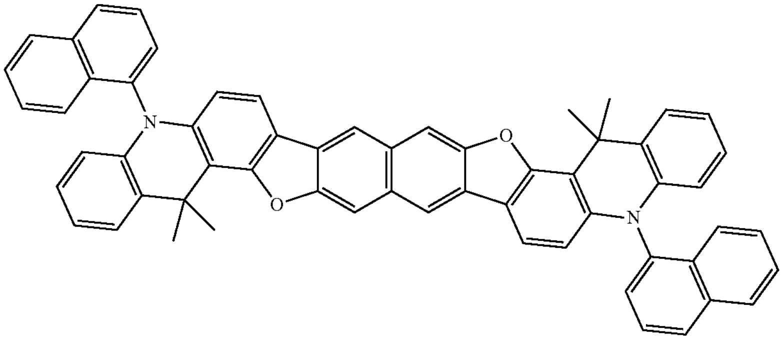
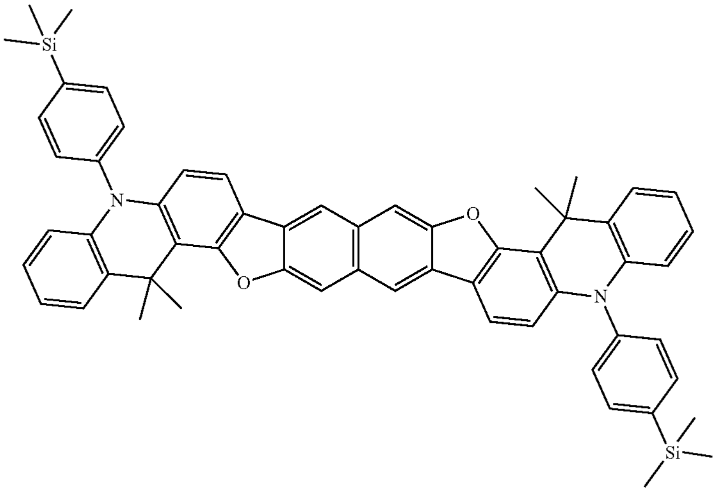

-continued
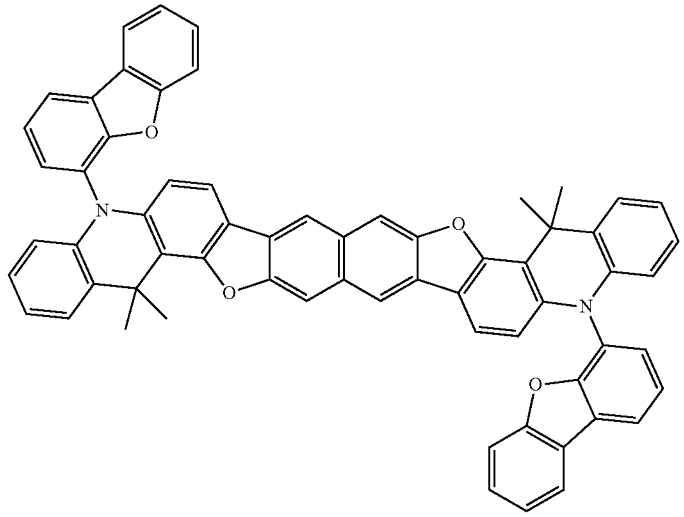
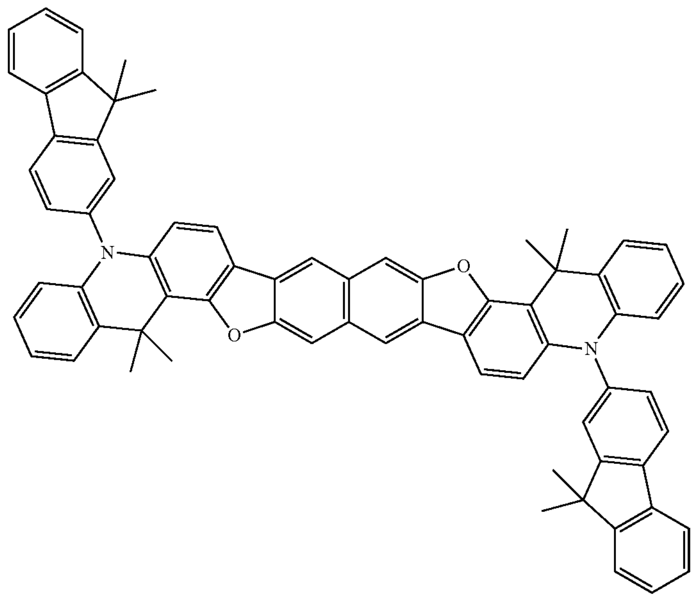
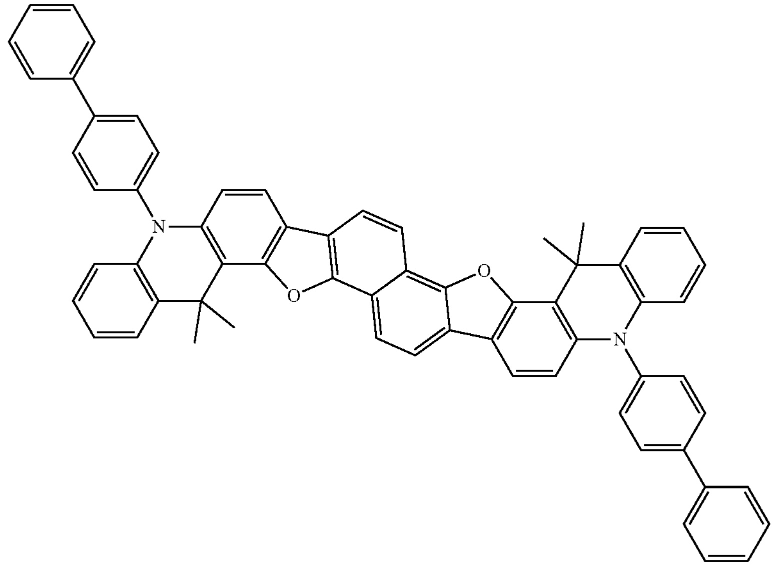

-continued
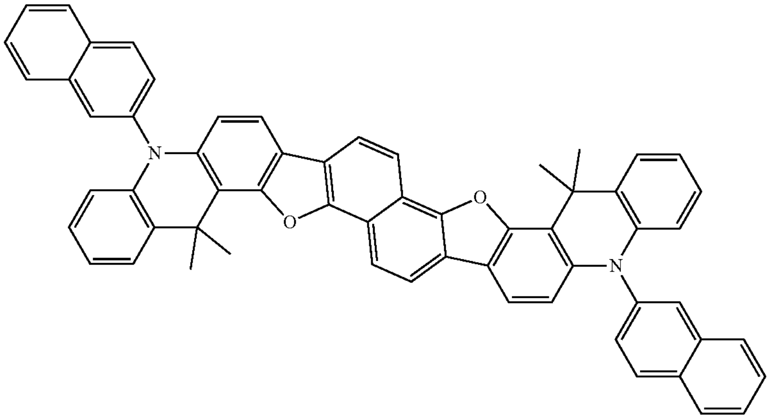
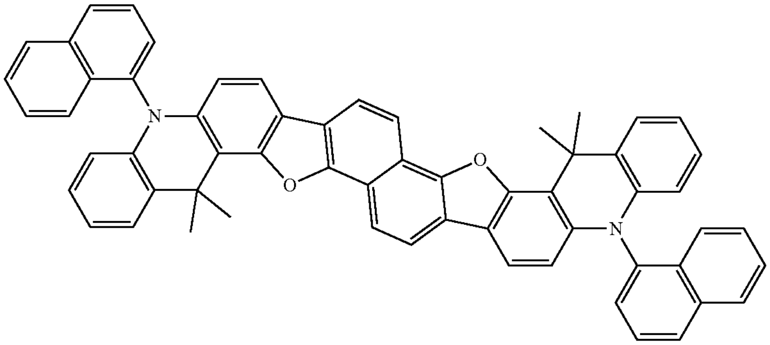
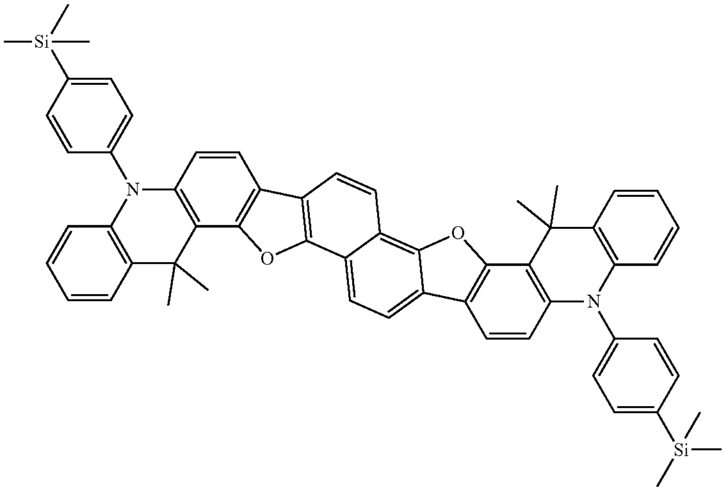

-continued
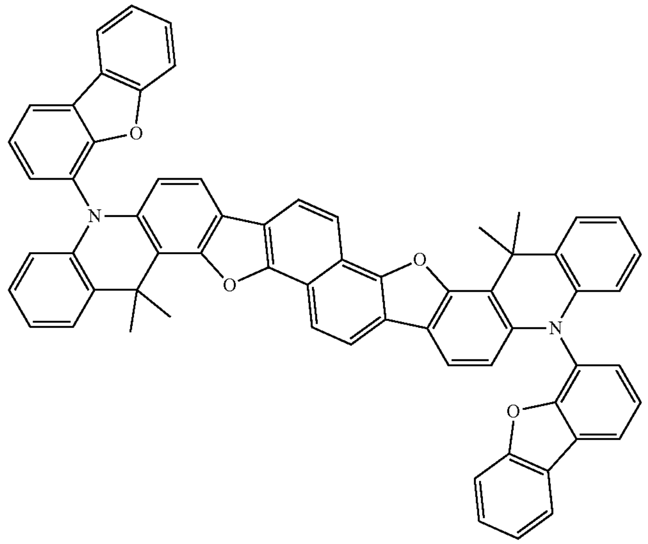
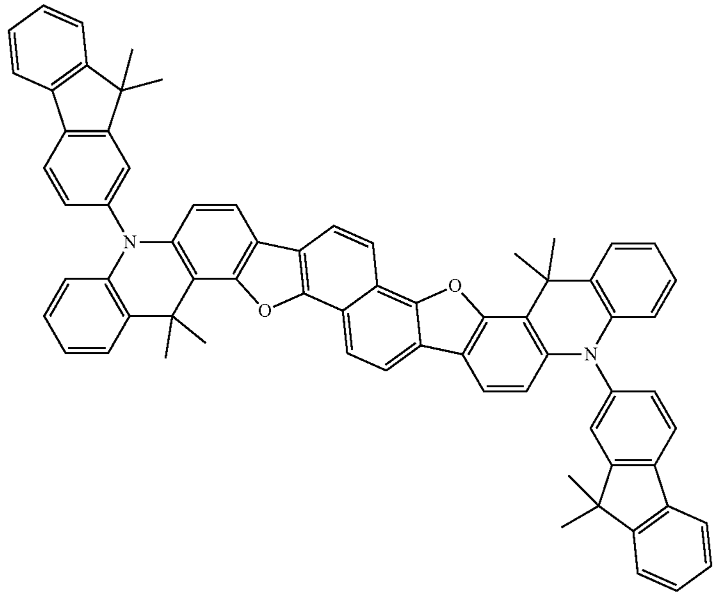
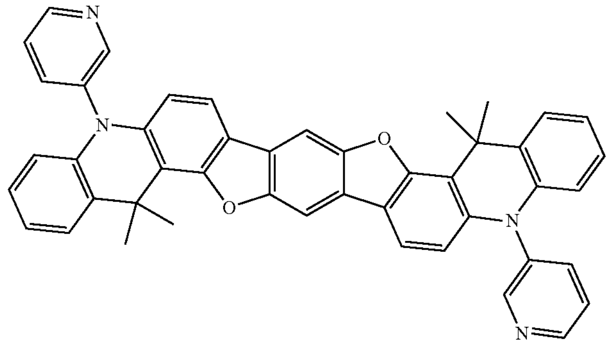 [SMILES: CC1(C)c2ccccc2N(c2cccnc2)c2ccc3c(oc4cc5c(cc43)oc3c4c(ccc35)N(c3cccnc3)c3ccccc3C4(C)C)c21]

-continued
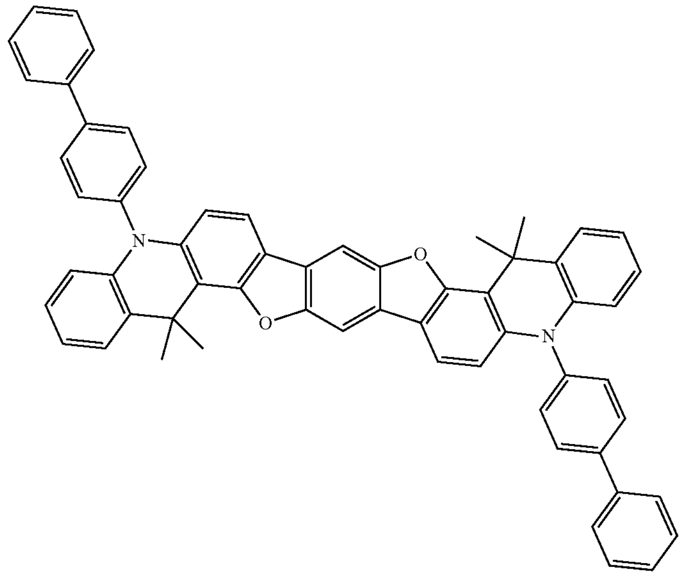
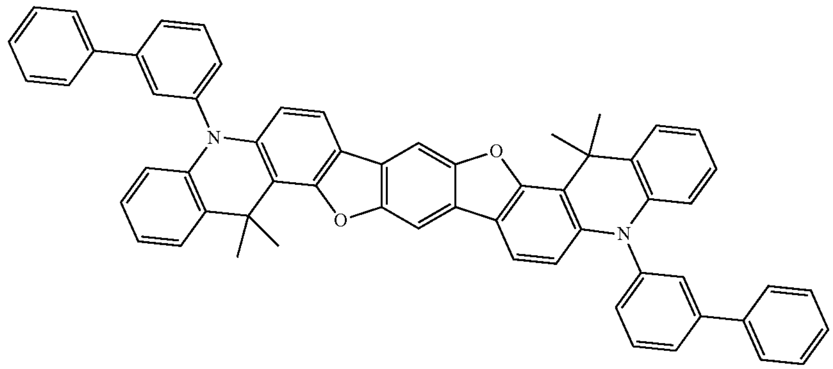
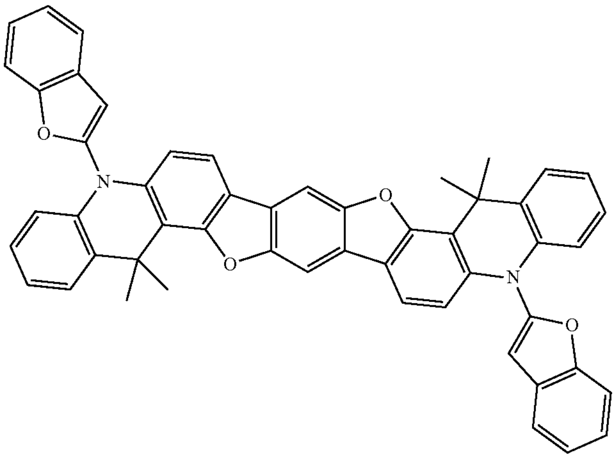

-continued
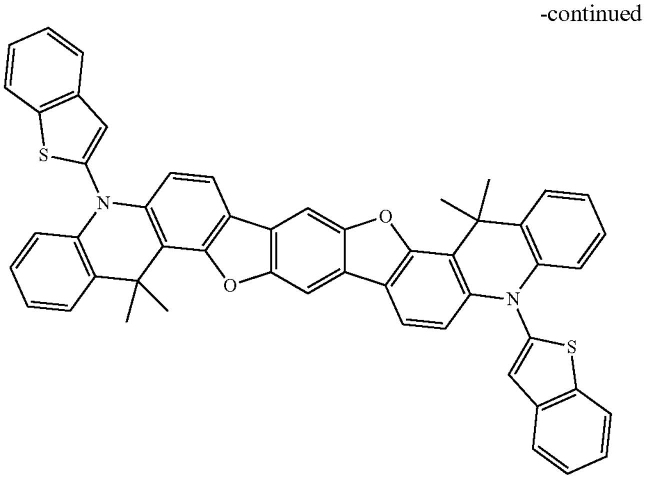
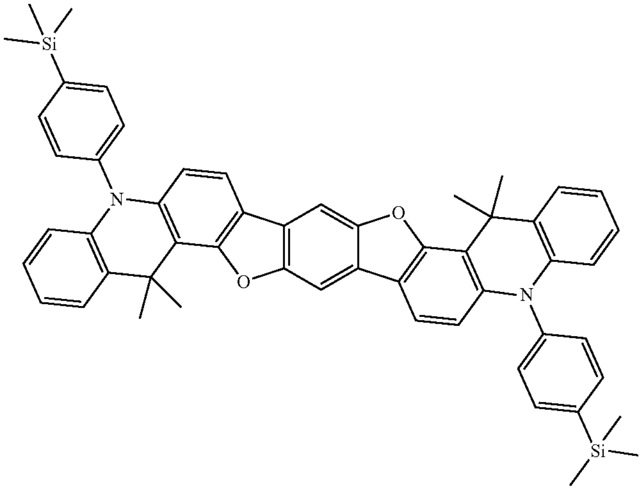
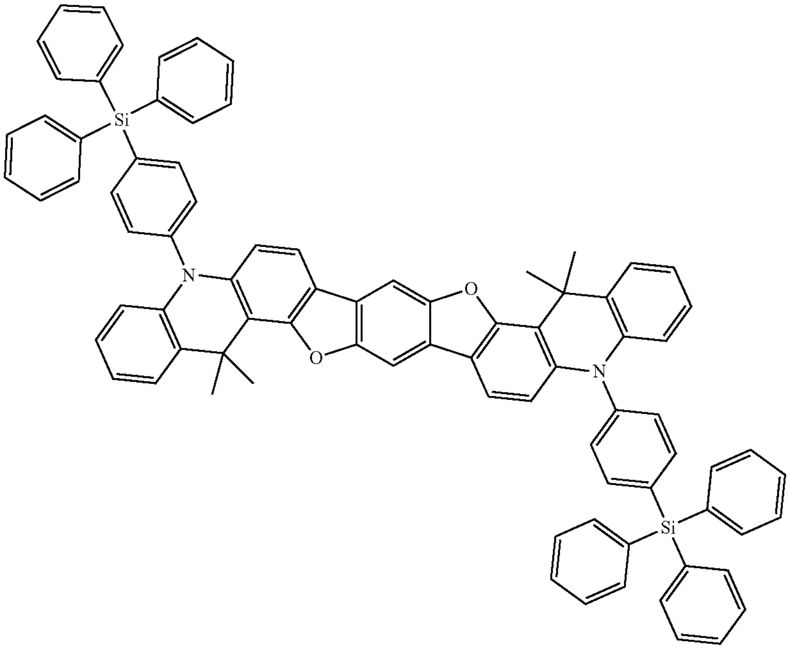

-continued
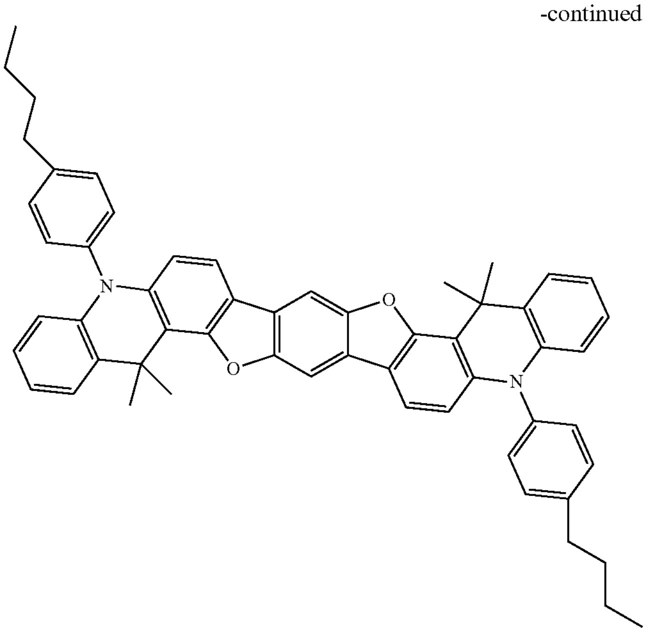
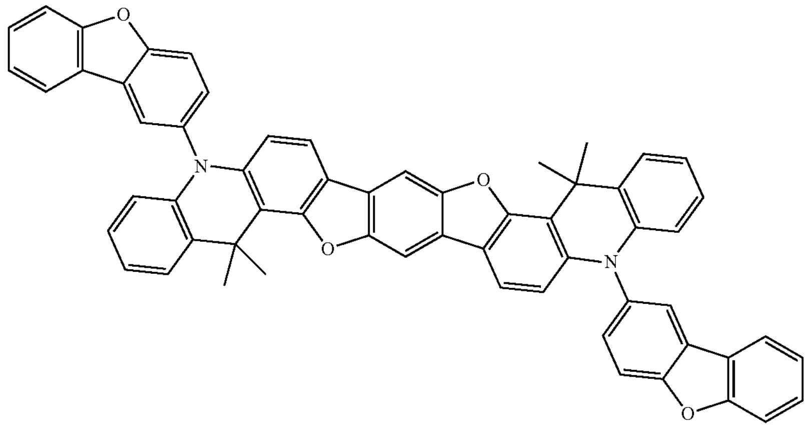 [SMILES: CC1(C)c2ccccc2N(c2ccc3oc4ccccc4c3c2)c2ccc3c(oc4cc5c(cc43)oc3c4c(ccc35)N(c3ccc5oc6ccccc6c5c3)c3ccccc3C4(C)C)c21]
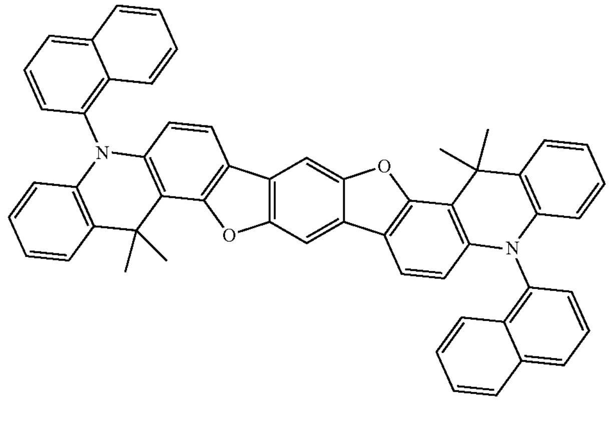

-continued
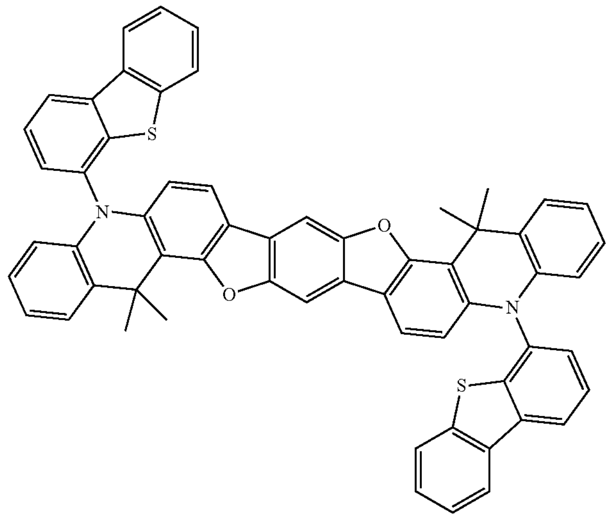
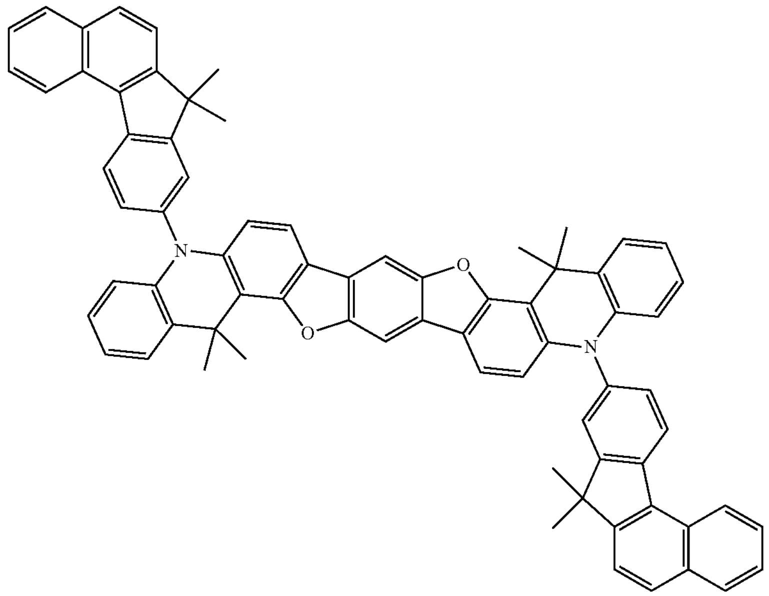
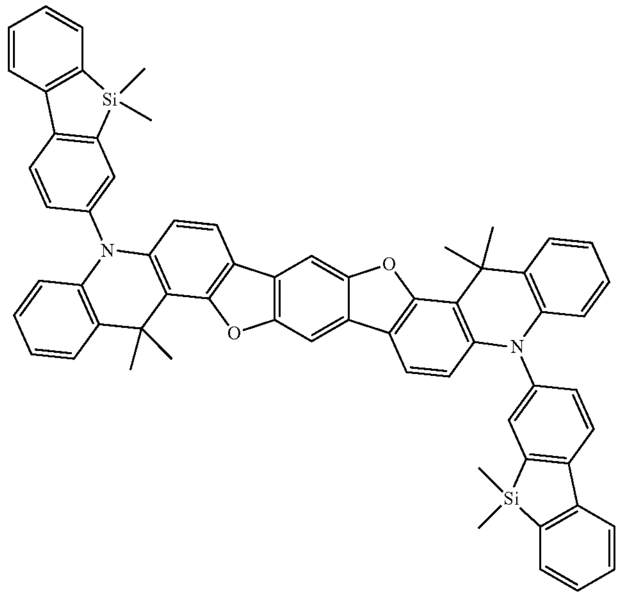

-continued
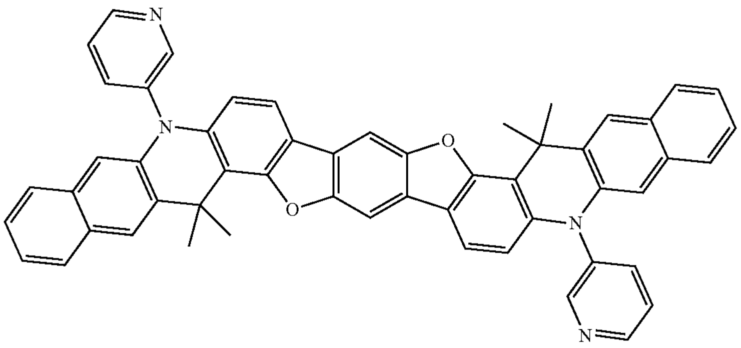
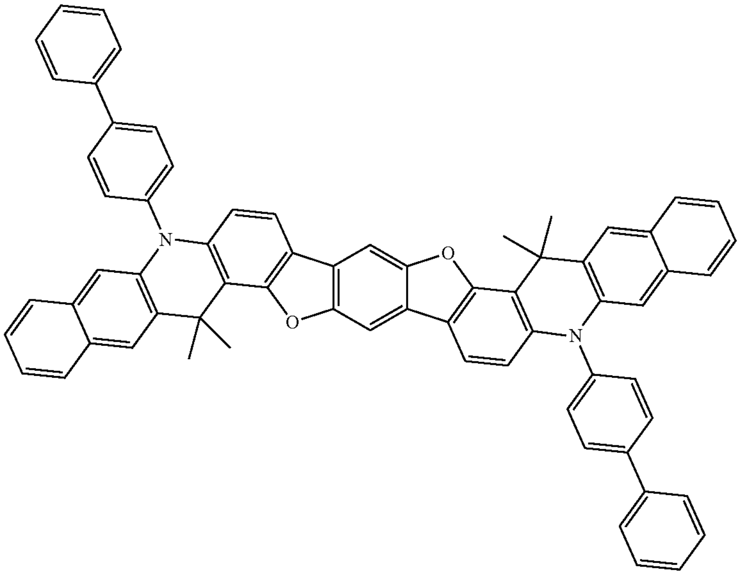
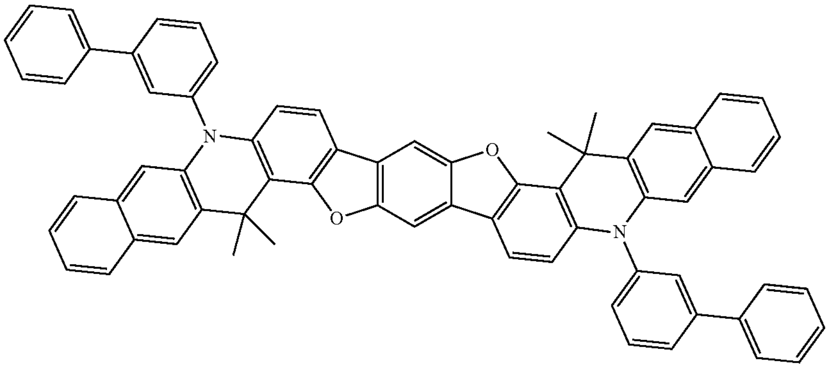

-continued
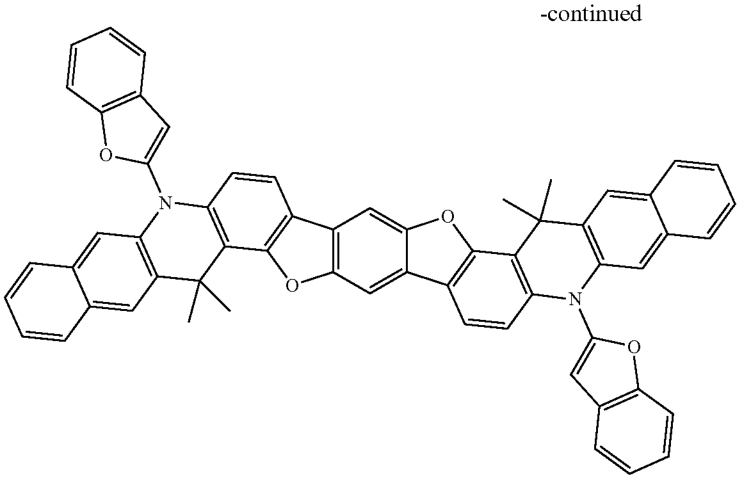
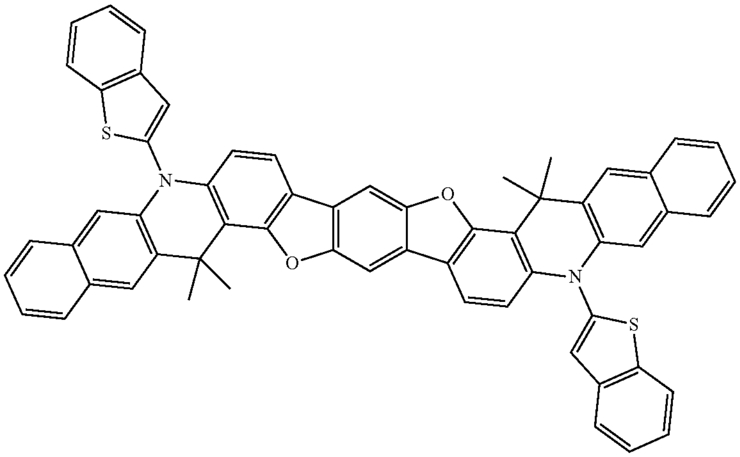
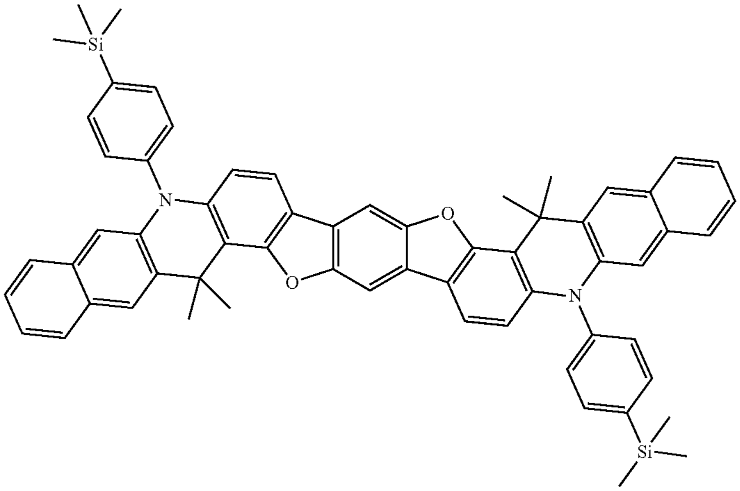

-continued
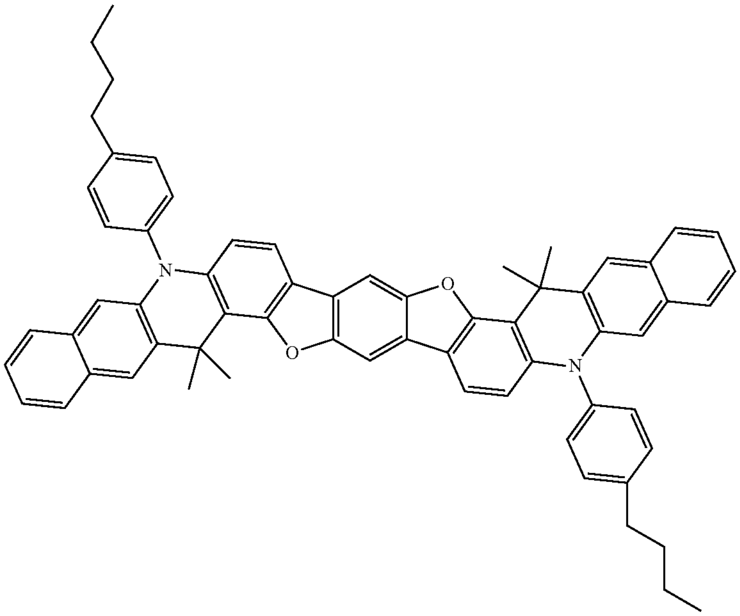
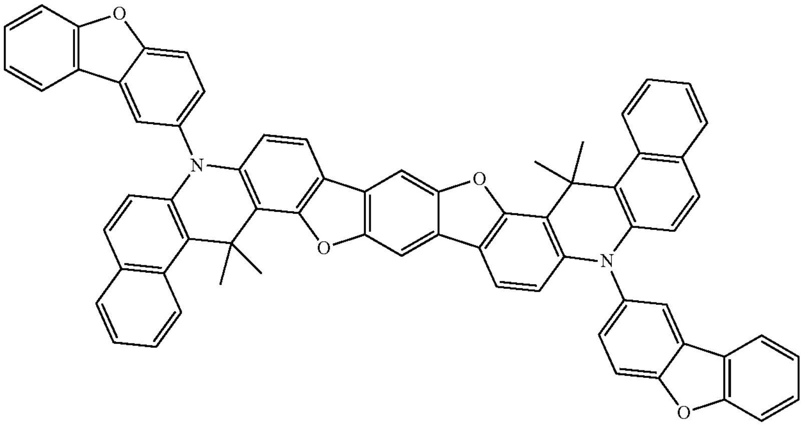
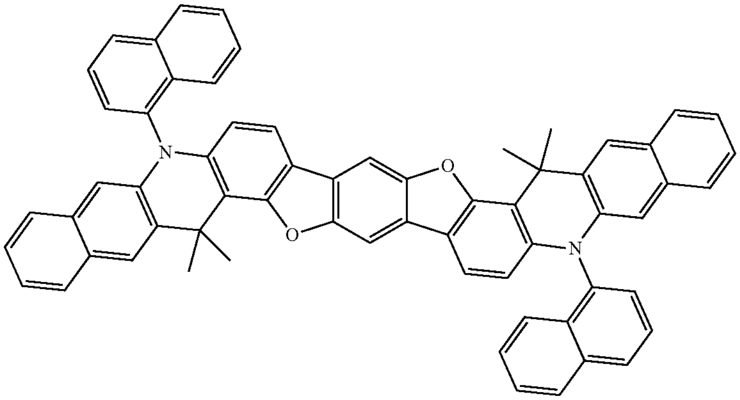

-continued
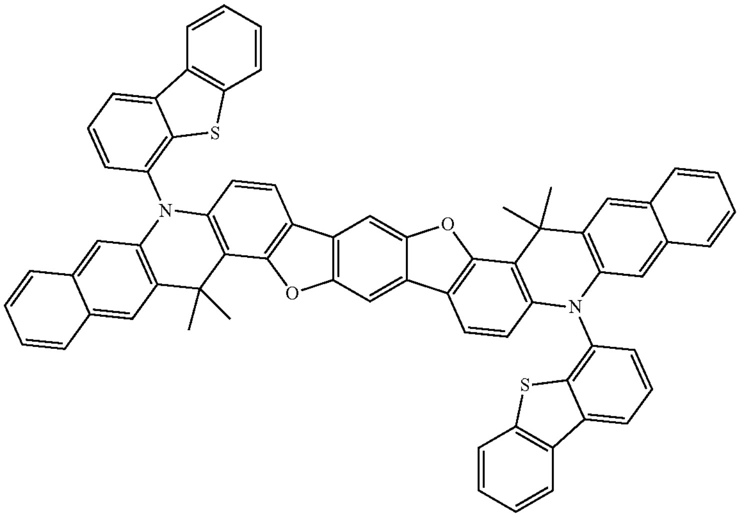
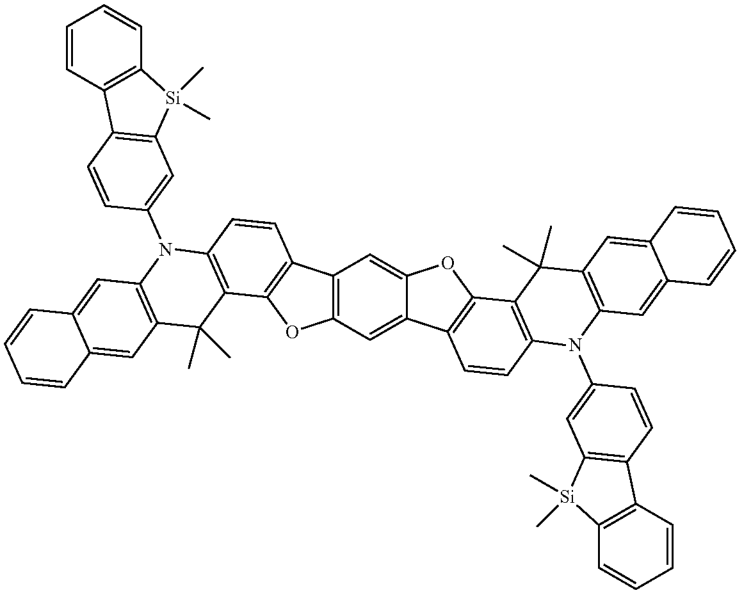

-continued
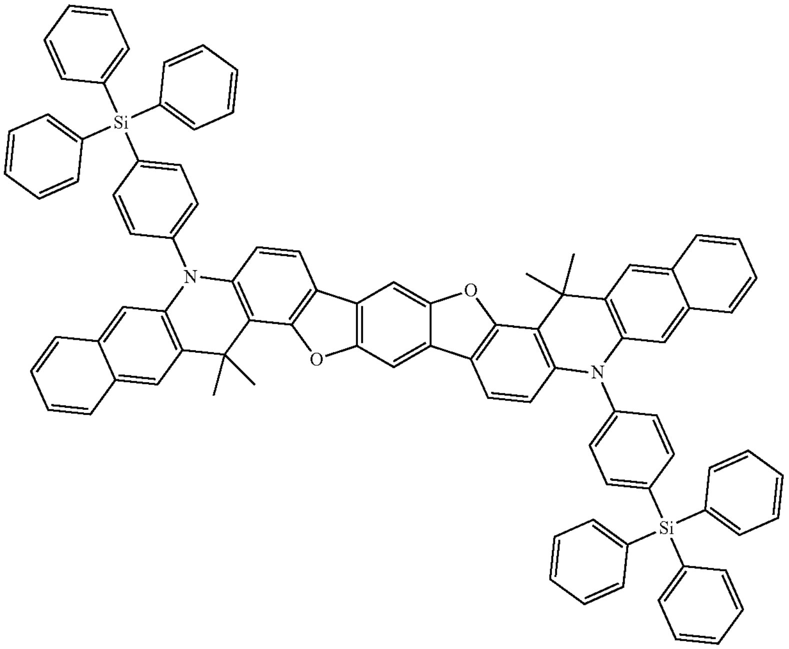
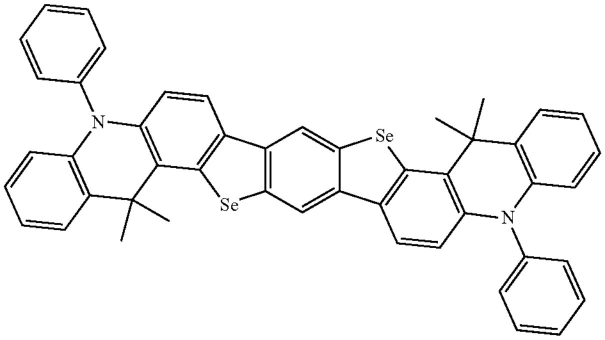
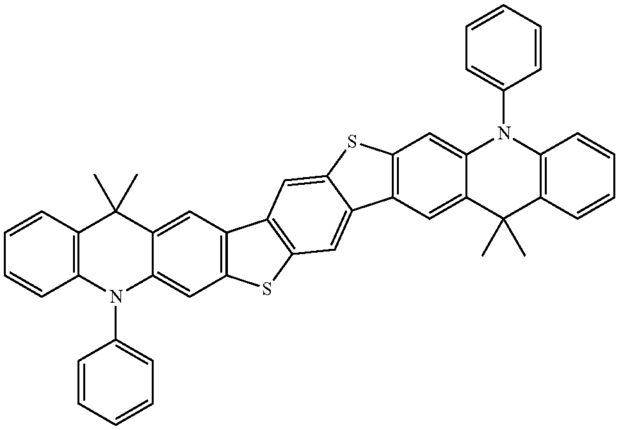
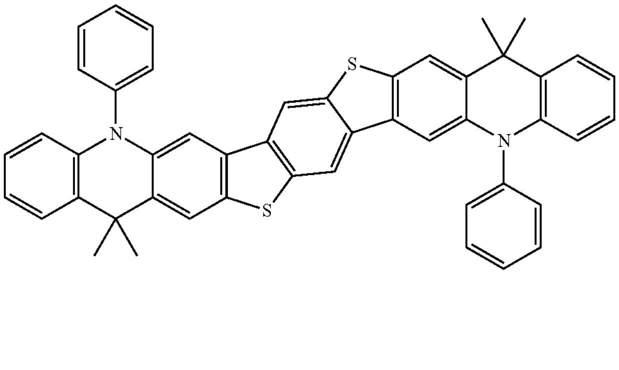

-continued
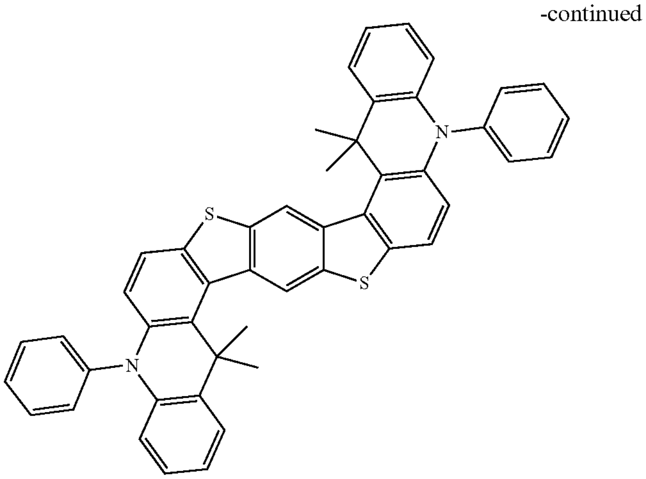
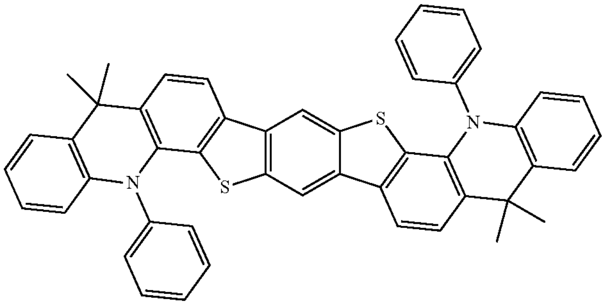
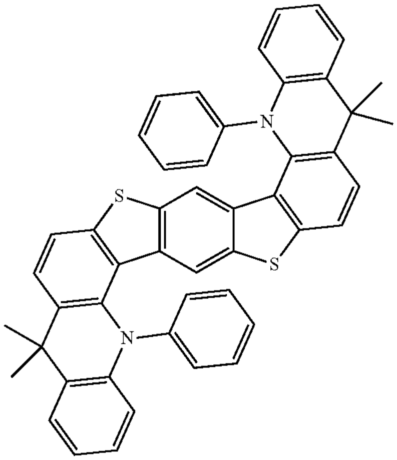
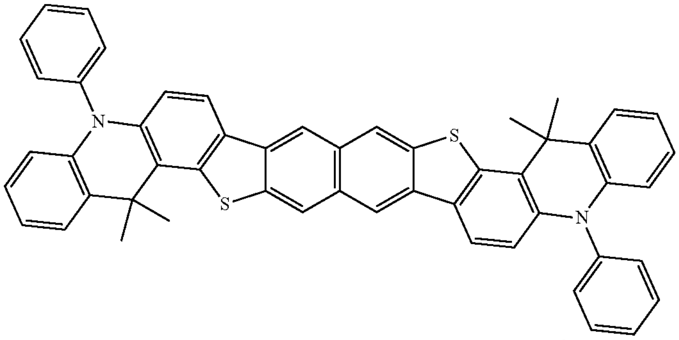
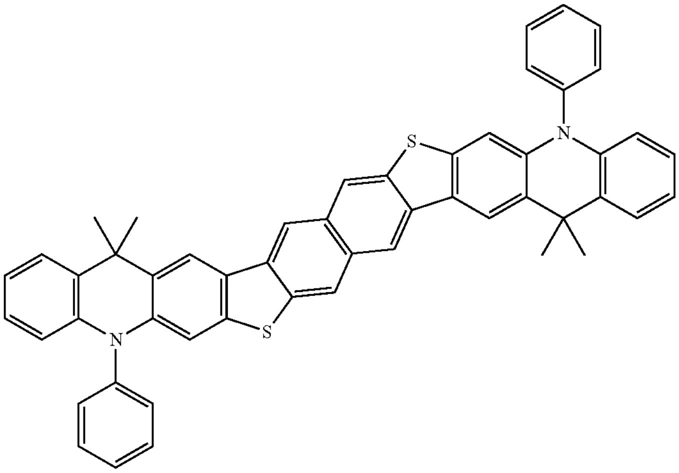

-continued
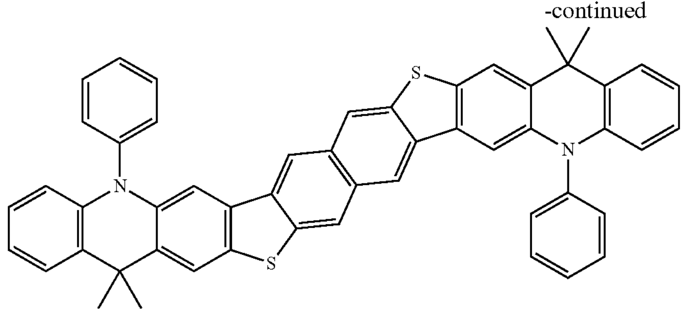
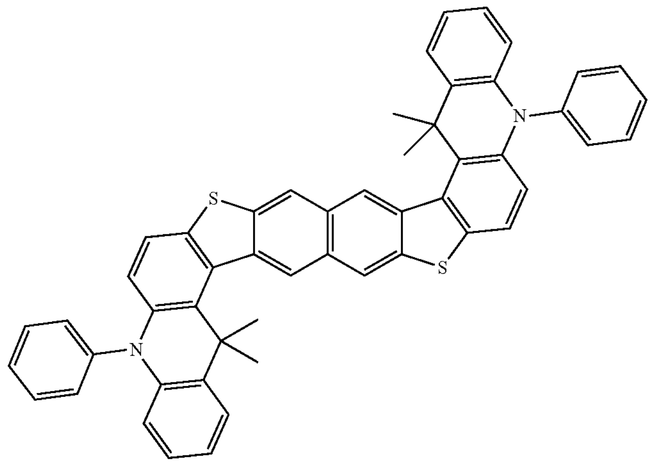
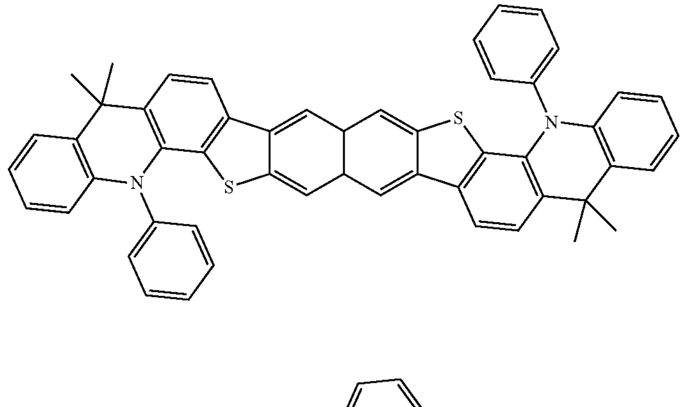
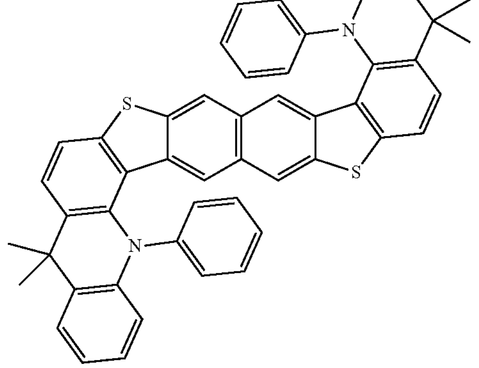

-continued
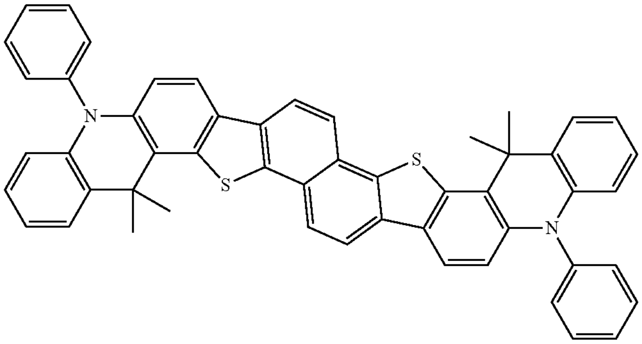
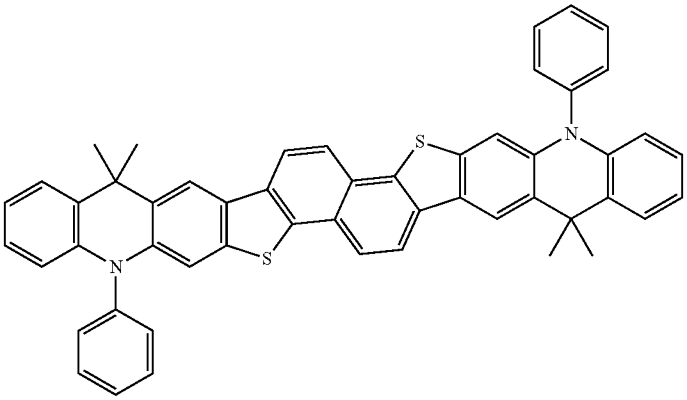
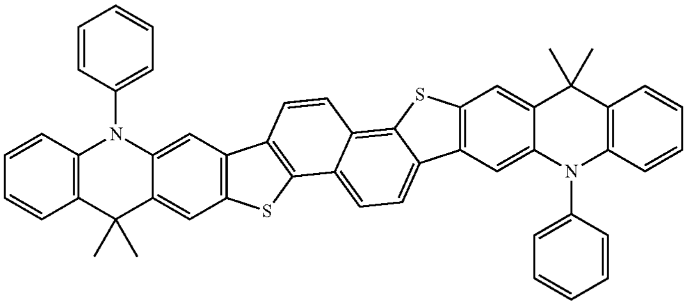
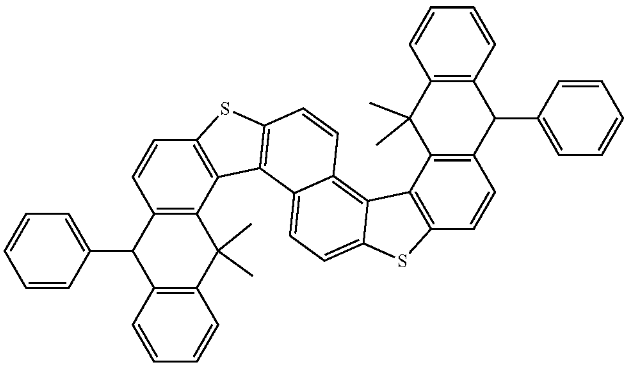

-continued
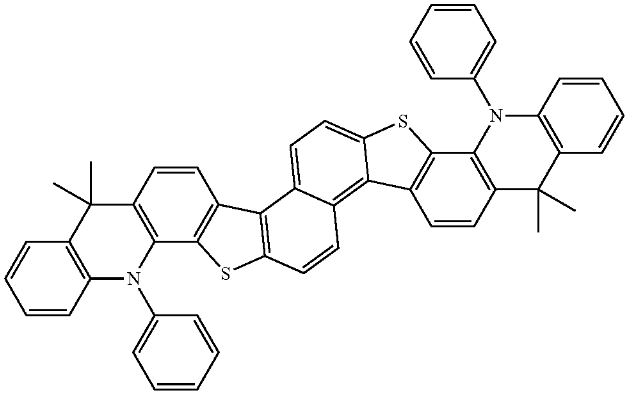
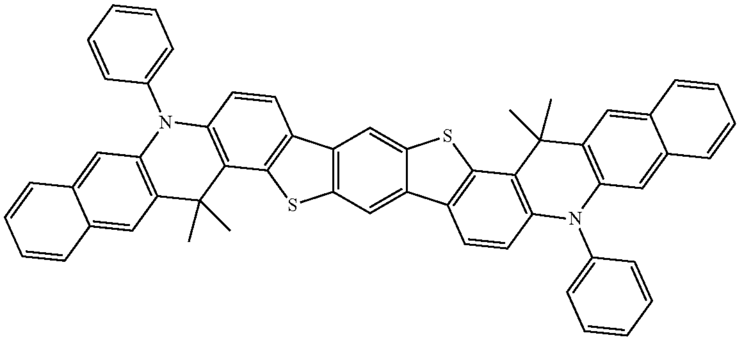
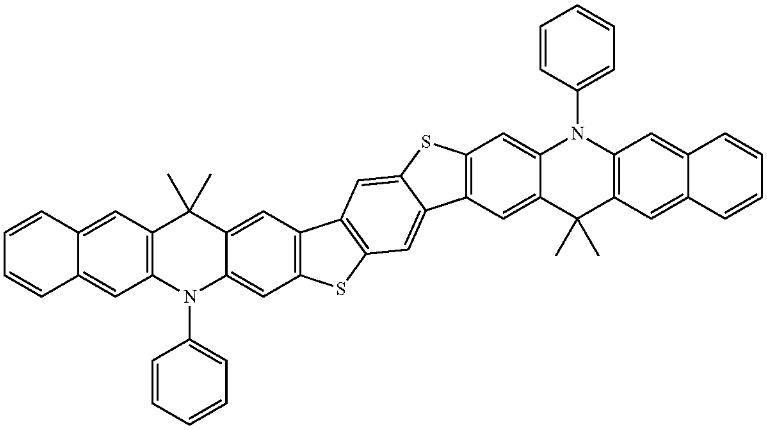
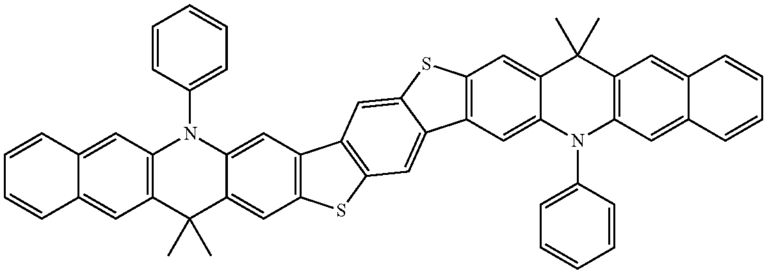

-continued
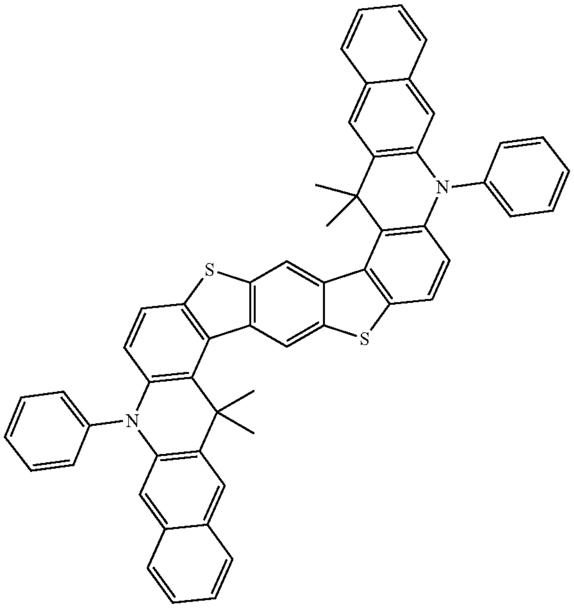
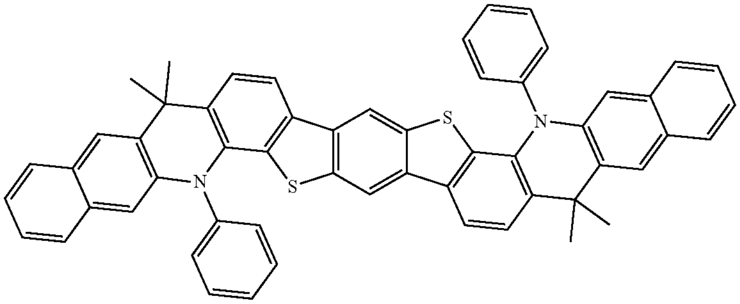
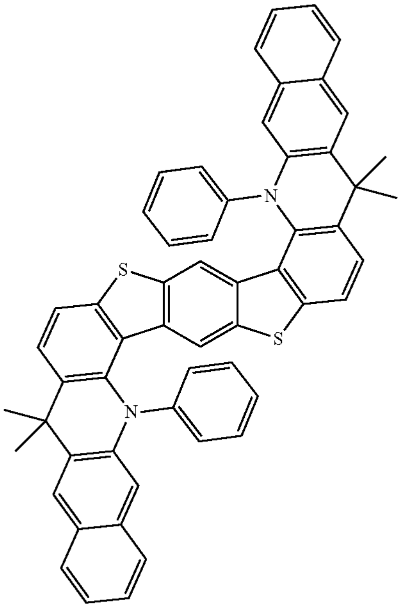

-continued
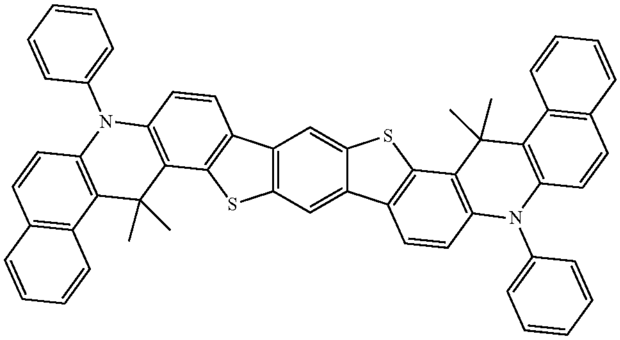
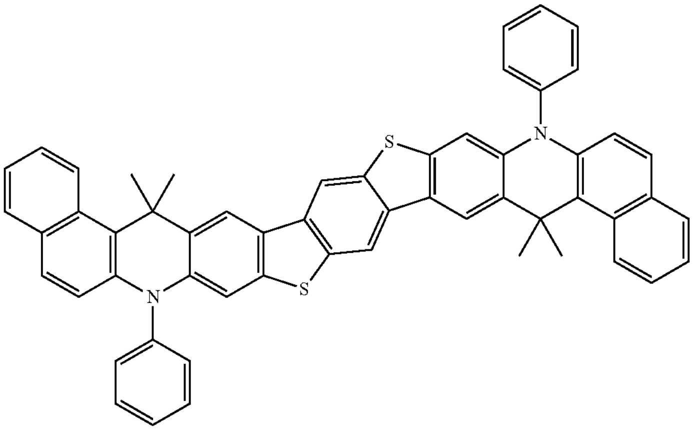
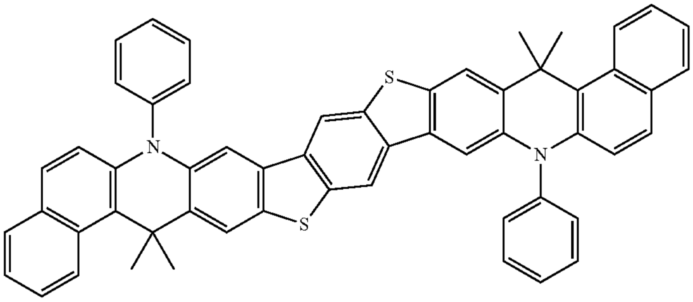
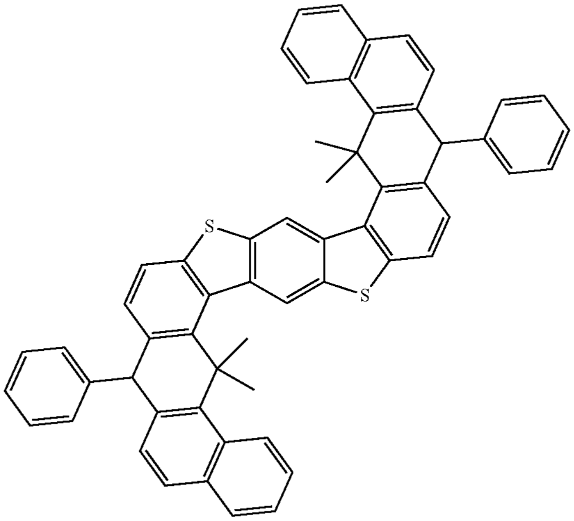

-continued
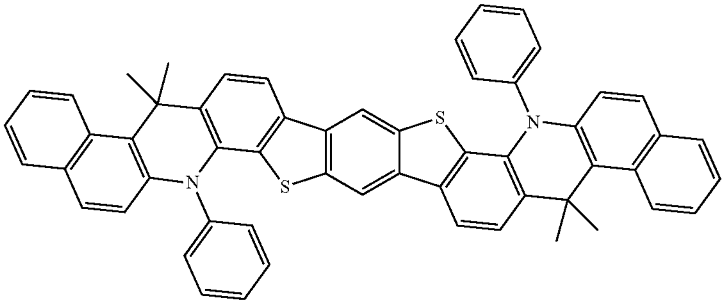
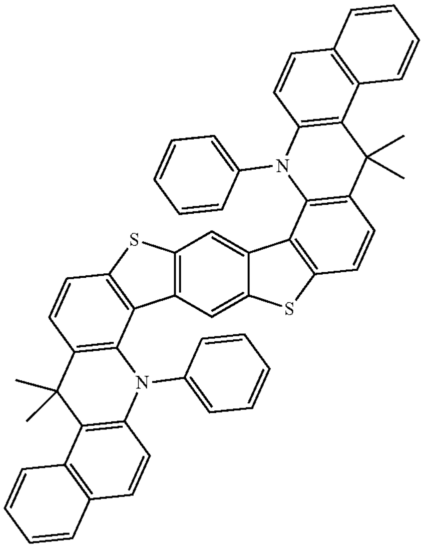
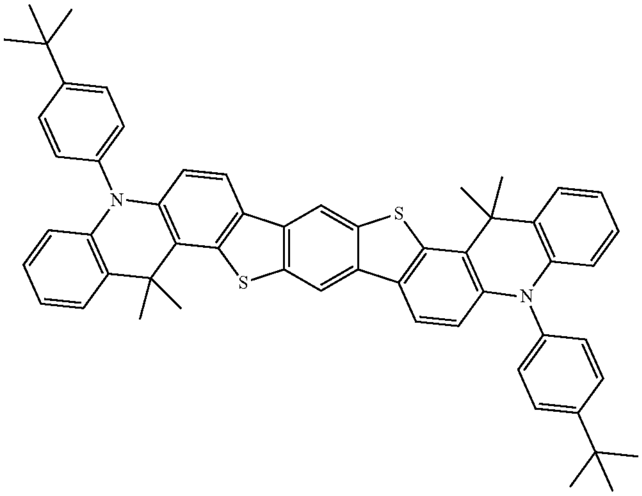
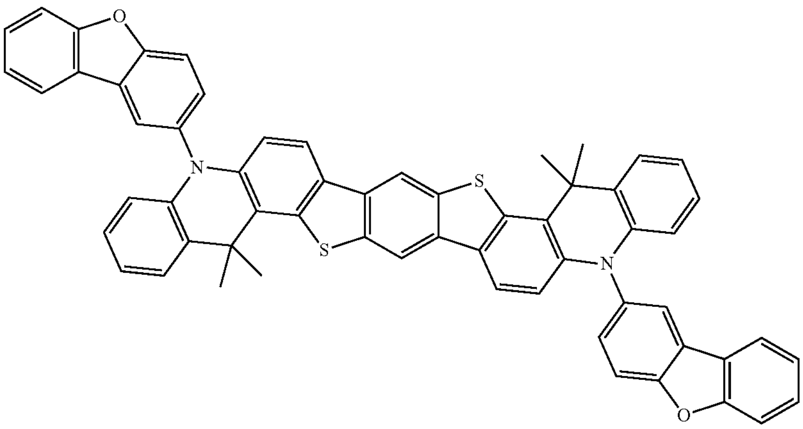

-continued
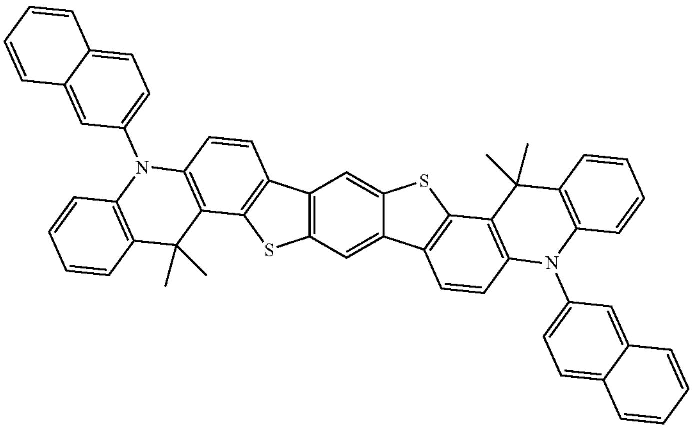
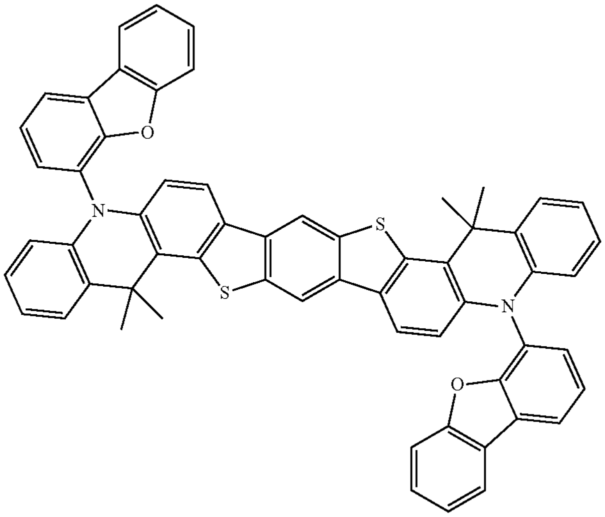
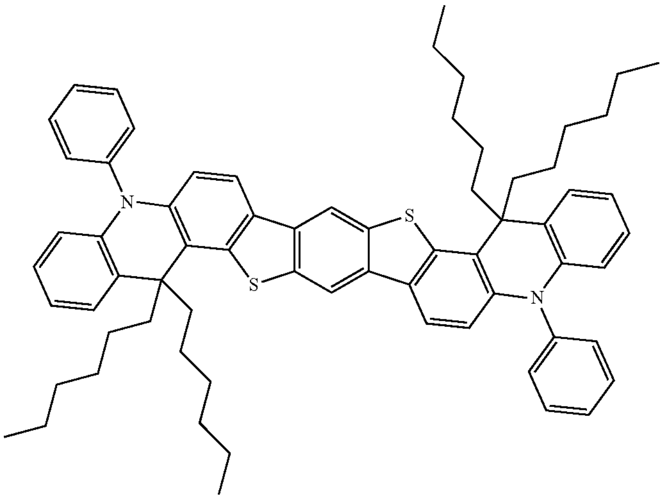

-continued

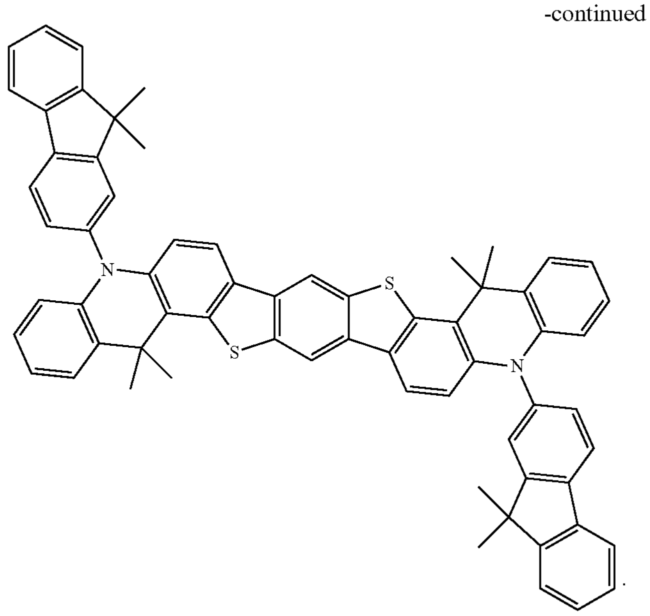

Meanwhile, among the compounds represented by Chemical Formula 1, when $X_1$ and $X_2$ are identical to each other, A2 and A3 are identical to each other, A4 and A5 are identical to each other, $Ar_1$ and $Ar_2$ are identical to each other, $R_1$ and $R_3$ are identical to each other and $R_2$ and $R_4$ are identical to each other, the compound can be prepared by the method as shown in the following Reaction Scheme 1, and other compounds may be prepared in a similar manner.

[Reaction Scheme 1]

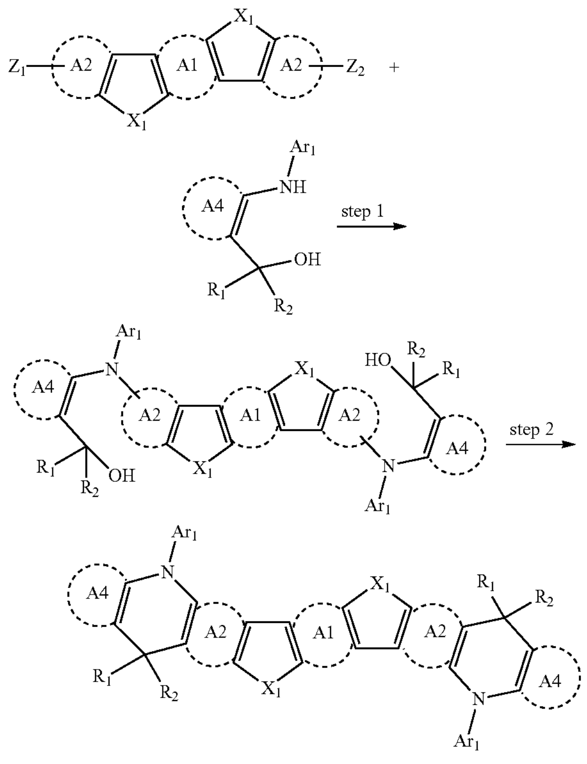

in Reaction Scheme 1, $X_1$, A1, A2, A4, $R_1$ and $R_2$ are as defined in Chemical Formula 1, $Z_1$ and $Z_2$ are each independently halogen, preferably $Z_1$ and $Z_2$ are each independently chloro or bromo.

Step 1 of the Reaction Scheme is an amine substitution reaction which is preferably carried out in the presence of a palladium catalyst and a base, and a reactive group for the amine substitution reaction can be modified as known in the art. Step 2 is an intramolecular cyclization reaction, and the reactive group, catalyst, solvent and the like used can be changed so as to suit to the desired product. The above preparation method may be further embodied in Preparation Examples described hereinafter.

Preferably, the compound according to the present disclosure may have a full width at half maximum of 36 nm or less. The full width at half maximum (FWHM) means the width between two wavelength values that represents half of the maximum intensity value by measuring the photoluminescence (PL) spectrum of the compound. Generally, the smaller the value, the higher the luminous efficiency. More preferably, the full width at half maximum of the compound according to the present disclosure may be 20 nm or more, 22 nm or more, 24 nm or more, 26 nm or more, 28 nm or more, or 29 nm or more, and 36 nm or less, 35 nm or less, 34 nm or less, or 33 nm or less.

Meanwhile, the organic material layer including the compound according to the present disclosure may be formed by using various methods such as a vacuum deposition process, a solution process, and the like, and the solution process will be described in detail below.

Coating Composition

The compound represented by Chemical Formula 1 according to the present disclosure can be included in an organic material layer of an organic light emitting device by a solution process. For this purpose, the present disclosure provides a coating composition including the above-mentioned compound represented by Chemical Formula 1 according to the present disclosure and a solvent.

The solvent is not particularly limited as long as it is a solvent capable of dissolving or dispersing the compound represented by Chemical Formula 1 according to the present disclosure. Examples of the solvent may include chlorine-based solvents such as chloroform, methylene chloride, 1,2-dichloroethane, 1,1,2-trichloroethane, chlorobenzene and o-dichlorobenzene; ether-based solvents such as tetrahydrofuran and dioxane; aromatic hydrocarbon-based solvents such as toluene, xylene, trimethylbenzene, and mesitylene; aliphatic hydrocarbon-based solvents such as cyclohexane, methylcyclohexane, n-pentane, n-hexane, n-heptane, n-octane, n-nonane and n-decane; ketone-based solvents such as acetone, methyl ethyl ketone, and cyclohexanone; ester-based solvents such as ethyl acetate, butyl acetate and ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol, and derivatives thereof; alcohol-based solvents such as methanol, ethanol, propanol, isopropanol and cyclohexanol; sulfoxide-based solvents such as dimethyl sulfoxide; amide-based solvents such as N-methyl-2-pyrrolidone and N,N-dimethylformamide; benzoate-based solvents such as butylbenzoate, and methyl-2-methoxybenzoate; tetraline; 3-phenoxy-toluene, and the like. In addition, the above-mentioned solvents may be used singly or in combination of two or more solvents.

Further, the coating composition may further include one, two or more types of additives selected from the group consisting of a thermal polymerization initiator and a photopolymerization initiator.

Examples of the thermal polymerization initiator may include peroxides such as methyl ethyl ketone peroxide, methyl isobutyl ketone peroxide, acetyl acetone peroxide, methyl cyclohexanone peroxide, cyclohexanone peroxide, isobutyryl peroxide, 2,4-dichlorobenzoyl peroxide, bis-3,5,5-trimethylhexanoyl peroxide, lauryl peroxide, benzoyl peroxide, or azo-based such as azobis isobutylnitrile, azobis dimethylvaleronitrile and azobis cyclohexylnitrile, but are not limited thereto.

Examples of the photopolymerization initiator may include acetophenone-based or ketal-based photopolymerization initiators such as diethoxyacetophenone, 2,2-dimethoxy-1,2-diphenylethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl)propan-1-one and 1-phenyl-1,2-propanedion-2-(o-ethoxycarbonyl)oxime, benzoin ether-based photopolymerization initiators such as benzoin, benzoin methyl ether, and benzoin ethyl ether; benzophenone-based photopolymerization initiators such as benzophenone, 4-hydroxybenzophenone, 2-benzoyl naphthalene, 4-benzoylbiphenyl and 4-benzoylphenyl ether; thioxanthone-based photopolymerization initiators such as 2-isopropylthioxanthone, 2-chlorothioxanthone, 2,4-dimethylthioxanthone, 2,4-diethylthioxanthone and 2,4-dichlorothioxanthone; and other photopolymerization initiators such as ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, and bis(2,4-dimethoxy benzoyl)-2,4,4-trimethylpentylphosphine oxide, but are not limited thereto.

Moreover, those having a photopolymerization promoting effect may also be used alone or in combination with the photopolymerization initiator. Examples thereof include triethanolamine, methyldiethanolamine, ethyl 4-dimethylaminobenzoate, isoamyl 4-dimethylamino benzoate, (2-dimethylamino) ethyl benzoate, 4,4'-dimethylaminobenzophenone, and the like, but are not limited thereto.

Further, the viscosity of the coating composition is preferably 1 cP or more. In consideration of the ease of coating of the coating composition, the viscosity of the coating composition is preferably 10 cP or less. Further, the concentration of the compound according to the present disclosure in the coating composition is preferably 0.1 wt/v % or more. In addition, the concentration of the compound according to the present disclosure in the coating composition is preferably 20 wt/v % or less so that the coating composition can be optimally coated.

In another embodiment of the present disclosure, there is provided a method for forming a light emitting layer using the above-mentioned coating composition. Specifically, the method includes the steps of: coating the above-mentioned light emitting layer according to the present disclosure onto the anode; or on the hole transport layer formed on the anode; or on the hole injection layer formed on the anode by a solution process; and heat-treating or photo-treating the coated coating composition.

The solution process uses the above-mentioned coating composition according to the present disclosure, and refers to spin coating, dip coating, doctor blading, inkjet printing, screen printing, spray method, roll coating, and the like, but is not limited thereto.

The heat treatment temperature in the heat treatment step is preferably from 150 to 230° C. Further, a heat treatment time may be 1 minute to 3 hours, more preferably 10 minutes to 1 hour. Further, the heat treatment is preferably carried out in an inert gas atmosphere such as argon and nitrogen. In addition, the step of evaporating the solvent may be further included between the coating step and the heat treatment or the photo treatment step.

Organic Light Emitting Device

In another embodiment of the present disclosure, there is provided an organic light emitting device including the above-mentioned polymer according to the present disclosure. In one example, the present disclosure provides an organic light emitting device comprising: a first electrode; a second electrode that is provided opposite to the first electrode; and one or more organic material layers that are provided between the first electrode and the second electrode, wherein one or more layers of the organic material layers include the compound represented by Chemical Formula 1.

The organic material layer of the organic light emitting device of the present disclosure may have a single-layer structure, or it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a light emitting layer, wherein the light emitting layer may include the compound represented by Chemical Formula 1.

Further, the organic material layer may include a hole transport layer, or a hole injection layer, wherein the hole transport layer, or the hole injection layer may include the compound represented by Chemical Formula 1.

Further, the organic material layer may include an electron transport layer, an electron injection layer, or a layer for simultaneously performing electron injection and transport.

Further, the organic material layer may include a light emitting layer and a hole transport layer, wherein the light emitting layer or the hole transport layer may include the compound represented by Chemical Formula 1.

Further, the organic light emitting device according to the present disclosure may be a normal type organic light emitting device in which an anode, one or more organic material layers and a cathode are sequentially stacked on a substrate. Further, the organic light emitting device according to the present disclosure may be an inverted type organic light emitting device in which a cathode, one or more organic material layers and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound represented by Chemical Formula I may be included in the light emitting layer.

FIG. 2 shows an example of an organic light emitting device comprising a substrate 1, an anode 2, a hole injection layer 5, a hole transport layer 6, a light emitting layer 3, an electron transport layer 7, an electron injection layer 8, and a cathode 4. In such a structure, the compound represented by Chemical Formula i may be included in at least one of the hole injection layer, the hole transport layer, and the light emitting layer.

The organic light emitting device according to the present disclosure may be manufactured by materials and methods known in the art, except that at least one of the organic material layers includes the compound represented by Chemical Formula 1. Further, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

Further, the compound represented by Chemical Formula 1 may be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

In one example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive compounds such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport layer is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a spiro compound; polyfluorene, lubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto. The compound represented by Chemical Formula 1 can include as the dopant material.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer may be used together with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

In addition to the above-mentioned materials, the light emitting layer, the hole injection layer, the hole transport layer, the electron transport layer, and the electron injection layer may further include an inorganic compound such as quantum dots or a polymer compound.

The quantum dots may be, for example, colloidal quantum dots, alloy quantum dots, core-shell quantum dots, or core quantum dots. It may be a quantum dot including elements belonging to groups 2 and 16, elements belonging to groups 13 and 15, elements belonging to groups 13 and 17, elements belonging to groups 11 and 17, or elements belonging to groups 14 and 15. Quantum dots including elements such as cadmium (Cd), selenium (Se), zinc (Zn), sulfur (S), phosphorus (P), indium (In), tellurium (Te), lead (Pb), gallium (Ga), arsenic (As) may be used.

The organic light emitting device according to the present disclosure may be a bottom emission device, a top emission device, or a double-sided light emitting device, and in particular, may be a bottom emission device that requires relatively high luminous efficiency.

In addition, the compound represented by Chemical Formula 1 may be included in an organic solar cell or an organic transistor in addition to an organic light emitting device.

Hereinafter, preferred examples are presented to assist in the understanding of the present disclosure. However, the following examples are only provided for a better understanding of the present disclosure, and is not intended to limit the content of the present disclosure.

PREPARATION EXAMPLE

Preparation Example 1: Preparation of Compound 1

Preparation Example 1-1: Preparation of Intermediate a1

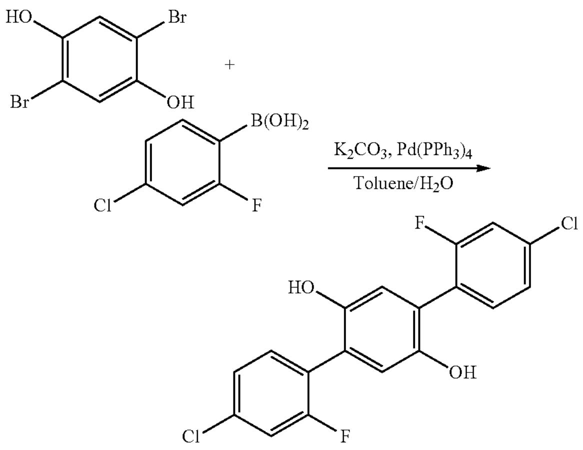

a1

2,5-Dibromobenzene-1,4-diol (10.0 g, 37.3 mmol), (4-chloro-2-fluorophenyl)boronic acid (14.3 g, 82.1 mmol), potassium carbonate (25.8 g, 186.5 mmol), and $Pd(PPh_3)_4$ (4.3 g, 3.73 mmol) were placed in a 500 mL round bottom flask, to which 190 mL of anhydrous toluene (0.2 M) and 40 mL of distilled water were added. The mixture was stirred overnight at a bath temperature of 100° C. The reaction mixture was cooled to room temperature, and then passed through a pad of celite/florisil/silica while toluene was flowing. The result was subjected to column purification with ethyl acetate and hexane, and then precipitated with methanol/tetrahydrofuran to obtain Intermediate a1.

Preparation Example 1-2: Preparation of Intermediate a2

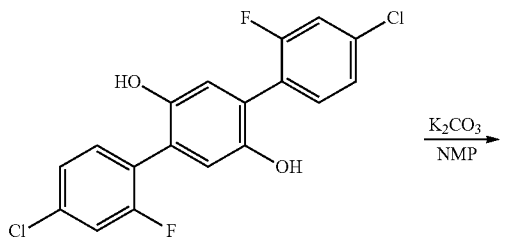

a1

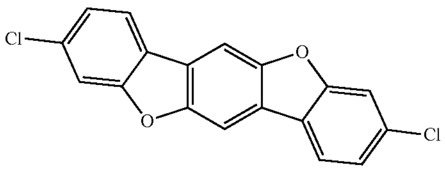

a2

Intermediate a1 (5.0 g, 13.6 mmol) and potassium carbonate (9.4 g, 68.0 mmol) were placed in a 500 mL round bottom flask, and dissolved in 140 mL of NMP (0.1 M), and then the mixture was stirred overnight at a bath temperature of 180° C. After cooling to room temperature, hexane and water were added dropwise, precipitated, filtered, and washed with tetrahydrofuran and methanol to obtain Intermediate a2.

Preparation Example 1-3: Preparation of Intermediate a4

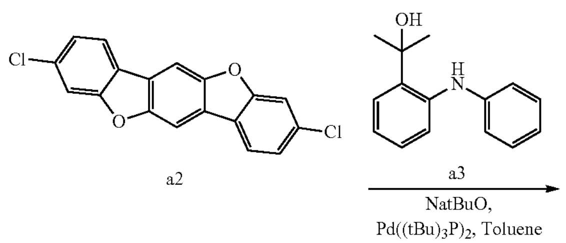

a2 a3

-continued

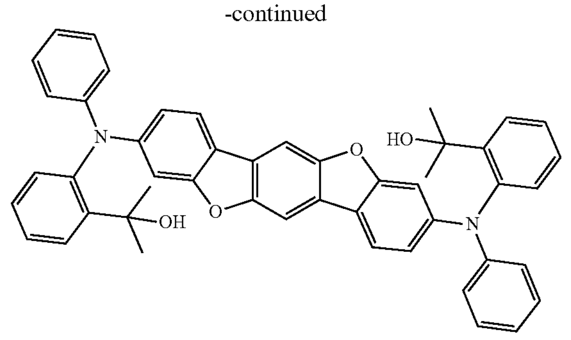

a4

Intermediate a2 (3.0 g, 9.2 mmol), Intermediate a3 (6.3 g, 27.6 mmol), sodium t-butoxide (3.5 g, 36.8 mmol), and $Pd(P(t\text{-}Bu)_3)_2$ (0.47 g, 0.92 mmol) were placed in a 1 L round bottom flask and filled with nitrogen, to which 370 mL of toluene (0.025 M) was added. Then, the mixture was stirred for 6 hours at a bath temperature of 110° C. After cooling to room temperature, the mixture was washed with water, hexane, and methanol, and precipitated with methanol/tetrahydrofuran to obtain Intermediate a4.

Preparation Example 1-4: Preparation of Compound 1

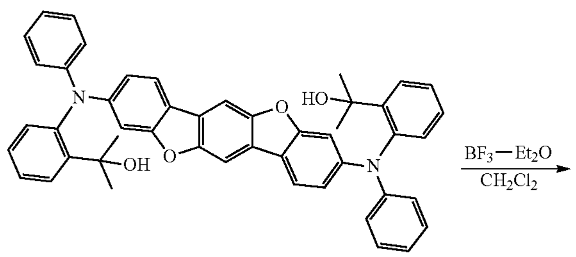

a4

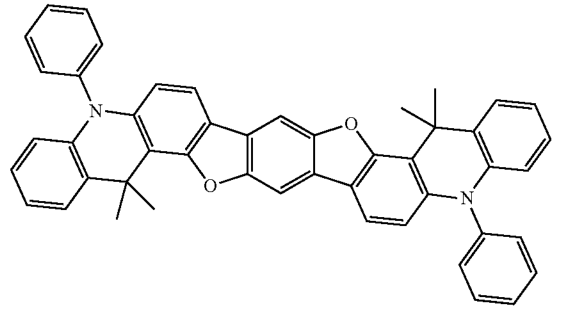

1

Intermediate a4 (2.0 g, 2.8 mmol) was placed in a 250 mL round bottom flask and filled with nitrogen, to which 110 mL of dichloromethane (0.025 M) was added. Boron trifluoride diethyl etherate (1.6 g, 11.2 mmol) was added dropwise thereto at 0° C., and the mixture was stirred at room temperature for 4 hours. The reaction mixture was washed with water, hexane and methanol, and recrystallized from chlorobenzene to obtain Compound 1.

MS: $[M+H]^+$=673

Preparation Example 2: Preparation of Compound 2
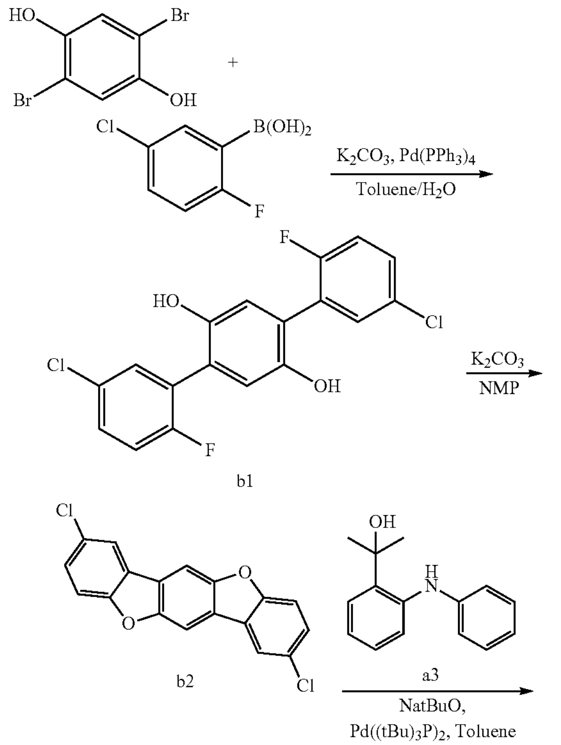
b1
b2
a3
-continued
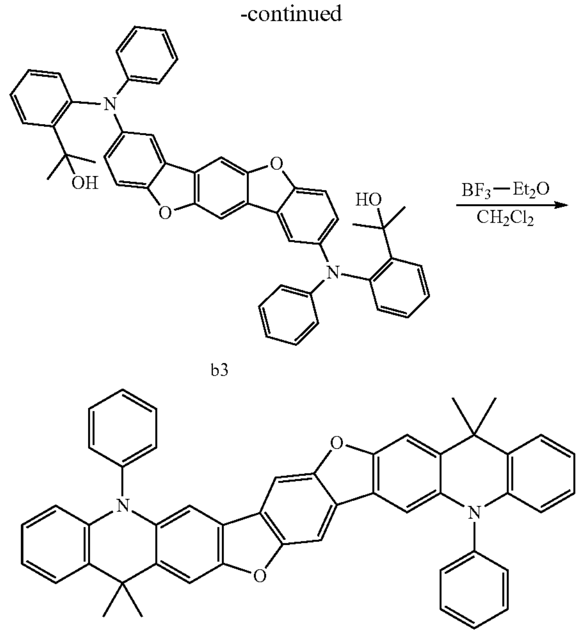
b3
2
Compound 2 was prepared in the same manner as in Preparation Example 1, except that (5-chloro-2-fluorophenyl)boronic acid was used instead of (4-chloro-2-fluorophenyl)boronic acid of Preparation Example 1-1.
MS: $[M+H]^+=673$
Preparation Example 3: Preparation of Compound 3
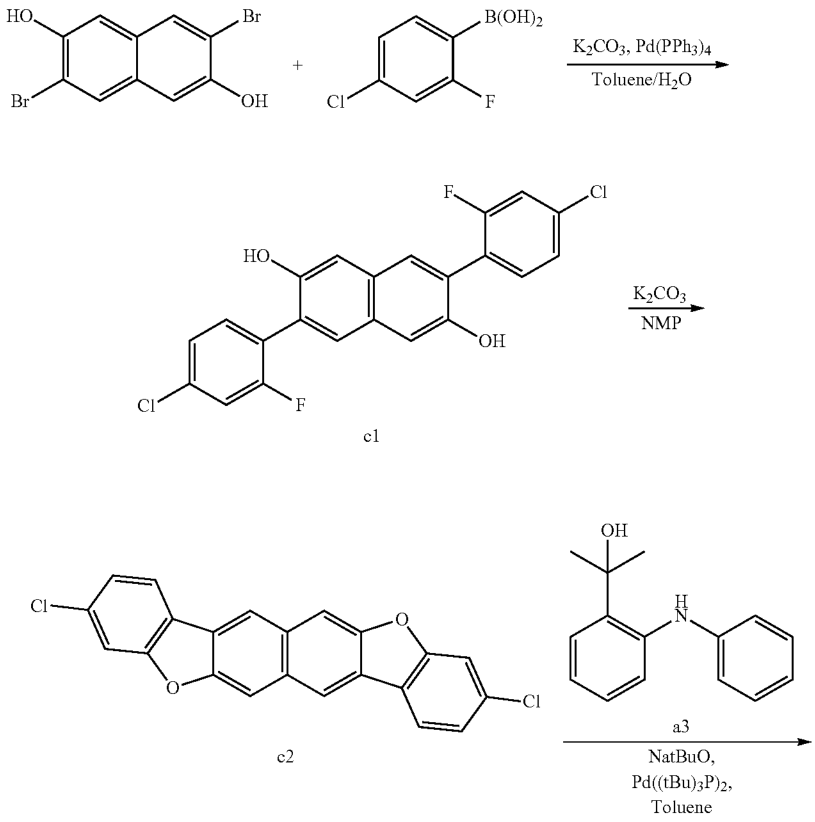
c1
c2
a3

-continued
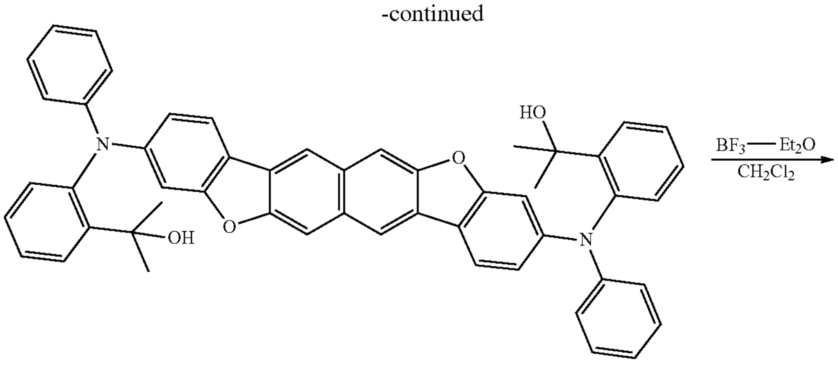
c3
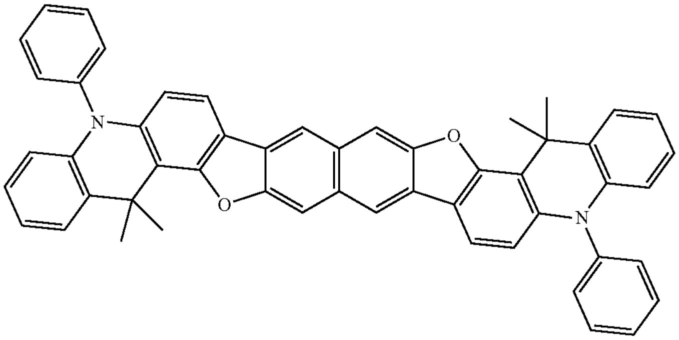
3
Compound 3 was prepared in the same manner as in Preparation Example 1, except that 3,7-dibromonaphthalene-2,6-diol was used instead of 2,5-dibromobenzene-1,4-diol of Preparation Example 1-1.
MS: $[M+H]^+=723$
Preparation Example 4: Preparation of Compound 4
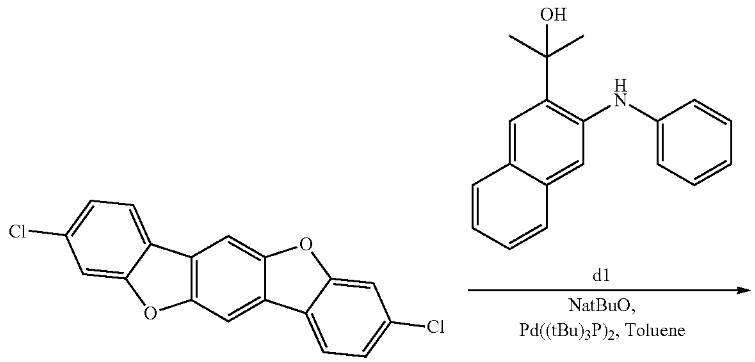
a2

-continued
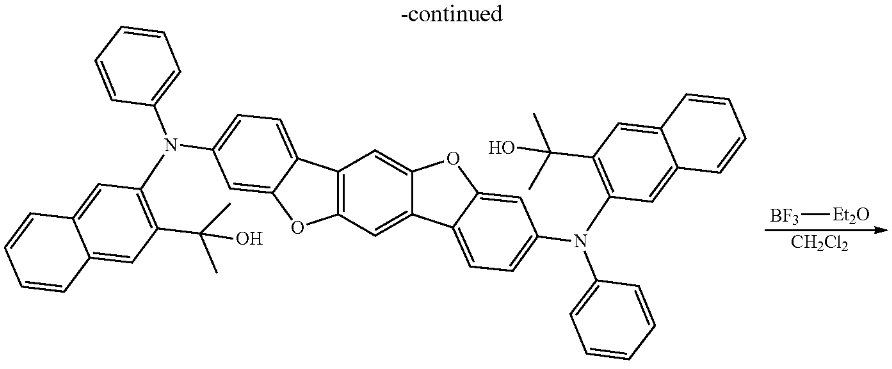
d2
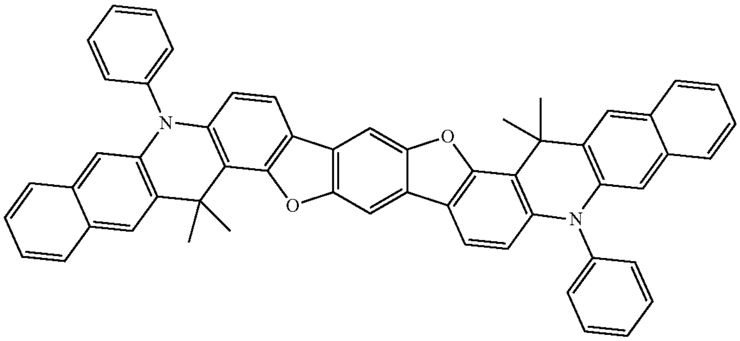
4
Compound 4 was prepared in the same manner as in Preparation Example 1, except that Intermediate dl was used instead of Intermediate a3 of Preparation Example 1-3.
MS: $[M+H]^+$=773
Preparation Example 5: Preparation of Compound 5
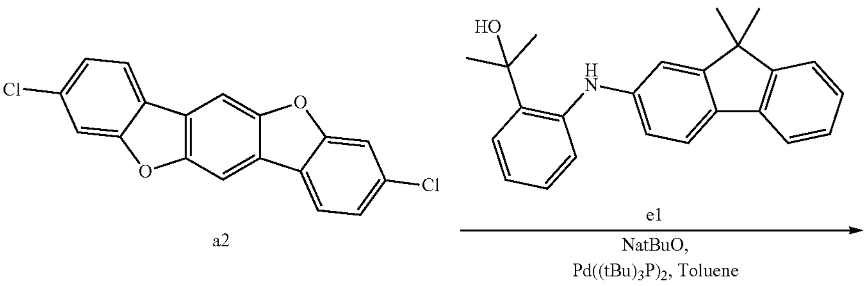
a2

-continued
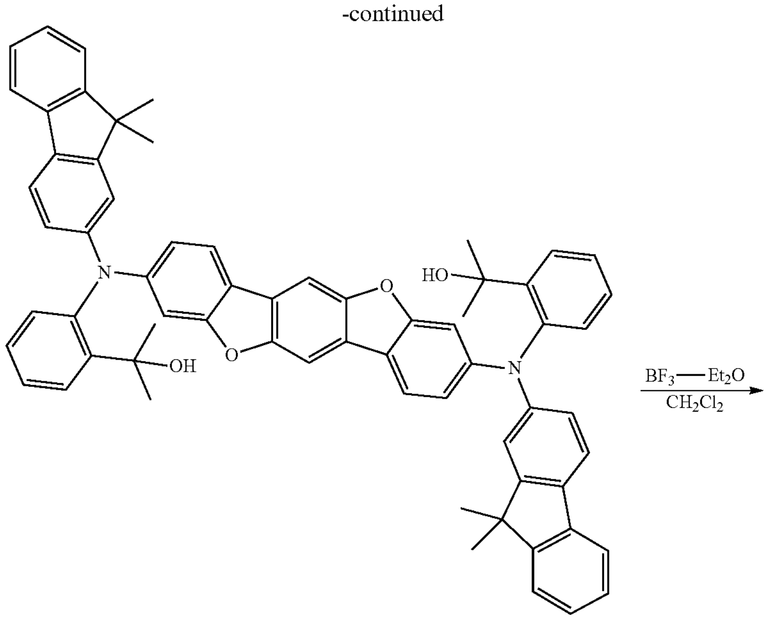
e2
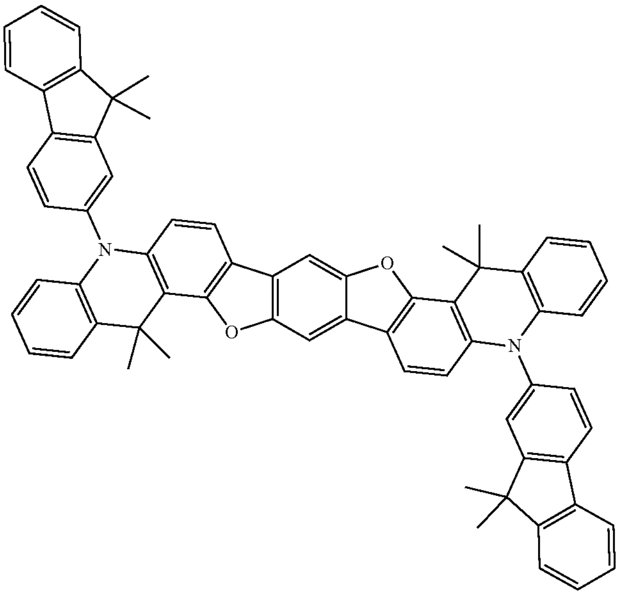
5
Compound 5 was prepared in the same manner as in Preparation Example 1, except that Intermediate el was used instead of Intermediate a3 of Preparation Example 1-3.
MS: $[M+H]^+=905$
Preparation Example 6: Preparation of Compound 6
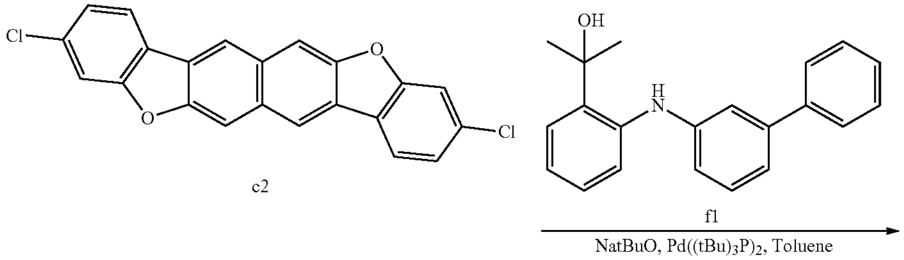
c2
f1

-continued

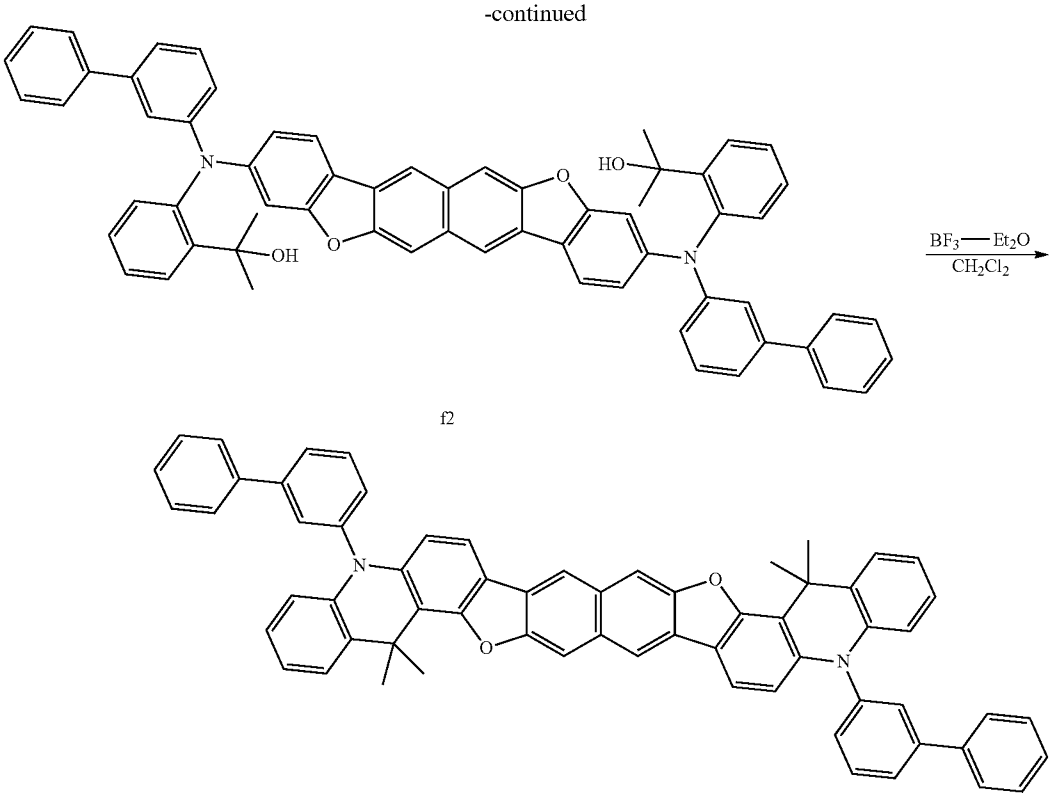

f2

6

Compound 6 was prepared in the same manner as in Preparation Example 3, except that Intermediate f1 was used instead of Intermediate a3 of Preparation Example 3.

MS: $[M+H]^+$=875

Preparation Example 7: Preparation of Compound A

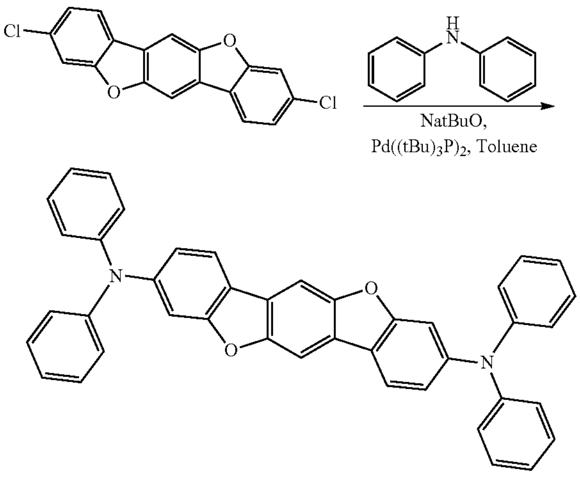

A

Compound A was prepared in the same manner as in Preparation Example 1-3, except that diphenylamine was used instead of Intermediate a3 of Preparation Example 1-3.

MS: $[M+H]^+$=593

EXAMPLE

Example 1: Manufacture of Organic Light Emitting Device

A glass substrate thinly coated with indium tin oxide (ITO) to have a thickness of 500 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, the substrate was ultrasonically cleaned with acetone, distilled water and isopropyl alcohol, dried, and thereby, the cleaned ITO glass substrate was prepared.

A composition in which the following compound Z-1 and the following compound Z-2 were mixed in a weight ratio of 8:2 was spin-coated onto the ITO transparent electrode, and cured at 220° C. for 30 minutes on a hot plate under a nitrogen atmosphere to form a hole injection layer with a thickness of 400 Å. A composition in which the following compound Z-3 was dissolved in toluene at 1 weight % was spin-coated onto the hole injection layer, and heat-treated at 200° C. for 30 minutes on a hot plate to form a hole transport layer with a thickness of 200 Å. A composition in which the following compound Z-4 and the previously prepared Compound 1 were dissolved in 0.5 wt % toluene in a weight ratio of 98:2, was spin-coated on the hole transport layer to form a light emitting layer with a thickness of 250 Å. The coating composition was dried on a hot plate at 120° C. for 10 minutes under a nitrogen atmosphere. Then, it was transferred to a vacuum evaporator, and the following compounds Z-5 (electron transport layer, 300 Å), LiF (electron injection layer, 10 Å), and A1 (cathode, 1000 Å) were sequentially deposited to manufacture an organic light emitting device. In the above-mentioned process, the deposition rate of LiF was maintained at 0.3 Å/sec, the deposition rate of aluminum (Al) was maintained at 2 Å/sec, and the degree of vacuum during the deposition was maintained at $2*10^{-7}$ to $5*10^{-8}$ torr.

Z-1

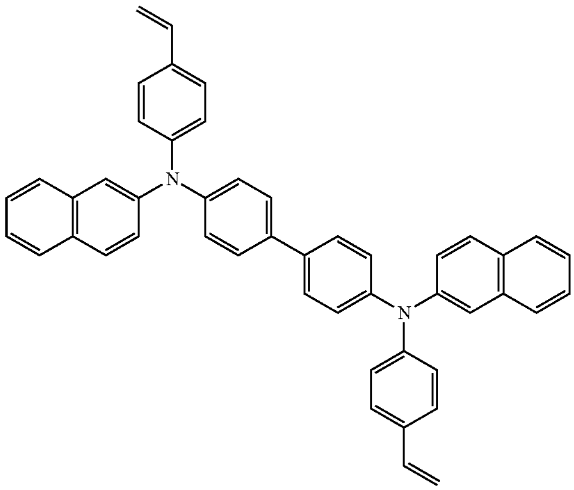

Z-2

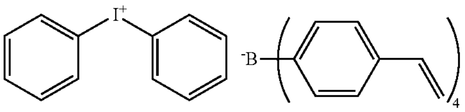

Z-3

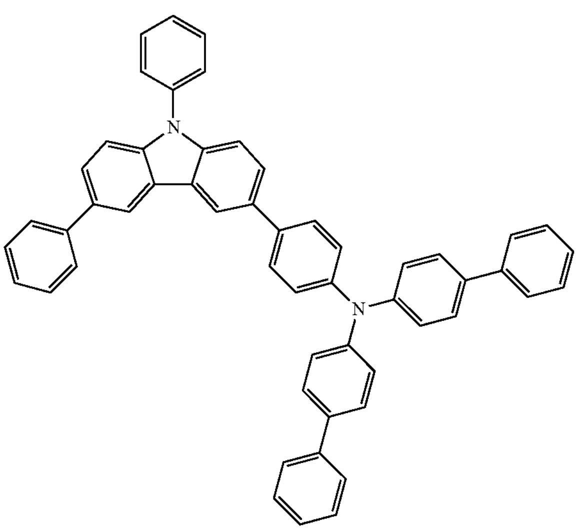

-continued

Z-4

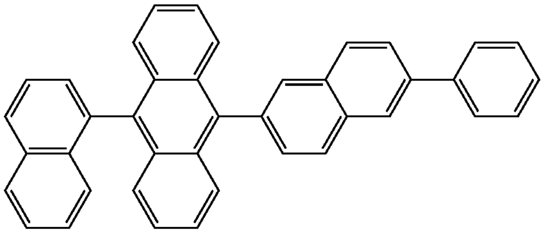

Z-5

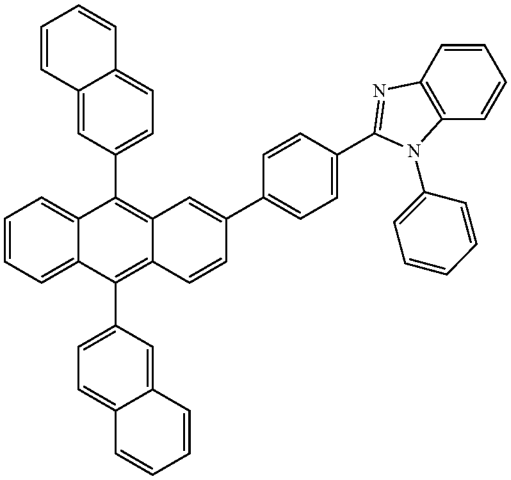

Examples 2 to 6

An organic light emitting device was manufactured in the same manner as in Example 1, except that the compounds shown in Table 1 below were used instead of Compound 1.

Comparative Examples 1 and 2

An organic light emitting device was manufactured in the same manner as in Example 1, except that Compound A or B was used instead of Compound 1. Compound A and B are as follows.

A

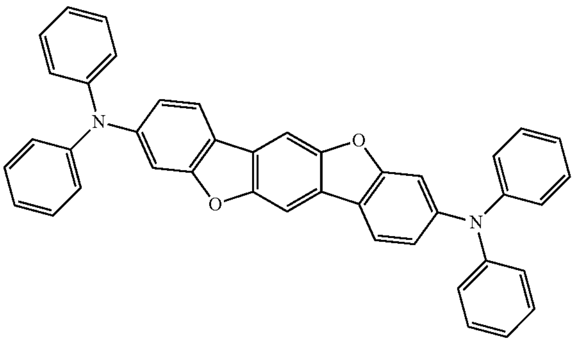

-continued

B

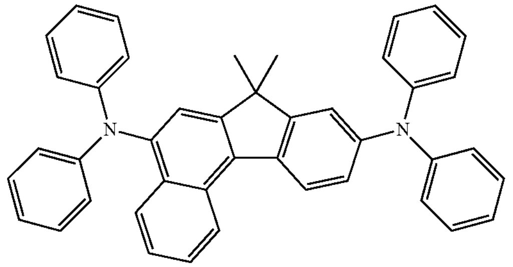

Experimental Example 1: Characteristic Evaluation of Organic Light Emitting Devices Driving voltage, luminous efficiency, quantum efficiency, and lifetime (T95) values of the organic light emitting devices manufactured in Examples 1 to 6 and Comparative Examples 1 and 2 were measured at a current density of 10 $mA/cm^2$, and the results are shown in Table 1 below. The lifetime T95 in Table 1 below means the time required for the luminance to be reduced to 95% of the initial luminance.

TABLE 1

| | Dopant in Light emitting layer | Driving voltage (V) | Luminous efficiency (cd/A) | Quantum efficiency (%) | T95 (hr) |
|---|---|---|---|---|---|
| Example 1 | Compound 1 | 4.42 | 4.82 | 8.06 | 124 |
| Example 2 | Compound 2 | 4.40 | 4.49 | 7.29 | 95 |
| Example 3 | Compound 3 | 4.40 | 4.68 | 7.69 | 116 |
| Example 4 | Compound 4 | 4.39 | 4.85 | 8.10 | 113 |
| Example 5 | Compound 5 | 4.44 | 4.43 | 7.17 | 102 |
| Example 6 | Compound 6 | 4.38 | 4.76 | 7.91 | 127 |
| Comparative Example 1 | Compound A | 4.50 | 4.04 | 5.20 | 68 |
| Comparative Example 2 | Compound B | 4.72 | 2.73 | 4.69 | 39 |

From the above experimental results, it was confirmed that the compound of one embodiment of the present disclosure can be used as a dopant in the light emitting layer of an organic light emitting device and can be used in a solution process at the time of manufacturing the device.

In addition, as shown in Table 1, it was confirmed that the organic light emitting device using the compound of Chemical Formula 1 of the present disclosure as a dopant in the light emitting layer exhibits very excellent properties in terms of luminous efficiency, quantum efficiency and lifetime as compared with when Compound A or B having different parent nuclei is used as a dopant in an organic light emitting device.

Experimental Example 2: Measurement of the Full Width at Half Maximum of Compound The photoluminescence (PL) spectra of the previously prepared Compounds 1 to 6 and Compounds A to B were measured, and the full width at half maximum (FWHM) is shown in Table 2 below. The full width at half maximum (FWHM) means the width between two wavelength values that represents half of the maximum intensity value. Generally, the smaller the value, the higher the luminous efficiency. Each compound was dissolved in toluene at a concentration of $10^{-5}$ M, and measured using an excitation wavelength of 380 nm.

TABLE 2

| Compound | full width at half maximum (nm) |
|---|---|
| Compound 1 | 29 |
| Compound 2 | 31 |
| Compound 3 | 30 |
| Compound 4 | 29 |
| Compound 5 | 33 |
| Compound 6 | 31 |
| Compound A | 38 |
| Compound B | 44 |

As shown in Table 2, it was confirmed that the compound of Chemical Formula 1 of the present disclosure has a smaller full width at half maximum than that of Compounds A or B having different parent nuclei. Therefore, it is estimated that the luminous efficiency of the compound of the present disclosure represented by Chemical Formula 1 is more excellent.

DESCRIPTION OF SYMBOLS

| [Description of symbols] | |
|---|---|
| 1: substrate | 2: anode |
| 3: light emitting layer | 4: cathode |
| 5: hole injection layer | 6: hole transport layer |
| 7: electron transport layer | 8: electron injection layer |

The invention claimed is:

1. A compound represented by the following Chemical Formula 1:

[Chemical Formula 1]

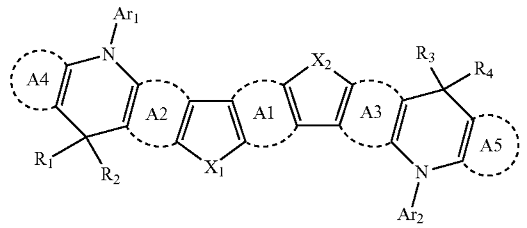

in Chemical Formula 1, $X_1$ and $X_2$ are each independently O, S, Se, or Te;

A1 to A3 are each independently a substituted or unsubstituted $C_{6-60}$ aromatic ring fused with two adjacent rings, A4 and A5 are each independently a substituted or unsubstituted $C_{6-60}$ aromatic ring fused with one adjacent ring, $Ar_1$ and $Ar_2$ are each independently a substituted or unsubstituted $C_{6-60}$ aryl; or a substituted or unsubstituted $C_{2-60}$ heteroaryl containing at least one selected from the group consisting of Si N, O and S, and $R_1$ to $R_4$ are each independently hydrogen; deuterium; halogen; a substituted or unsubstituted $C_{1-60}$ alkyl; a substituted or unsubstituted $C_{3-60}$ cycloalkyl; a substituted or unsubstituted $C_{6-60}$ aryl; or a substituted or unsubstituted $C_{2-60}$ heteroaryl containing at least one selected from the group consisting of N, O and S.

2. The compound of claim 1, wherein:
the Chemical Formula 1 is represented by any one of the following Chemical Formulas 1-1 to 1-17:
1-1
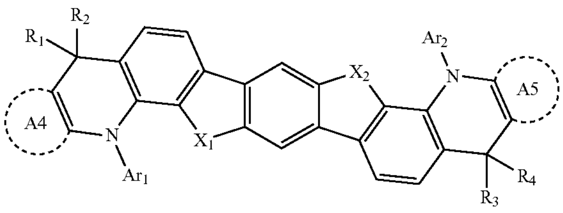
1-2
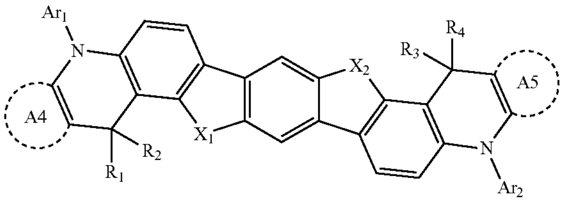
1-3
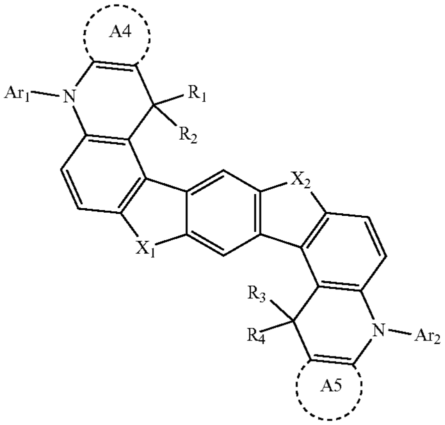
1-4
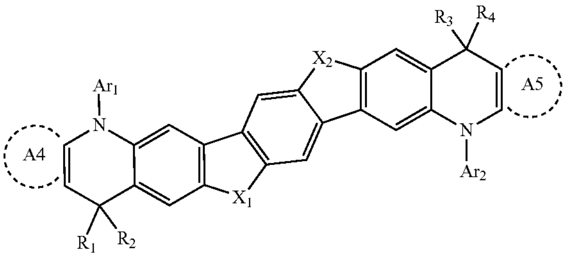
1-5
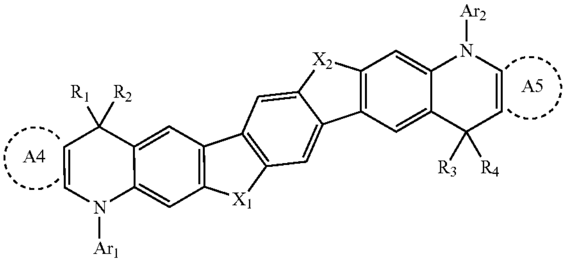
-continued
1-6
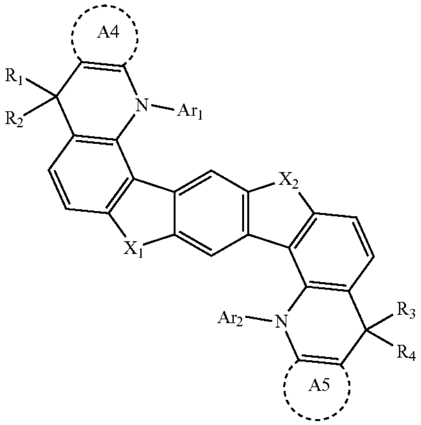
1-7
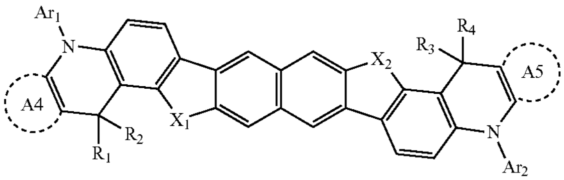
1-8
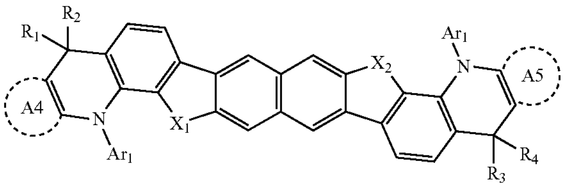
1-9
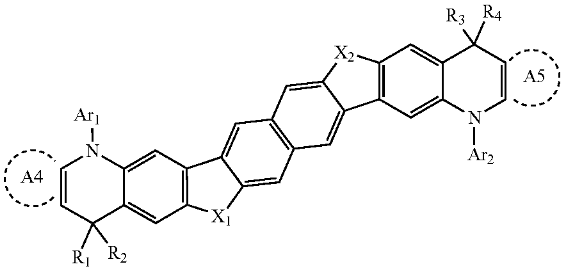
1-10
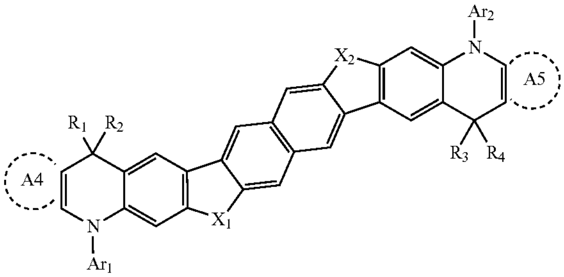

-continued
1-11
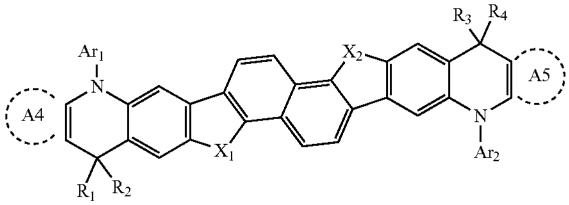
1-12
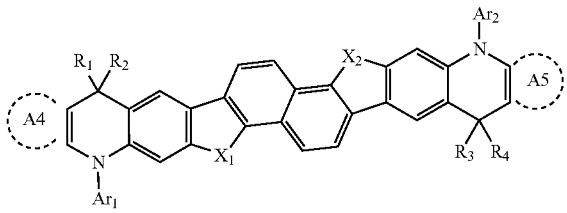
1-13
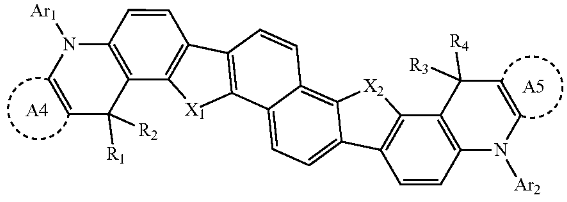
1-14
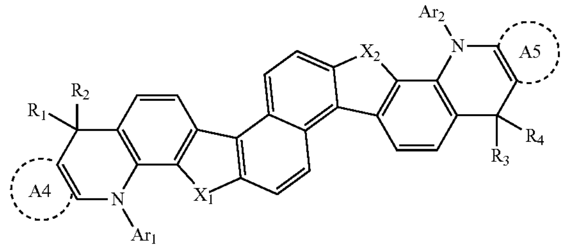
-continued
1-15
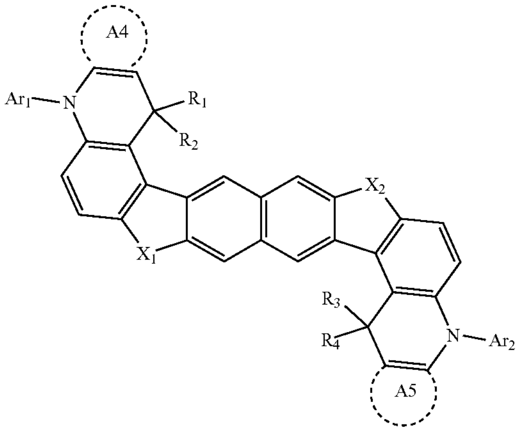
1-16
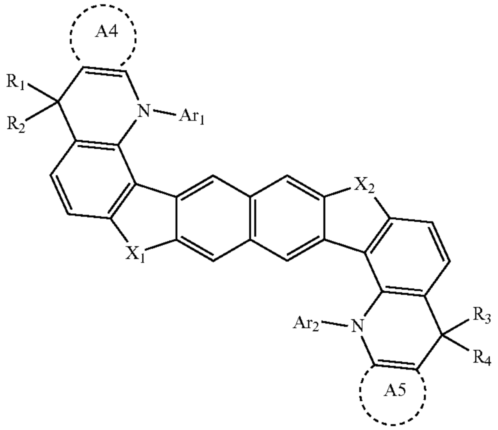
1-17
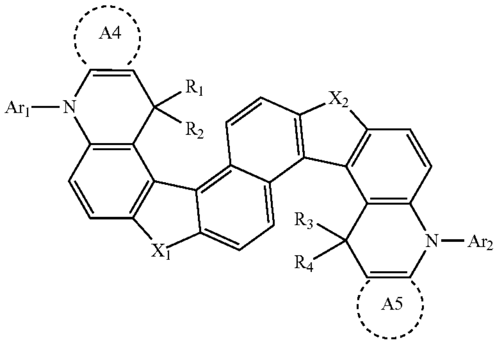
in Chemical Formula 1-1 to Chemical Formula 1-17, $X_1$, $X_2$, A4, A5, $Ar_1$, $Ar_2$, and $R_1$ to $R_4$ are as defined in claim 1.

3. The compound of claim 1, wherein:
the Chemical Formula 1 is represented by any one of the following Chemical Formulas 1-A to 1-F:
[Chemical Formula 1-A]
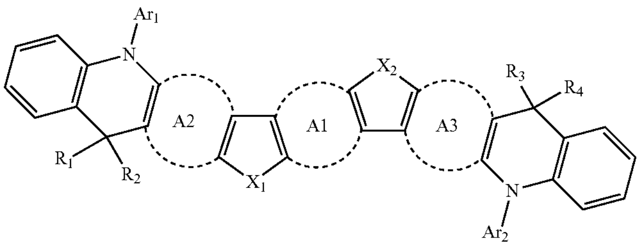
[Chemical Formula 1-B]
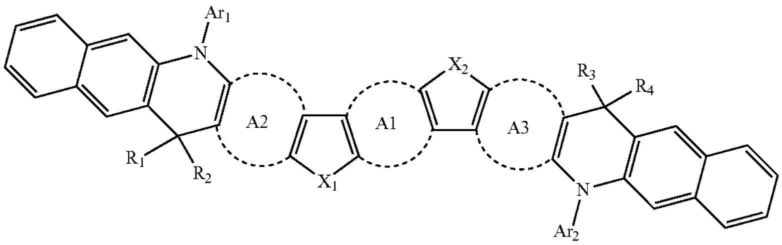
[Chemical Formula 1-C]
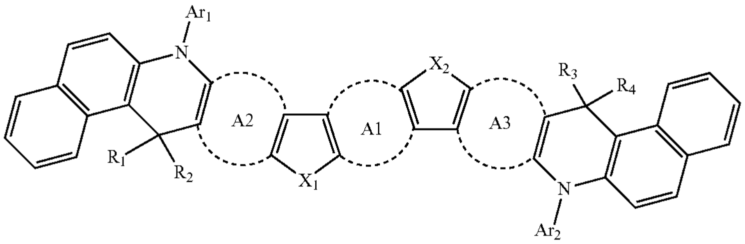
[Chemical Formula 1-D]
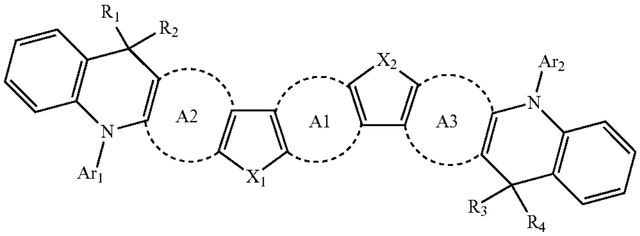
[Chemical Formula 1-E]
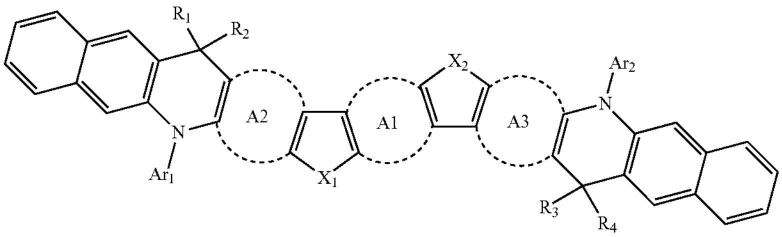

-continued

[Chemical Formula 1-F]

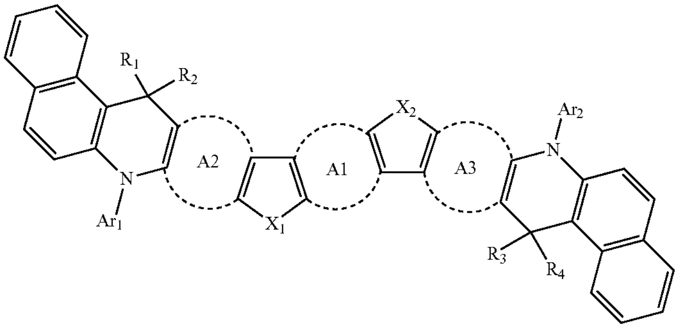

in Chemical Formula 1-A to Chemical Formula 1-F, $X_1$, $X_2$, A1 to A3, $Ar_1$, $Ar_2$, and $R_1$ to $R_4$ are as defined in claim 1.

4. The compound of claim 1, wherein:

the Chemical Formula 1 is represented by Chemical Formula 1-A-1, Chemical Formula 1-A-2, or Chemical Formula 1-B-1:

[Chemical Formula 1-A-1]

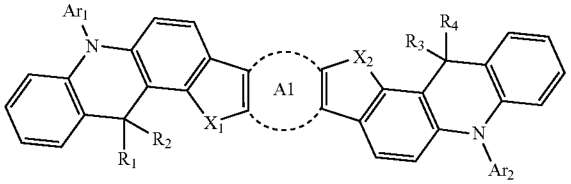

[Chemical Formula 1-A-2]

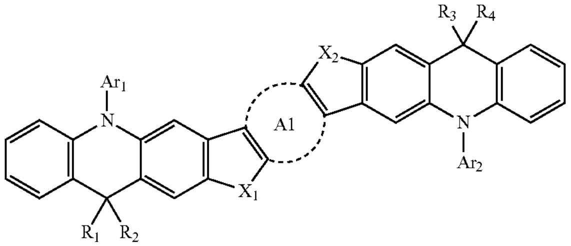

[Chemcial Formula 1-B-1]

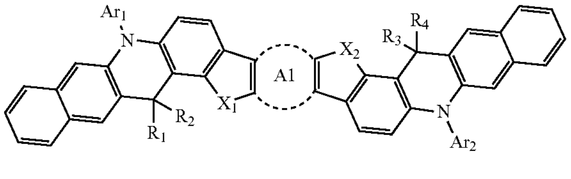

in Chemical Formula 1-A-1, Chemical Formula 1-A-2 and Chemical Formula 1-B-1, A1 is a benzene ring or a naphthalene ring fused with two adjacent rings, and $X_1$, $X_2$, $Ar_1$, $Ar_2$, and $R_1$ to $R_4$ are as defined in claim 1.

5. The compound of claim 1, wherein:

$X_1$ and $X_2$ are each independently O, S, or Se.

6. The compound of claim 1, wherein:

A1 to A3 are each independently a benzene ring or a naphthalene ring fused with two adjacent rings, and A4 and A5 are each independently a benzene ring or a naphthalene ring fused with one adjacent ring.

7. The compound of claim 1, wherein:

A2 and A3 are identical to each other, and A4 and A5 are identical to each other.

8. The compound of claim 1, wherein:

$Ar_1$ and $Ar_2$ are each independently phenyl, biphenylyl, naphthyl, dimethylfluorenyl, dimethyl dibenzosilolyl, dimethyl benzofluorenyl, benzofuranyl, benzothiophenyl, dibenzofuranyl, dibenzothiophenyl, or pyridinyl, and the $Ar_1$ and $Ar_2$ are each independently unsubstituted; or substituted with any one or more substituent groups selected from the group consisting of butyl, tert-butyl, trimethylsilyl and triphenylsilyl.

9. The compound of claim 1, wherein:

$Ar_1$ and $Ar_2$ are identical to each other.

10. The compound of claim 1, wherein:

$R_1$ to $R_4$ are each independently hydrogen, deuterium, methyl, or hexyl.

11. The compound of claim 1, wherein:

A2 and A3 are identical to each other, A4 and A5 are identical to each other, $Ar_1$ and $Ar_2$ are identical to each other, $R_1$ and $R_3$ are identical to each other, and $R_2$ and $R_4$ are identical to each other.

12. The compound of claim 1, wherein:

the compound represented by Chemical Formula 1 is any one selected from the group consisting of:

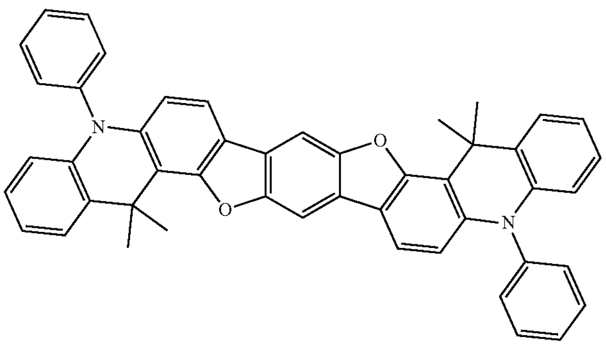
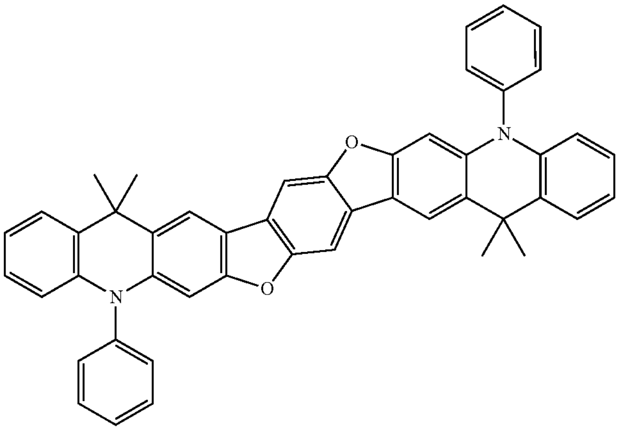
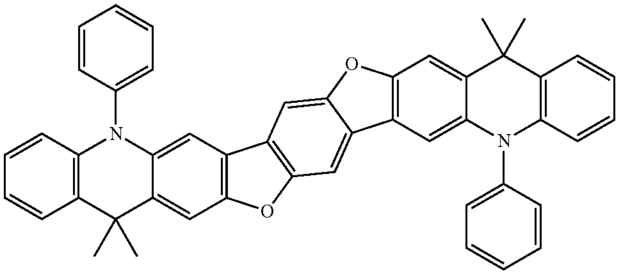
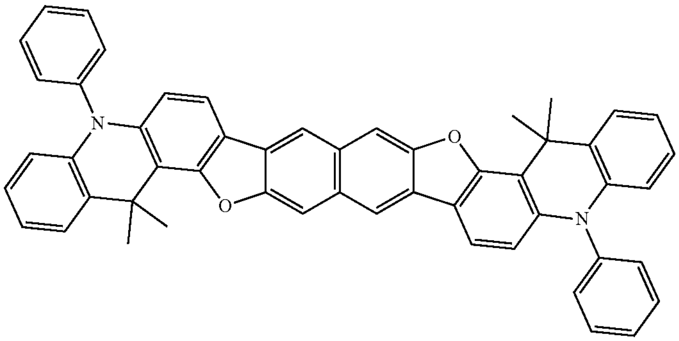

-continued
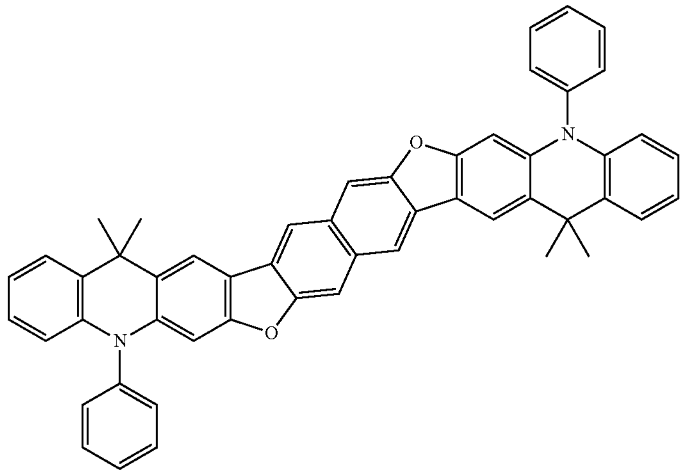
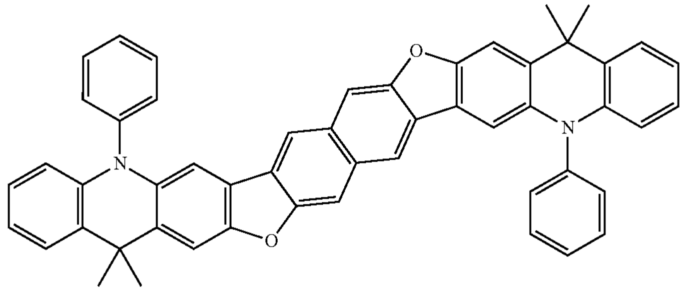
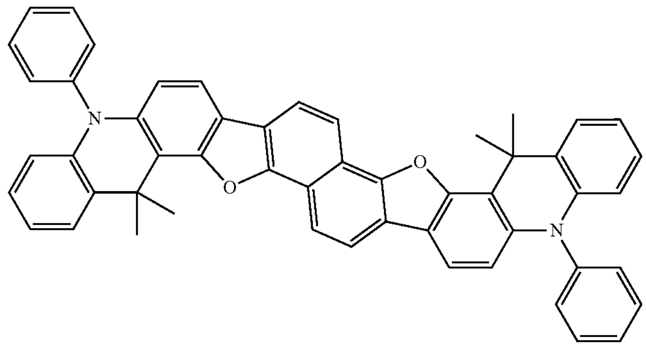
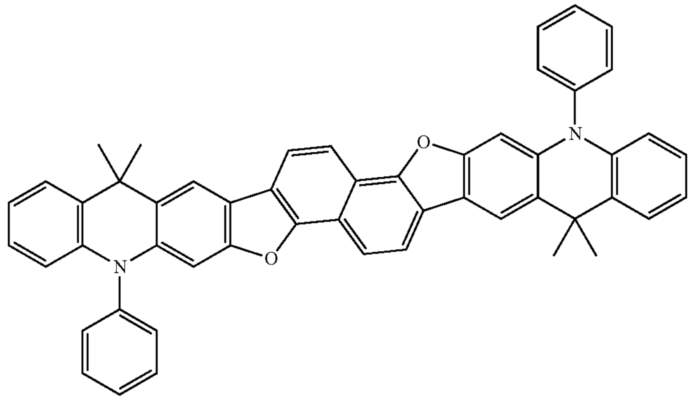

-continued
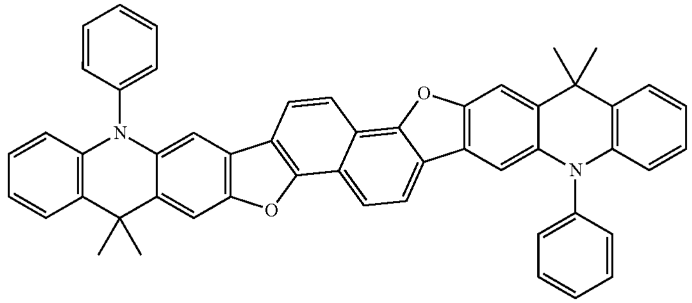
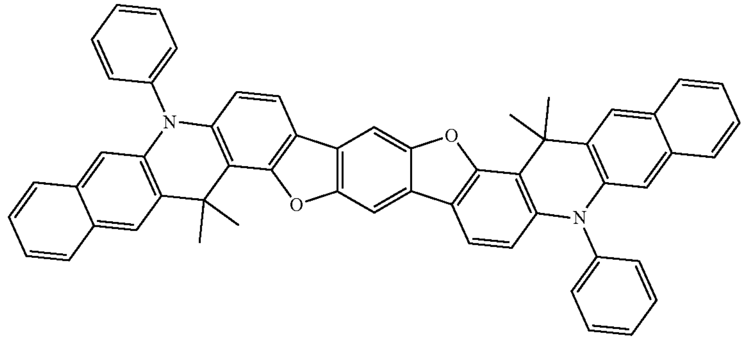
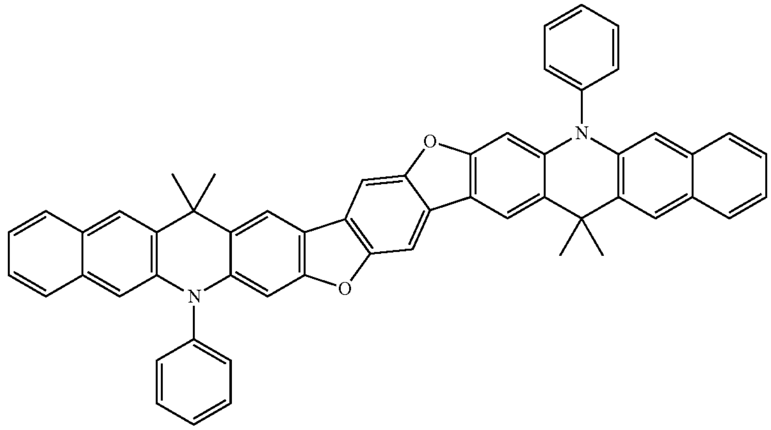
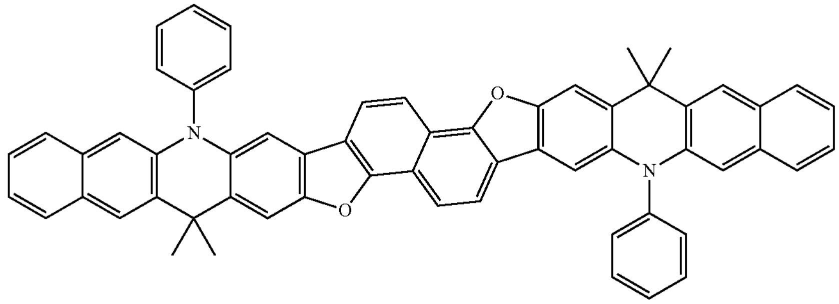
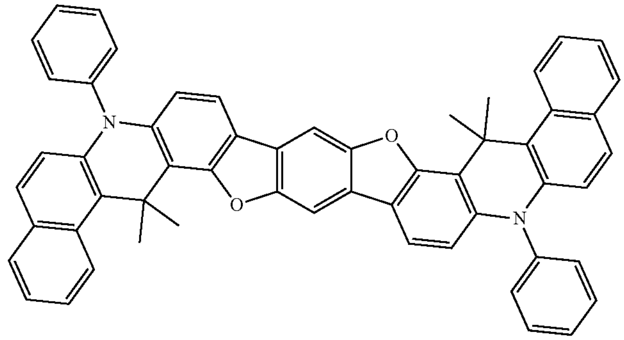

-continued
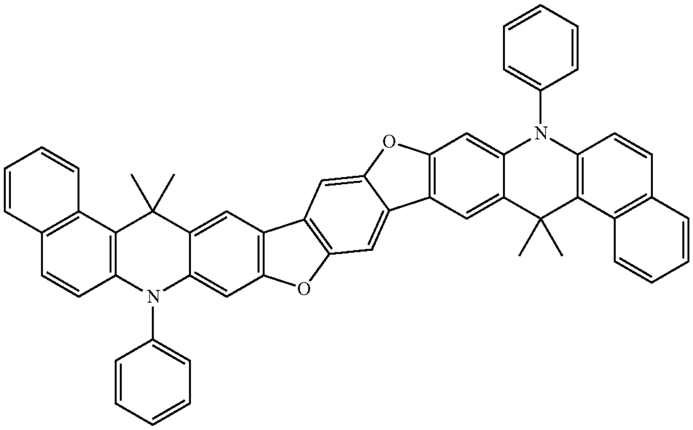 [SMILES: CC1(C)c2cc3c(cc2N(c2ccccc2)c2ccc4ccccc4c21)oc1cc2c(cc13)oc1cc3c(cc12)C(C)(C)c1c(ccc2ccccc12)N3c1ccccc1]
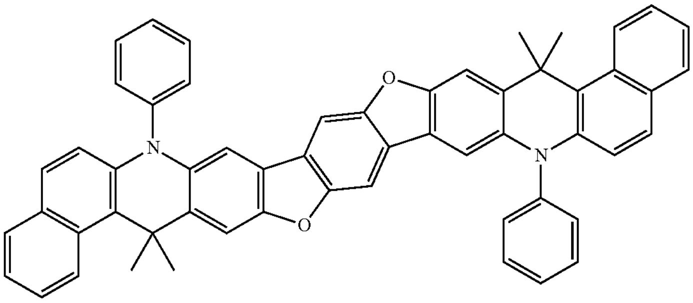
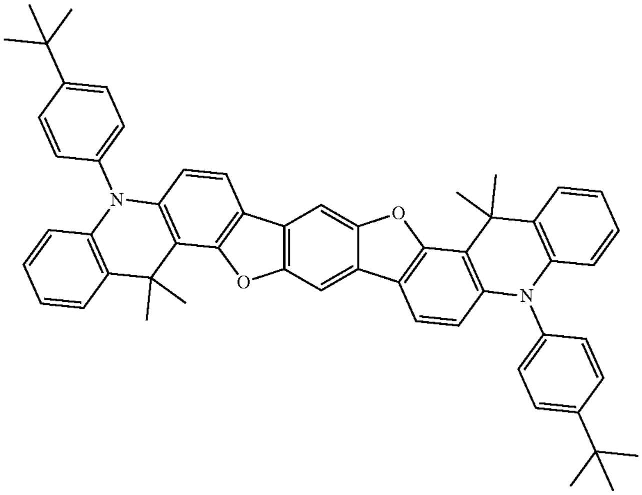
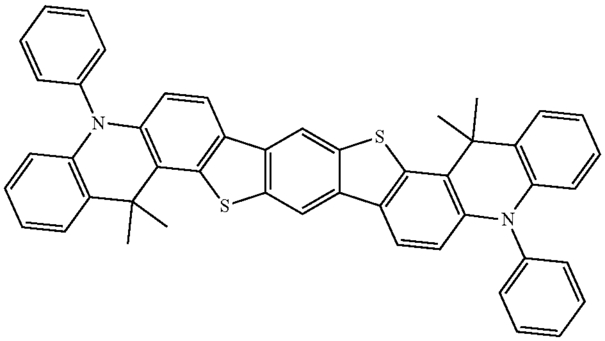

-continued
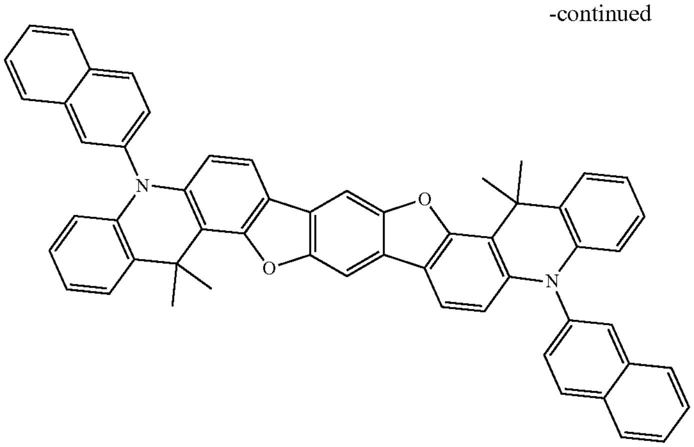
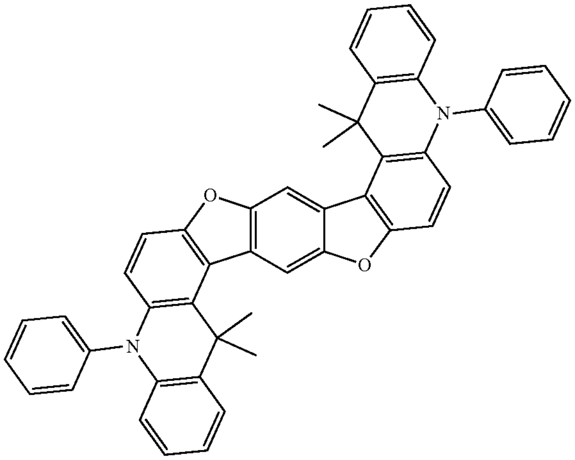
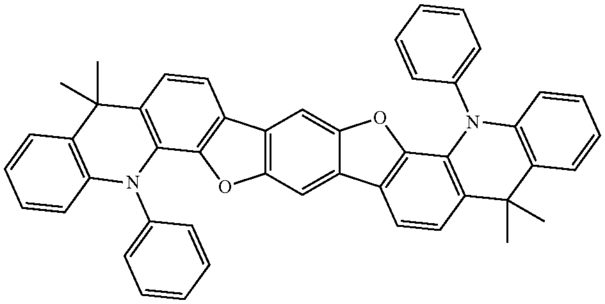
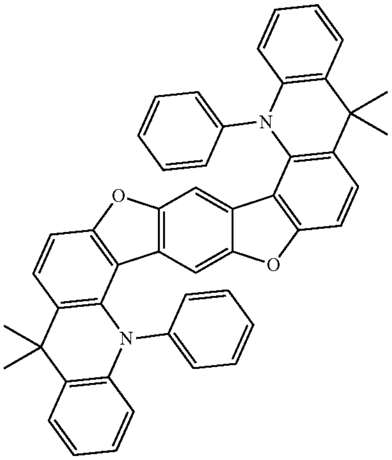

-continued
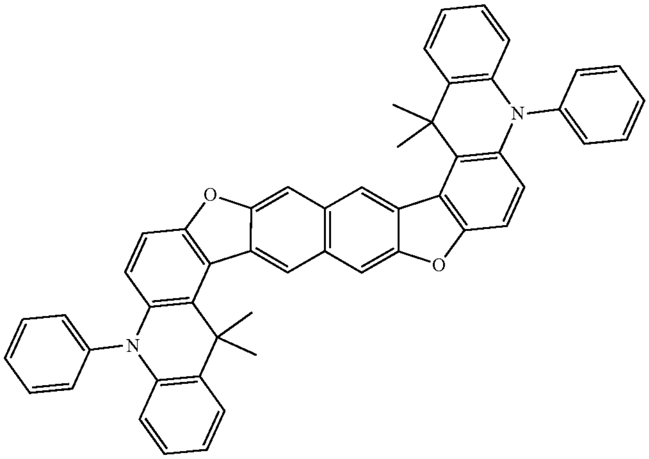
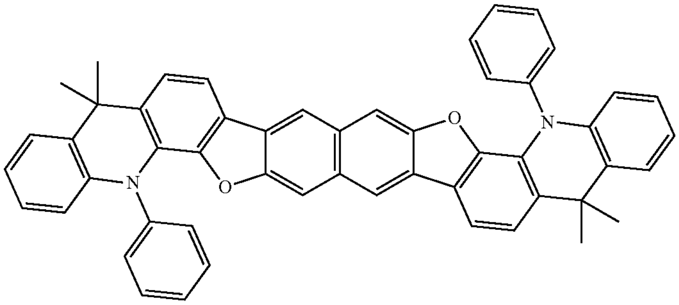
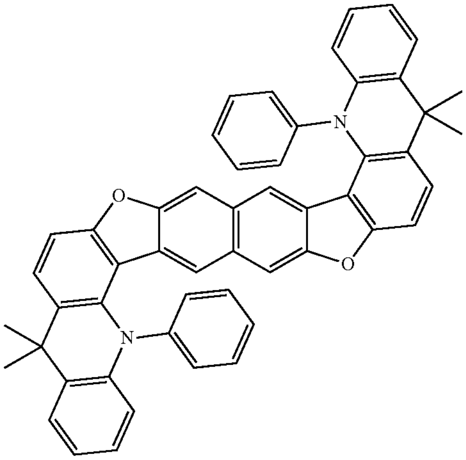
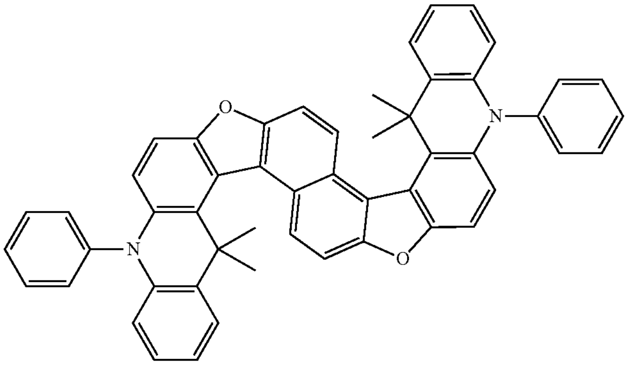
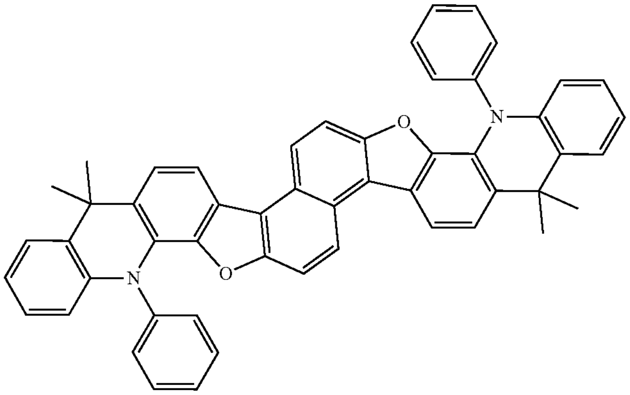

-continued
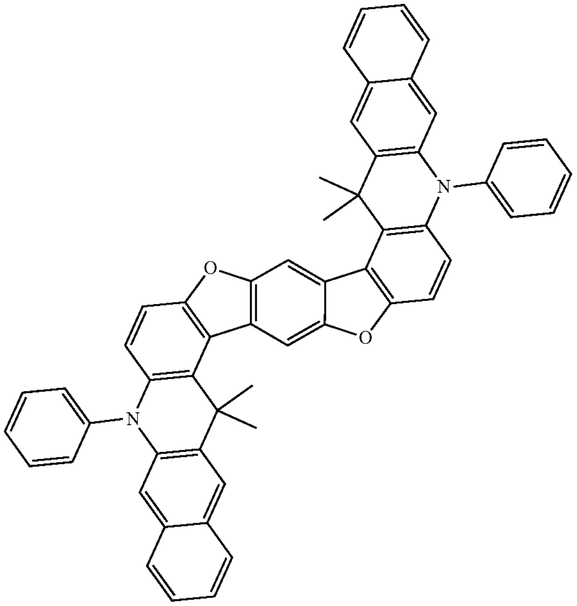
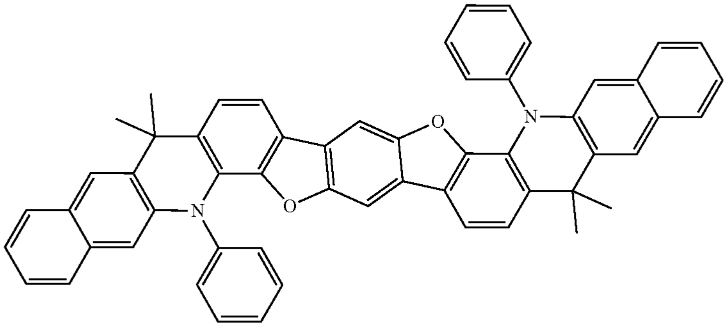
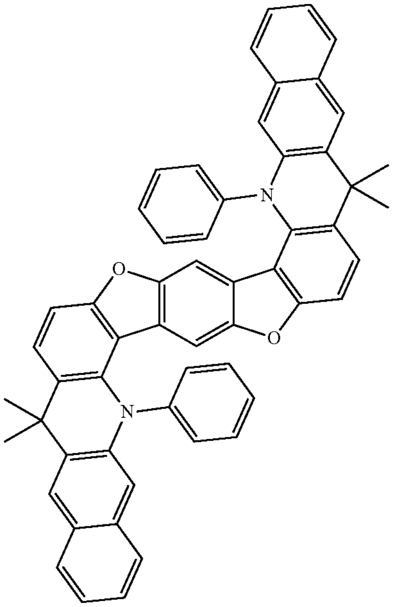

-continued
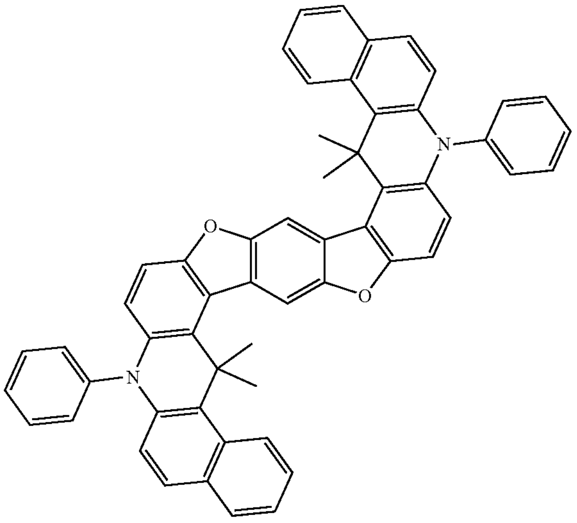
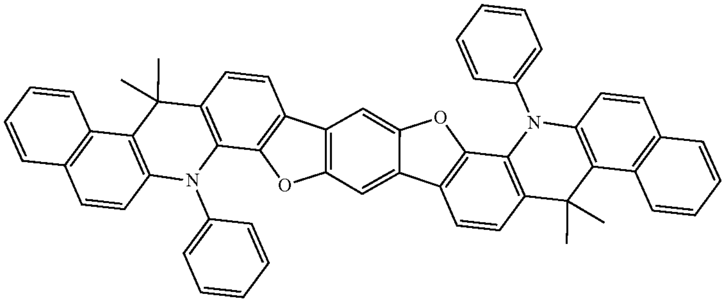
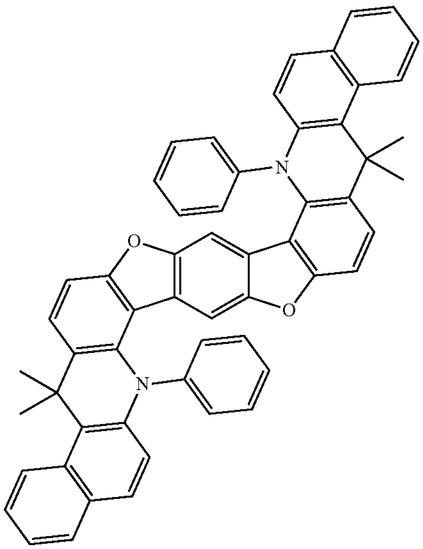

-continued
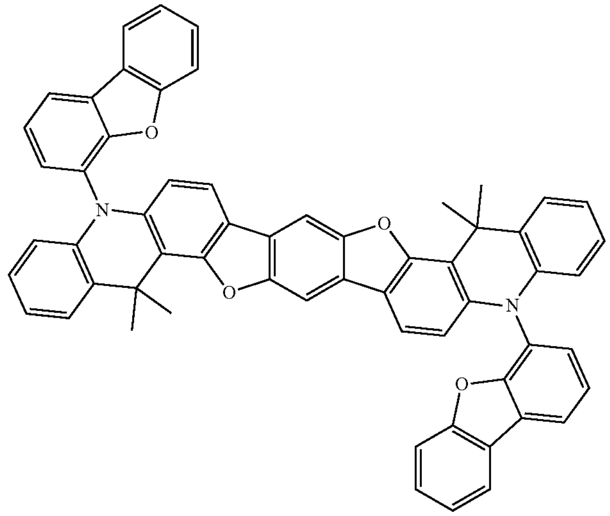
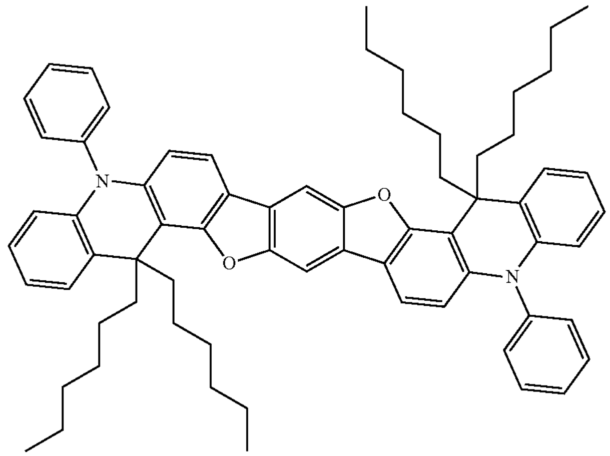
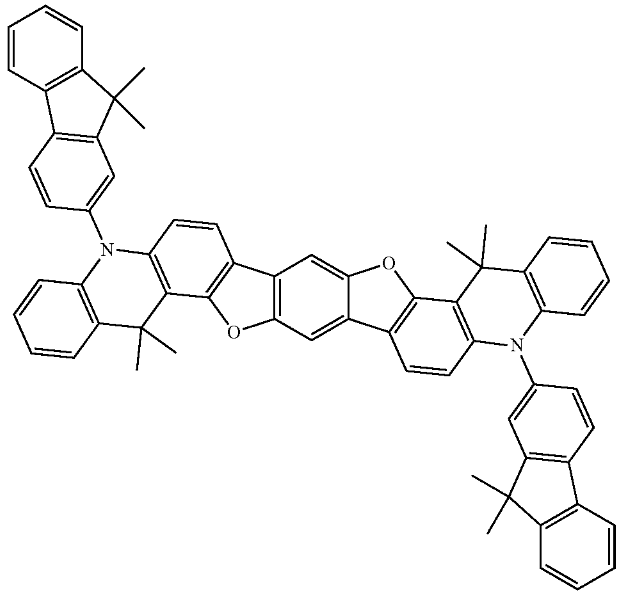

-continued
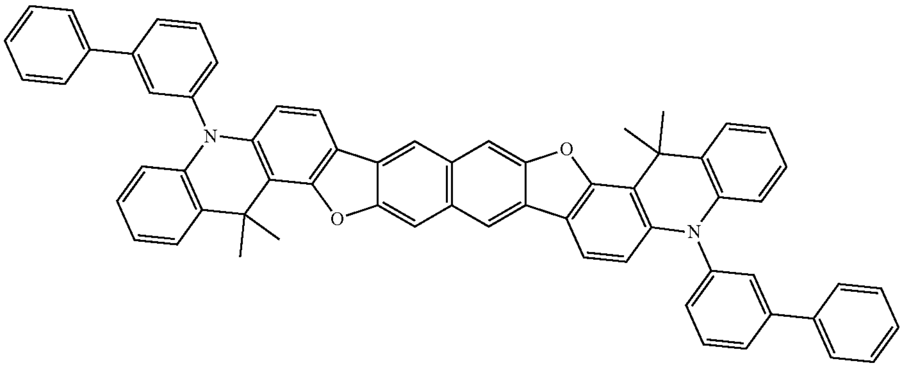
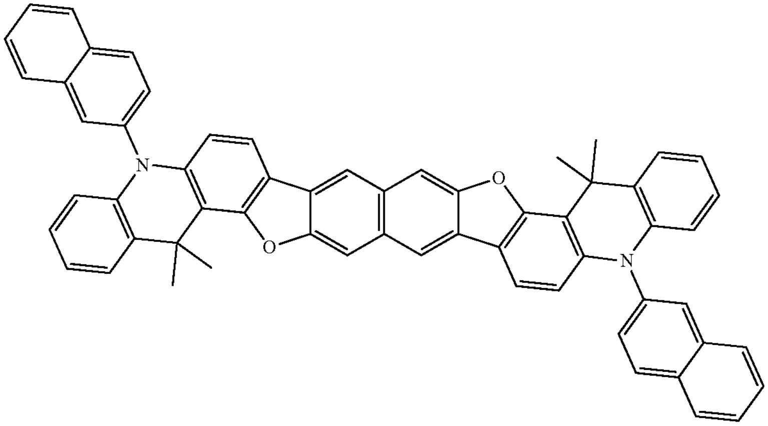
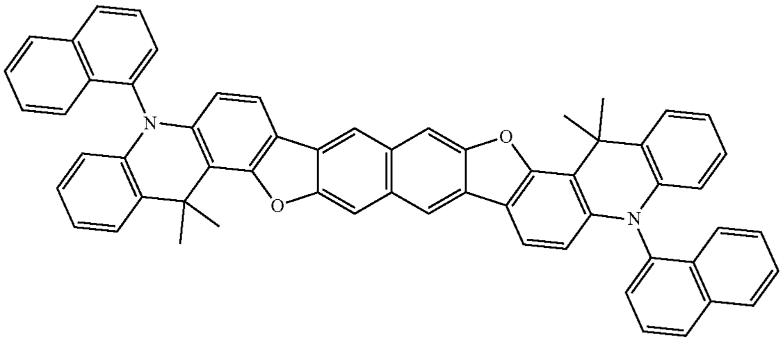
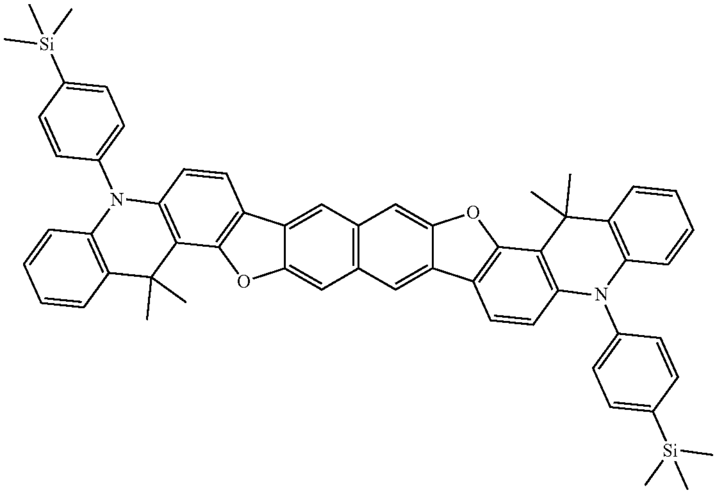

-continued
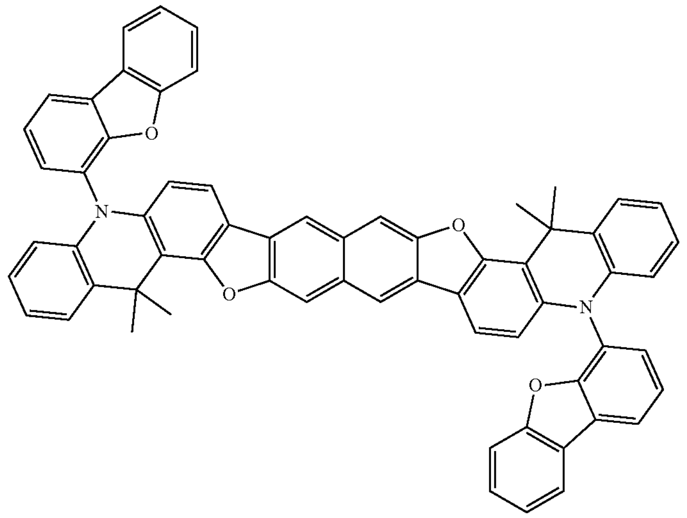
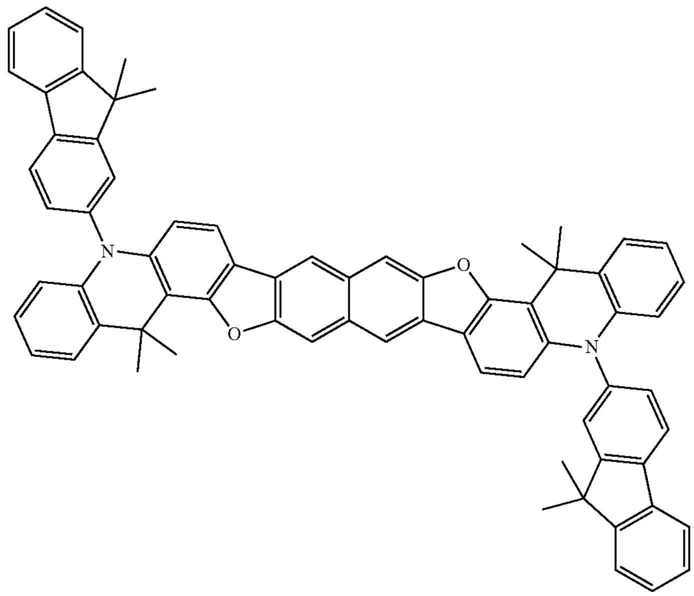
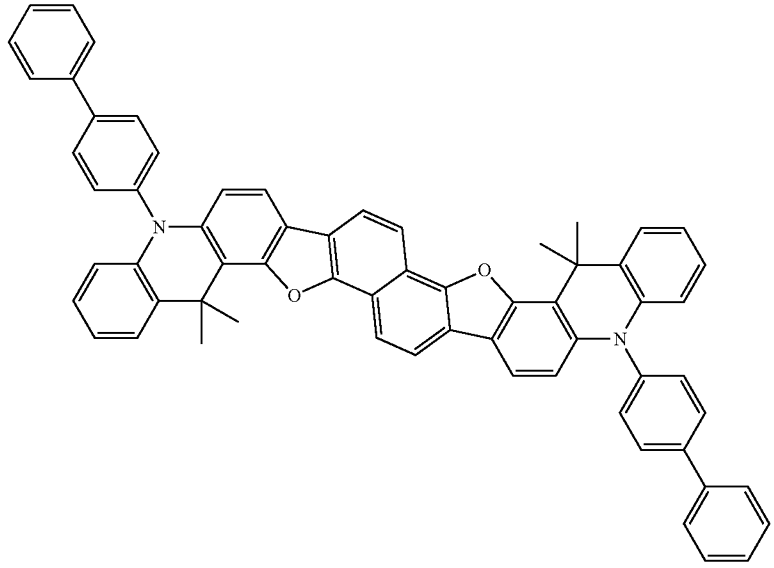

-continued
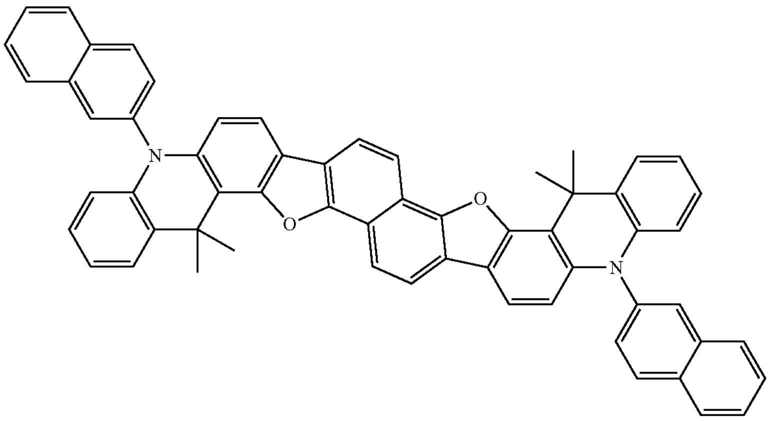
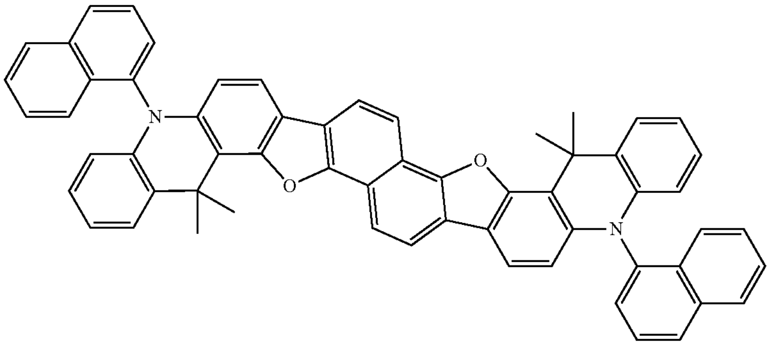
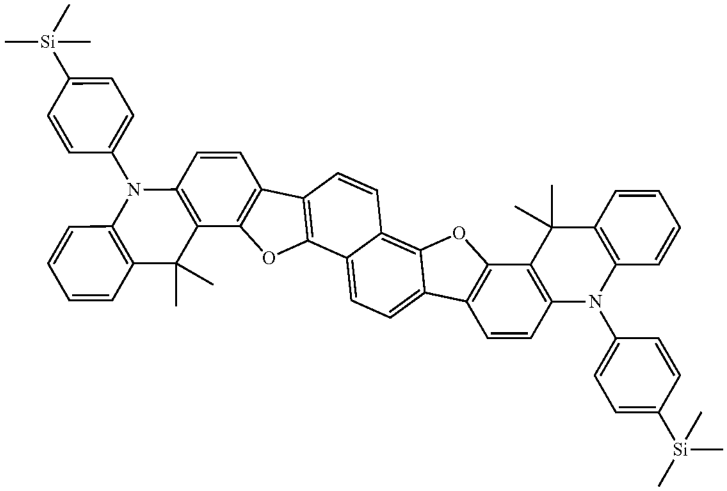

-continued
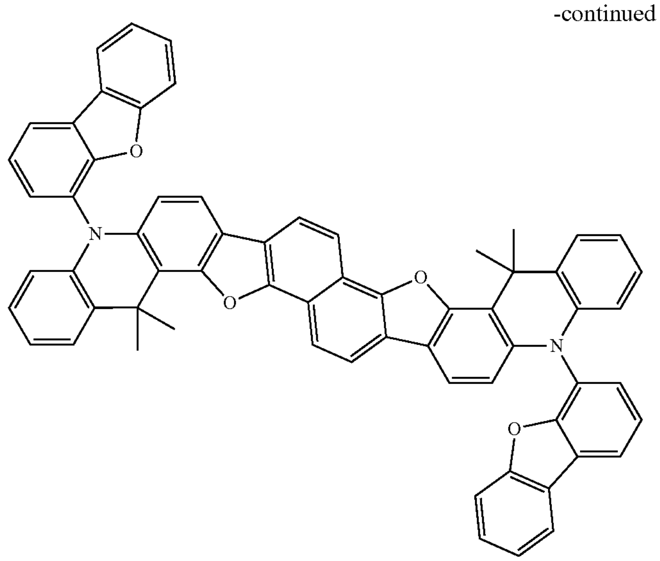
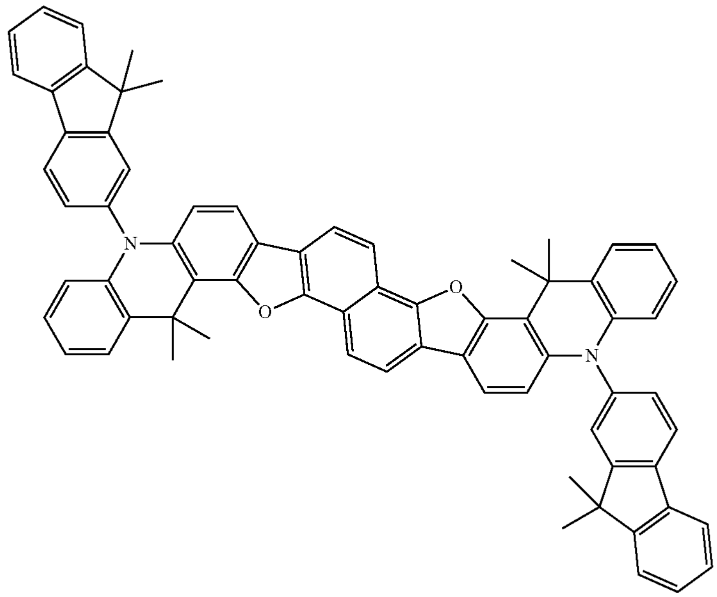
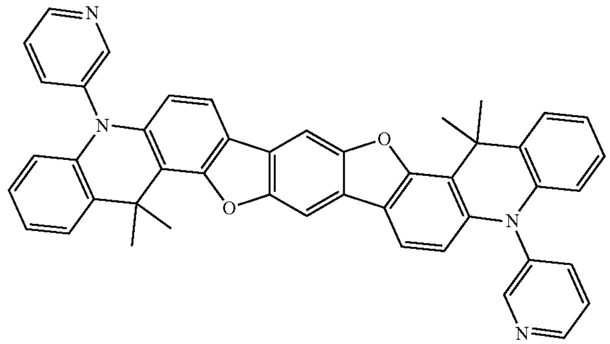

-continued
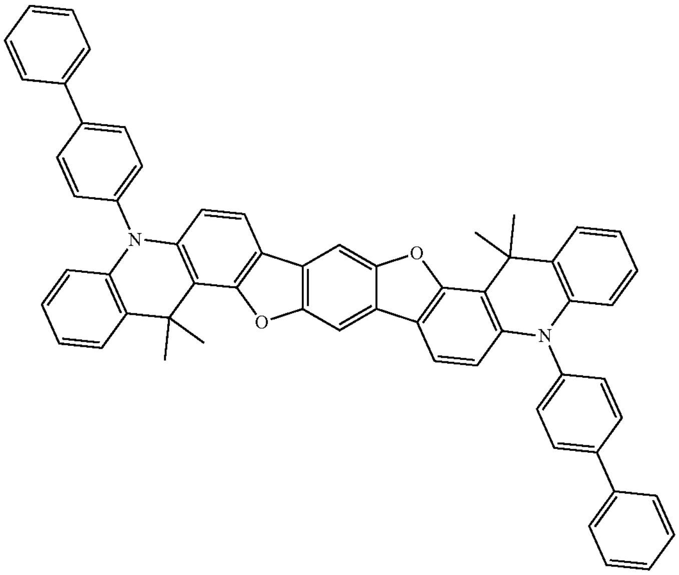
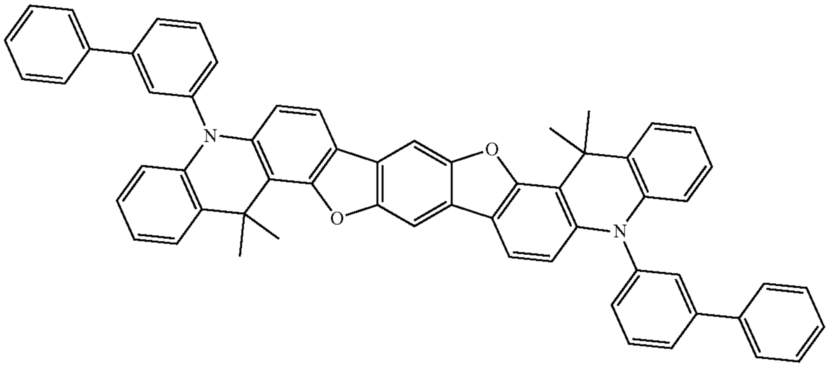
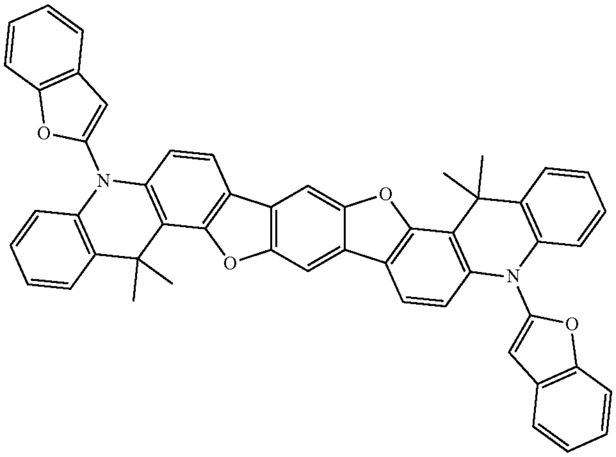

-continued
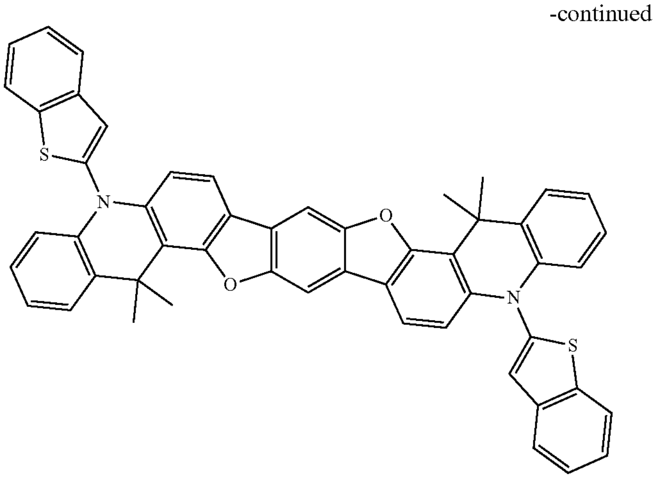
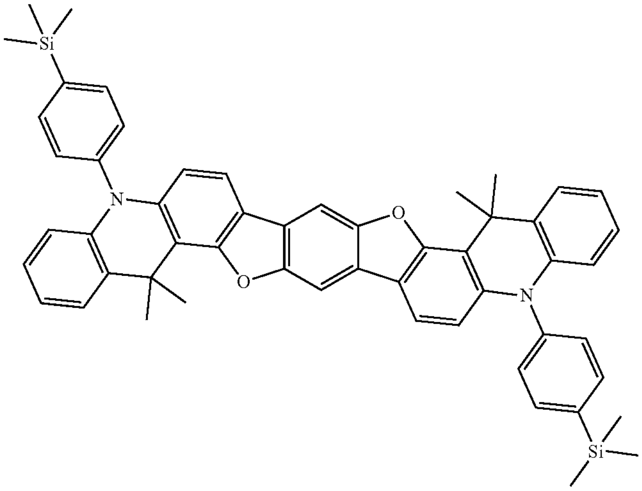
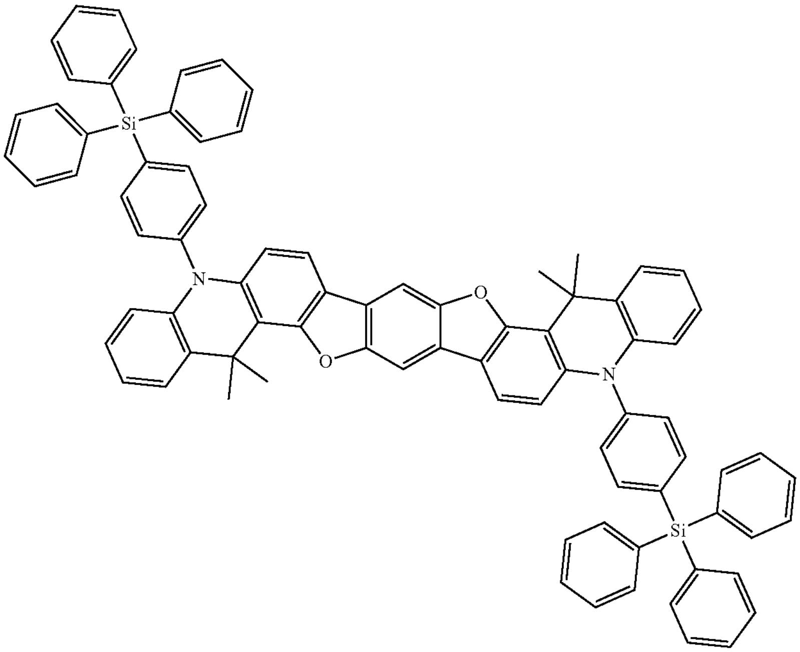

-continued
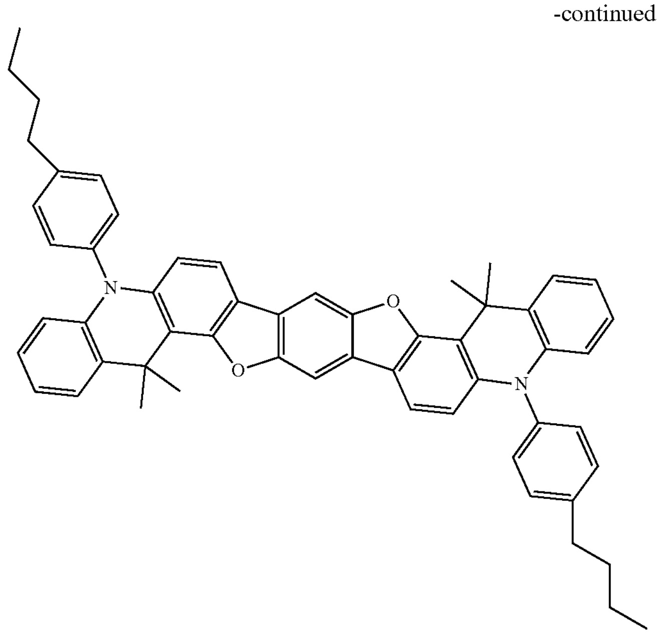
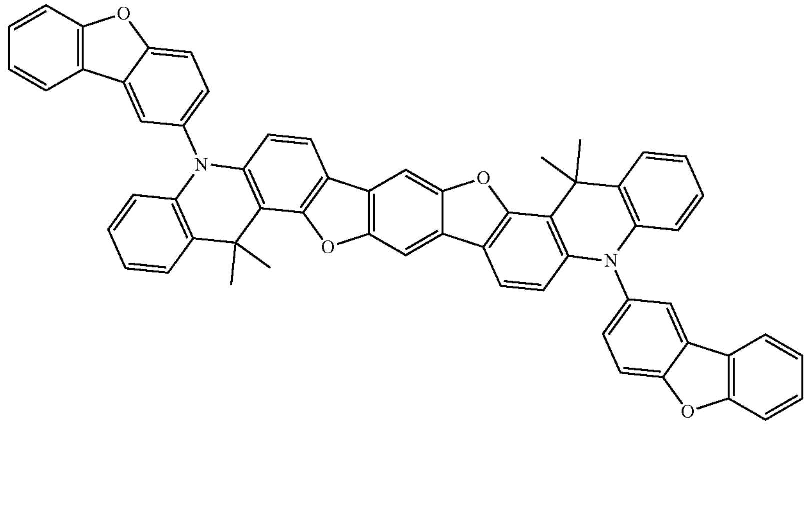
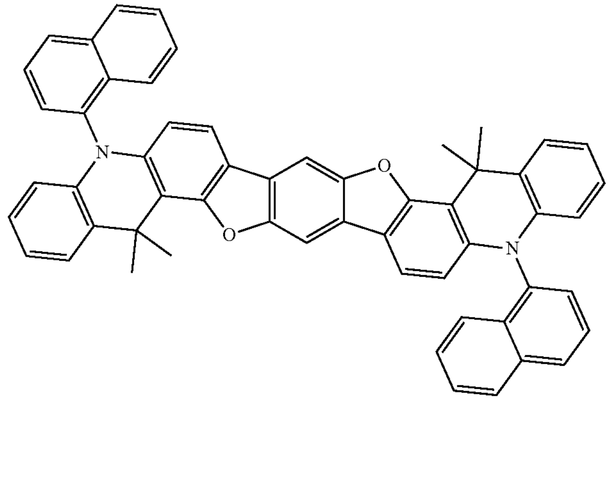

-continued
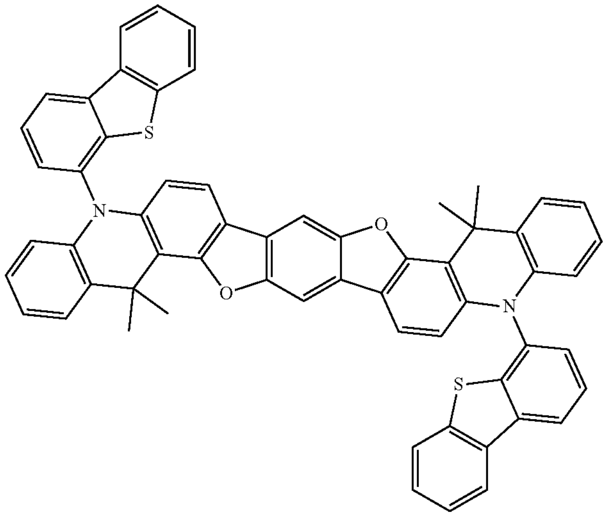
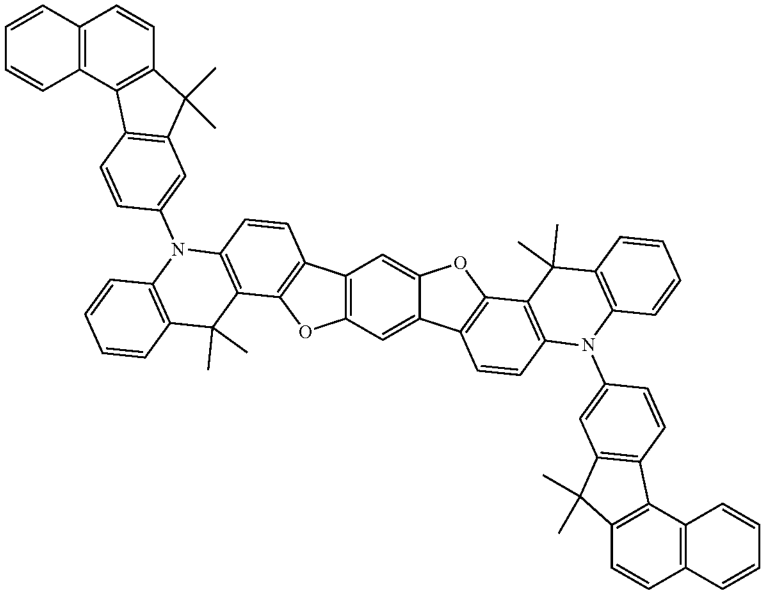
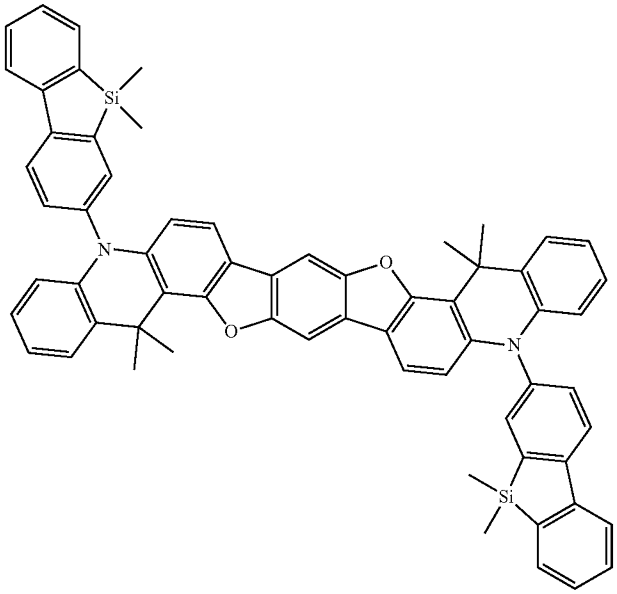

-continued
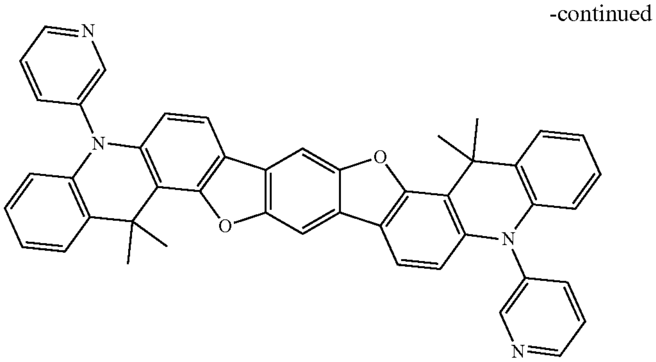
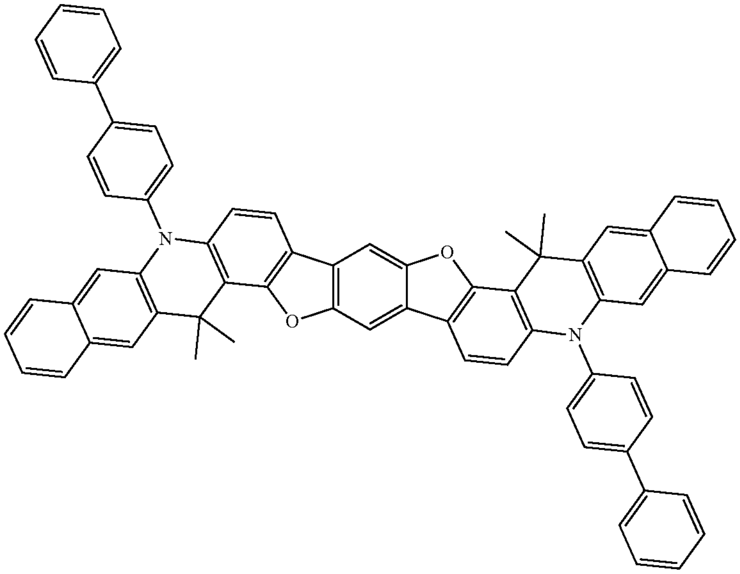
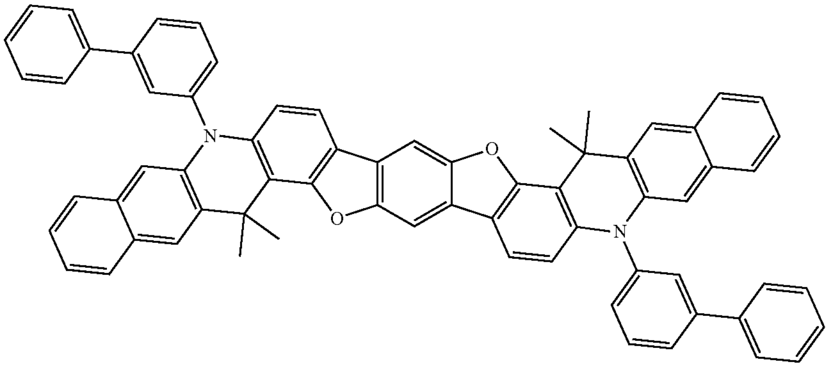
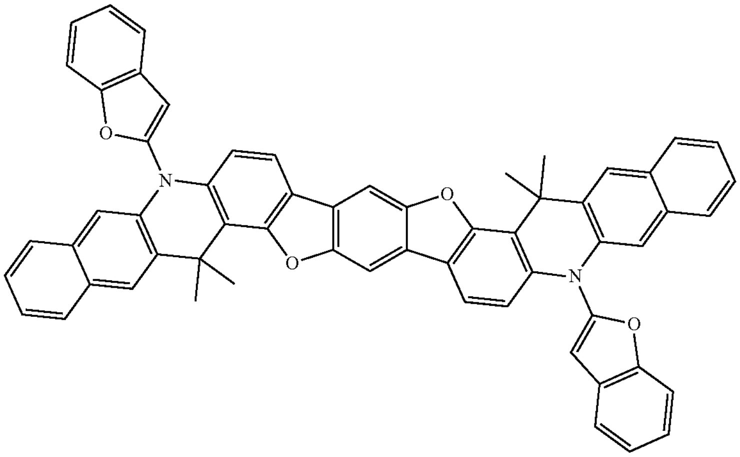

-continued
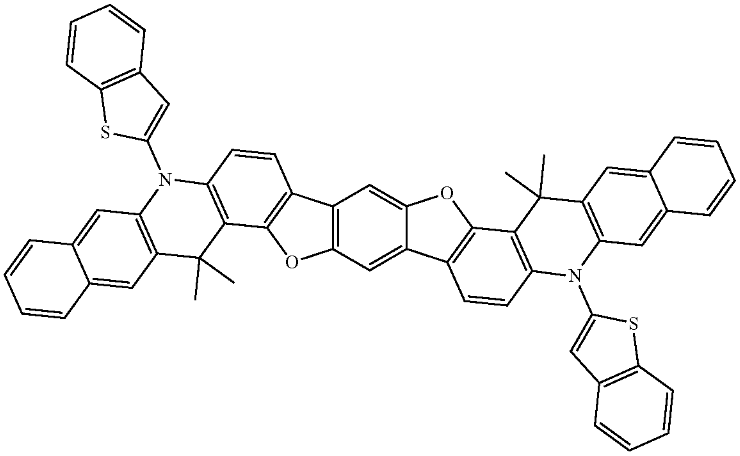
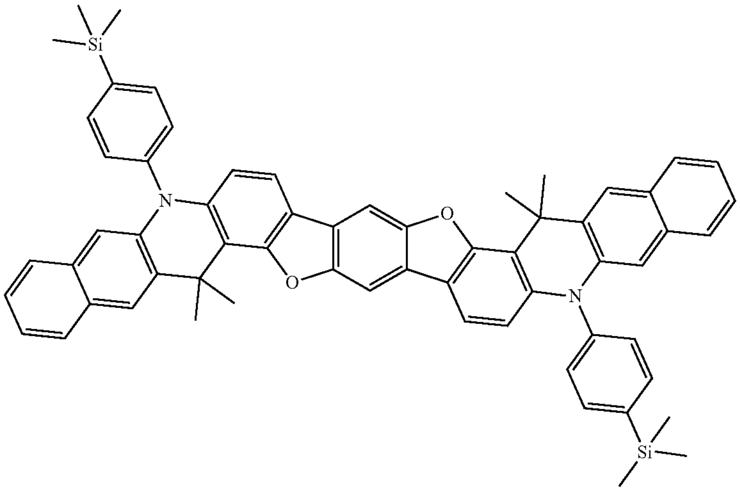
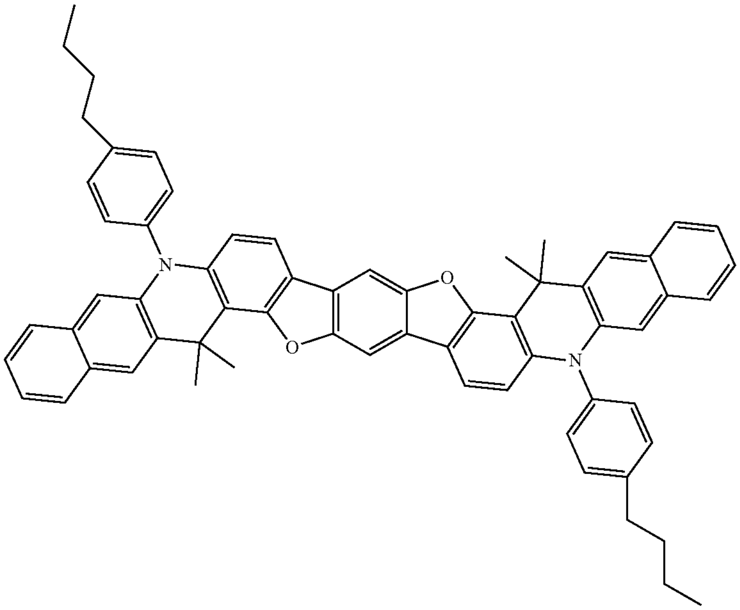

-continued
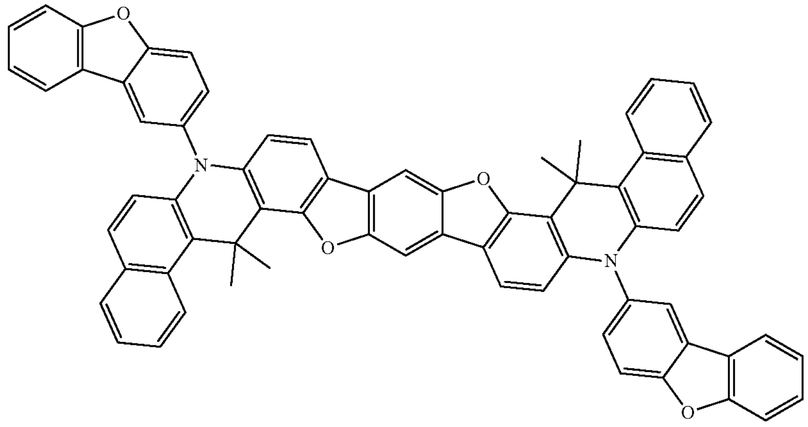
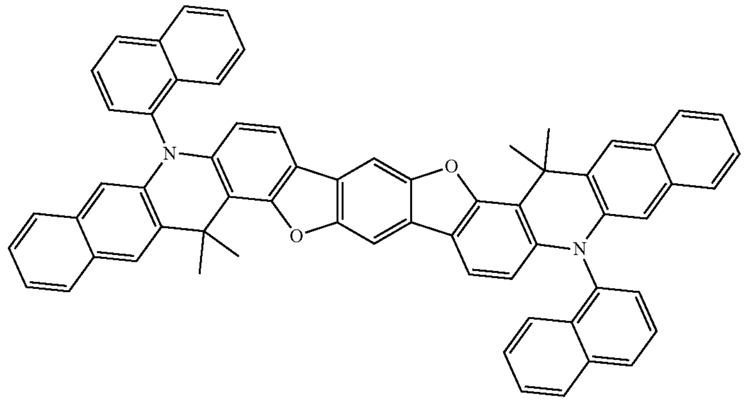
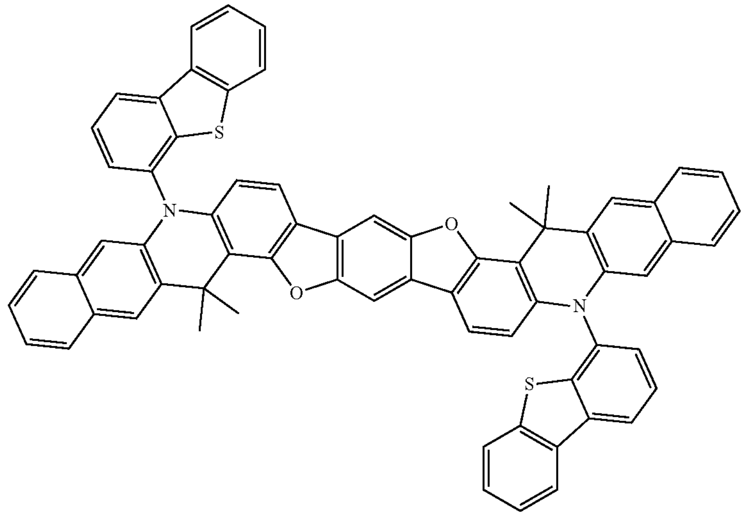

-continued
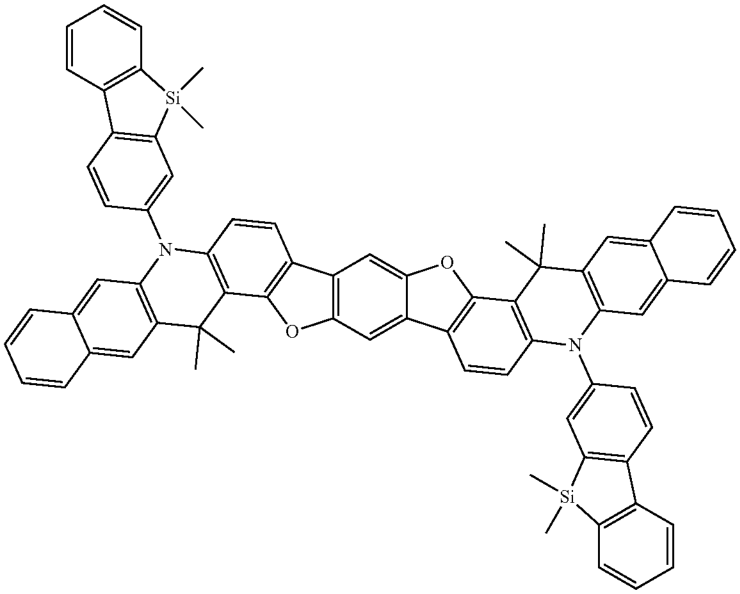
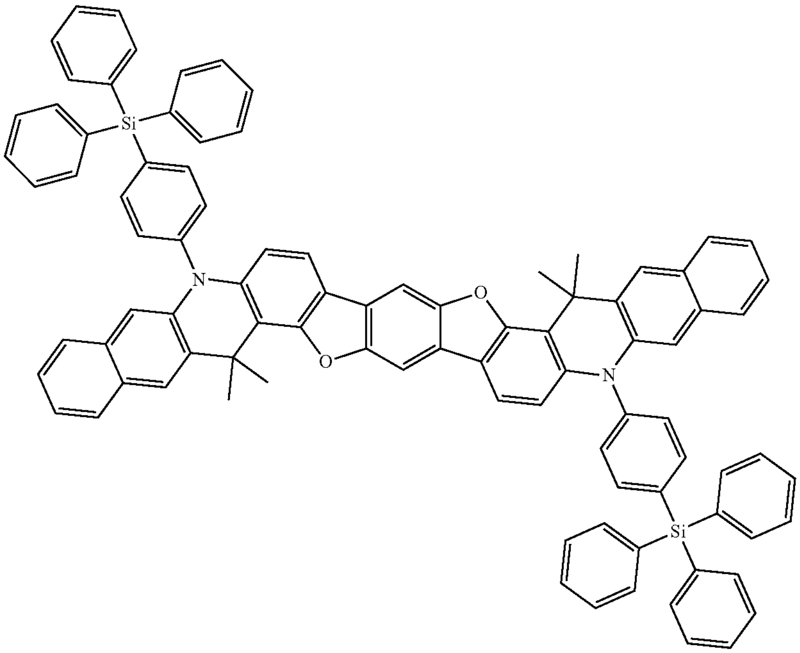
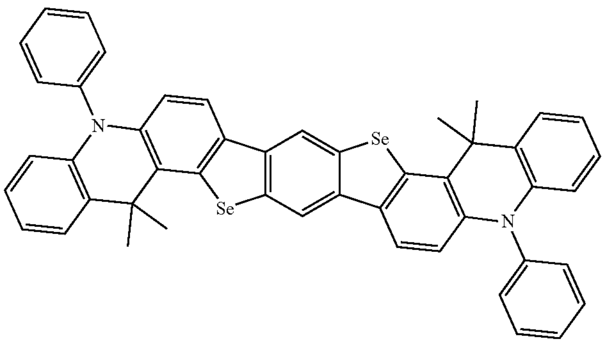

-continued
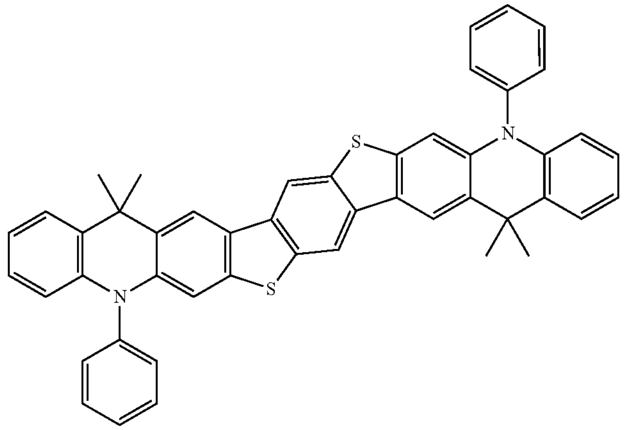
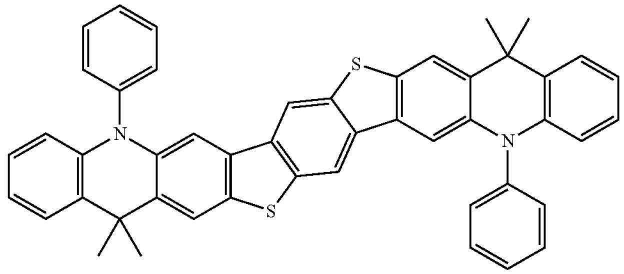
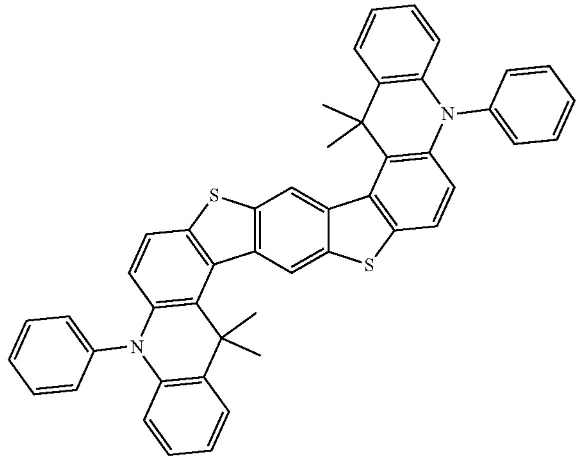
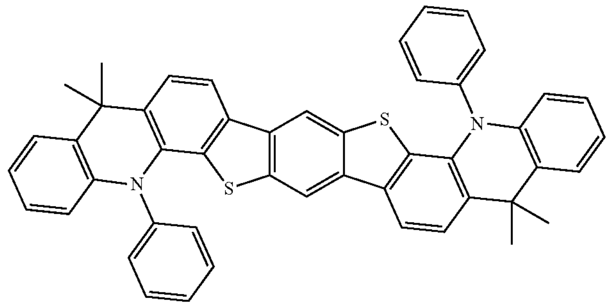

-continued
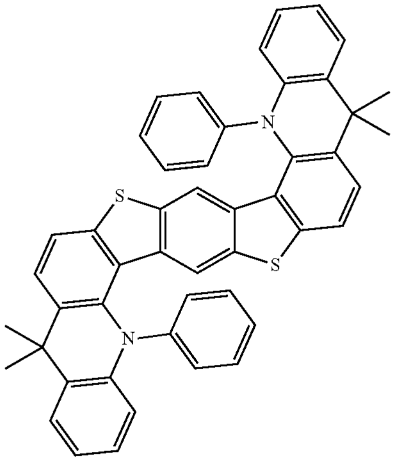
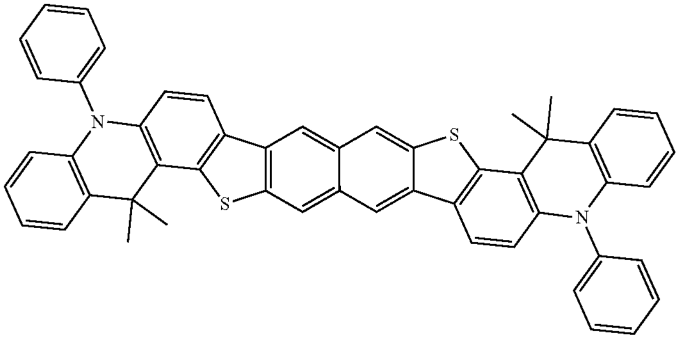
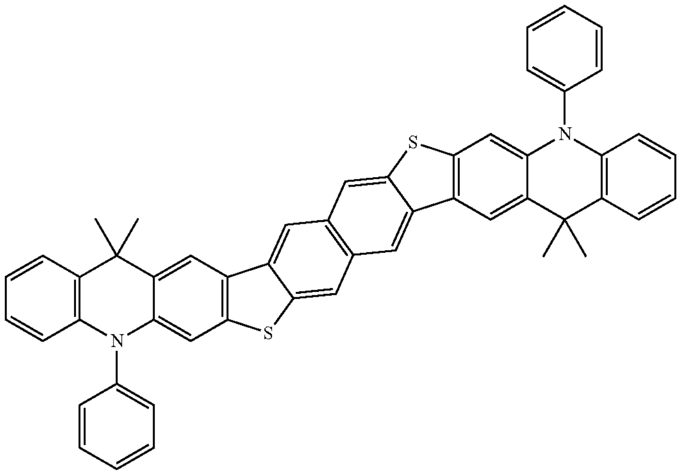
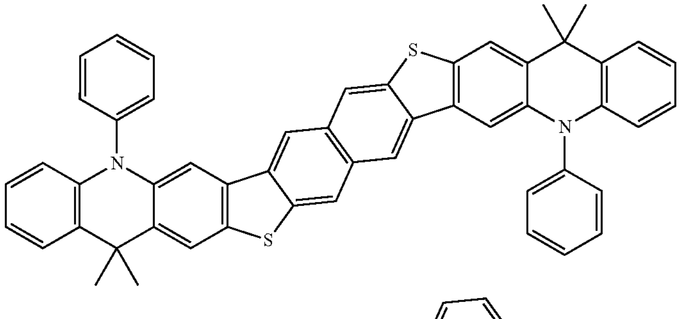
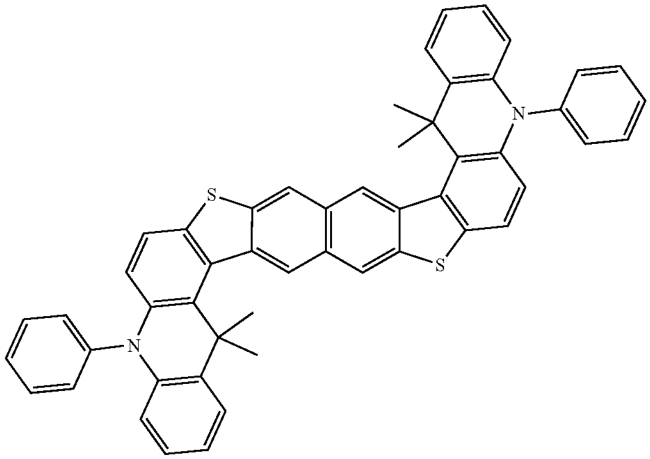

-continued
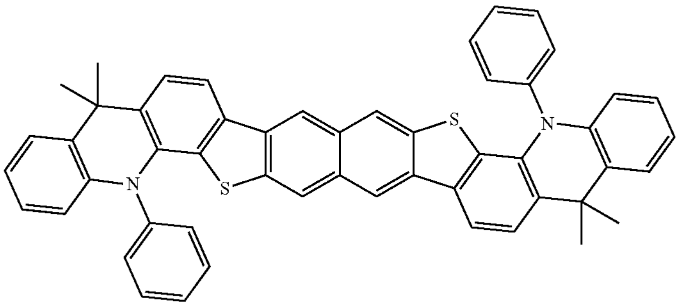
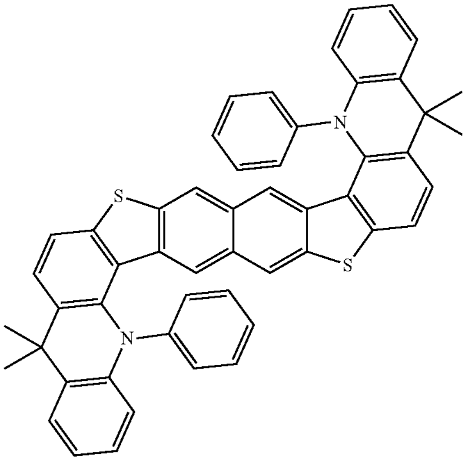
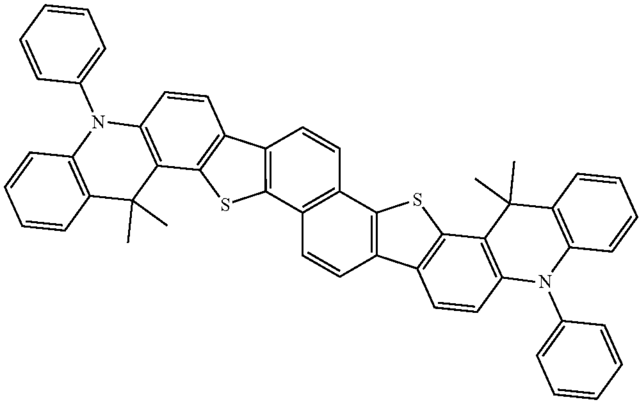
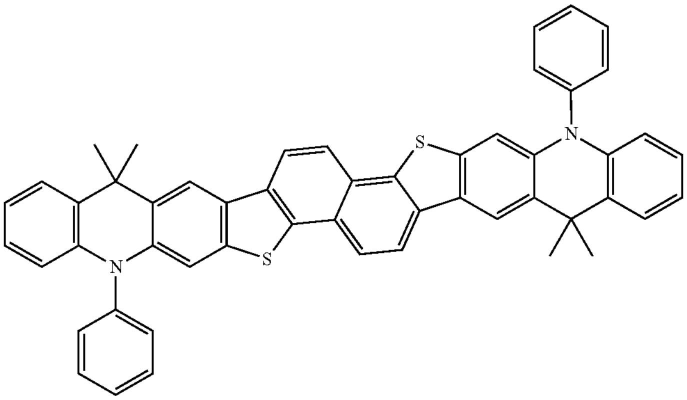

-continued
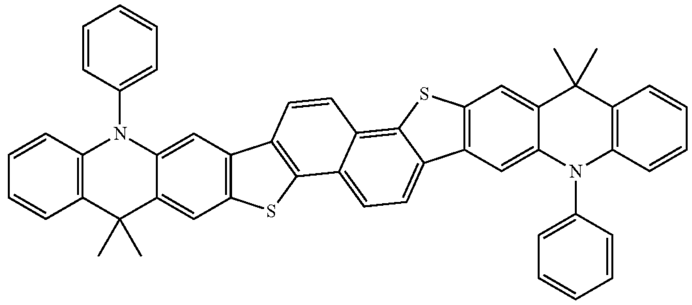
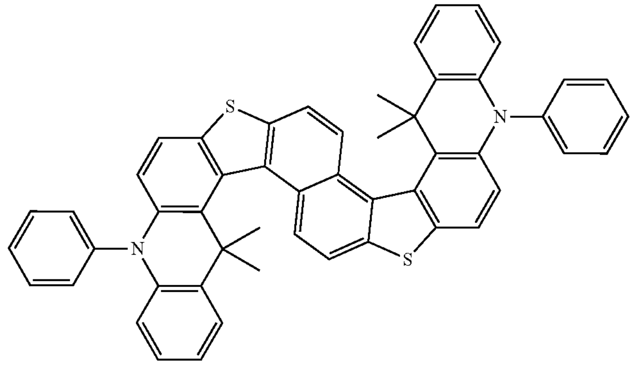
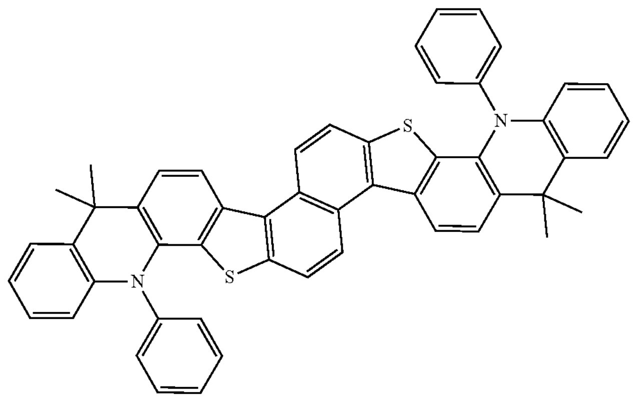
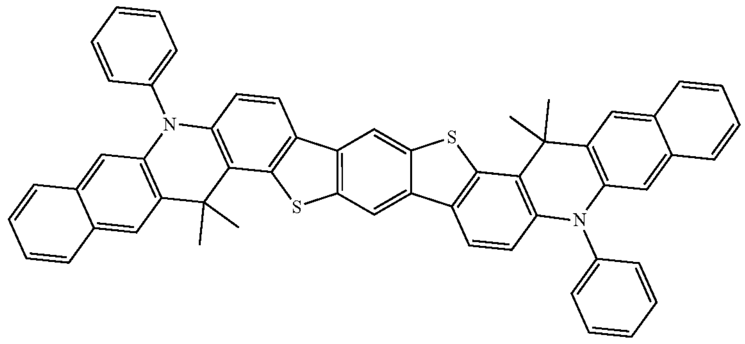

-continued
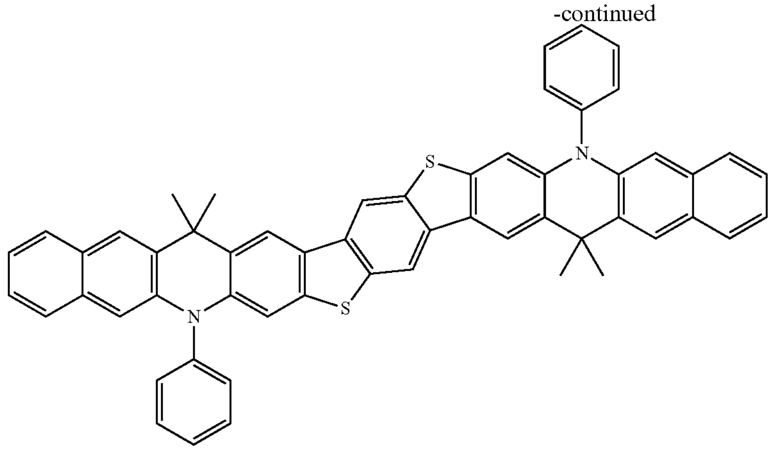
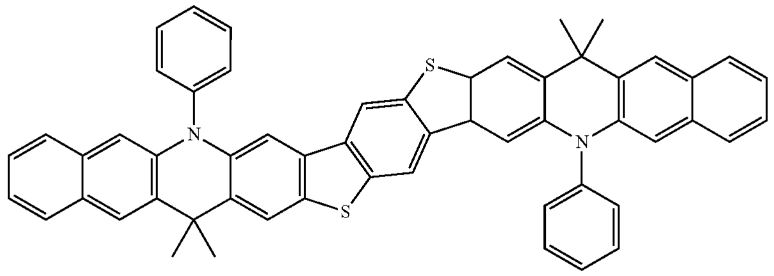
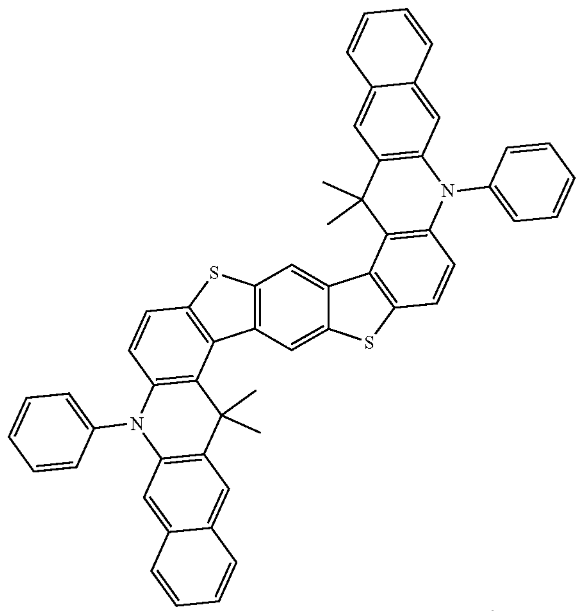
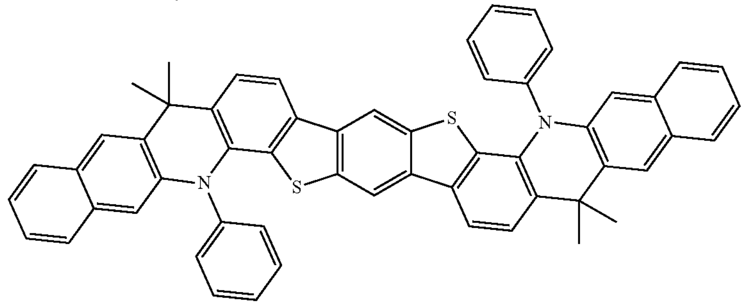

-continued
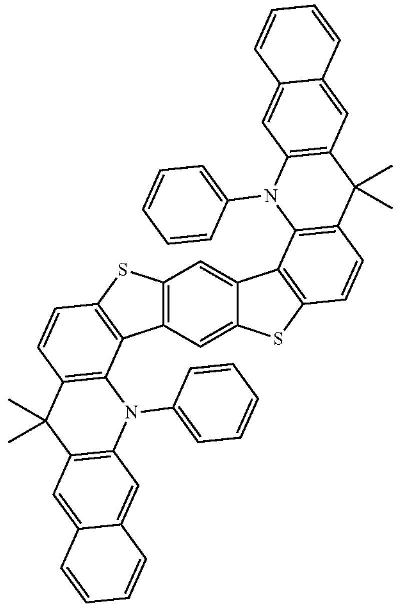
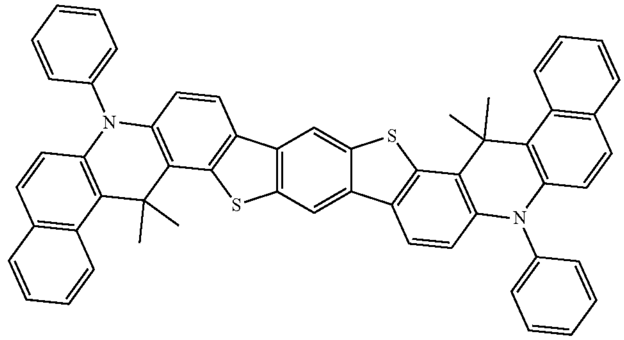
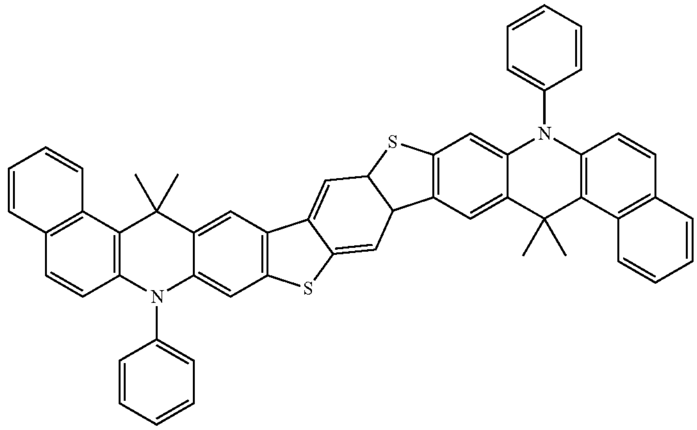
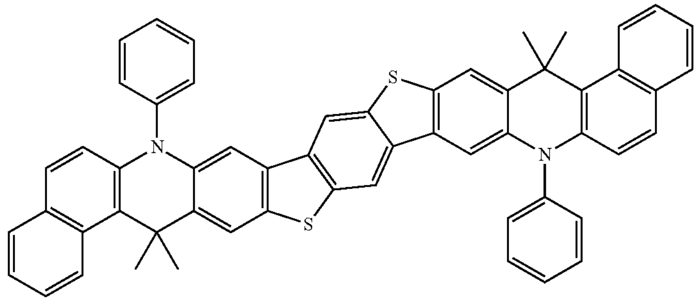

-continued
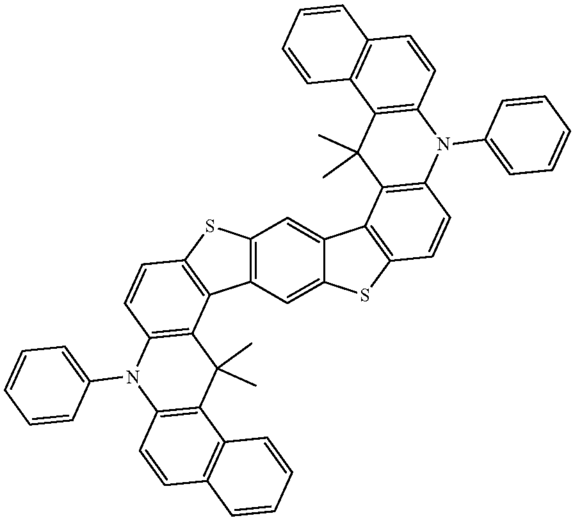
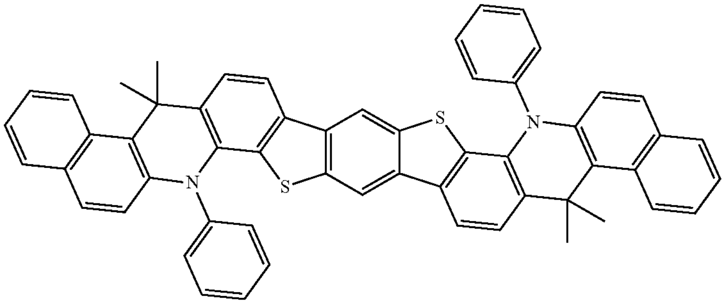
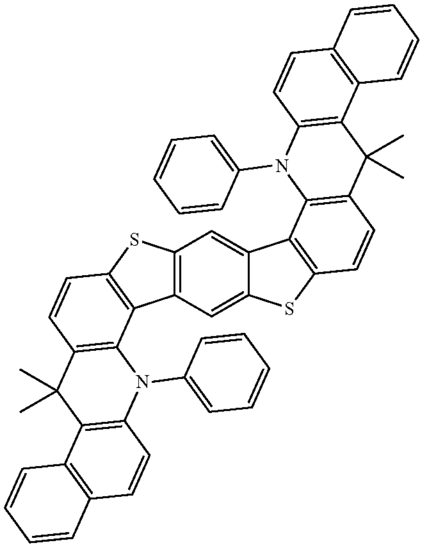
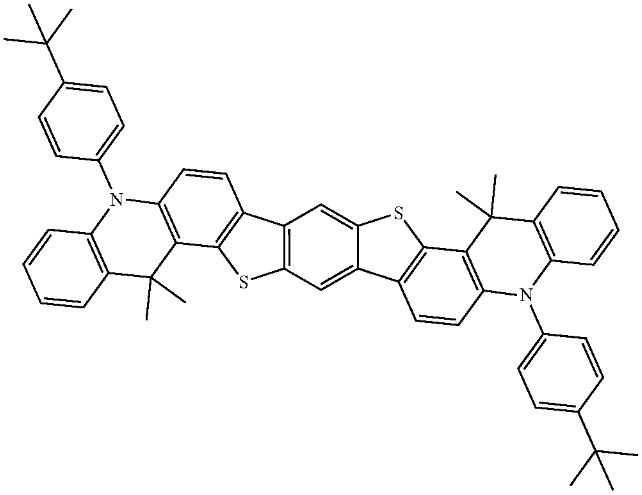

-continued
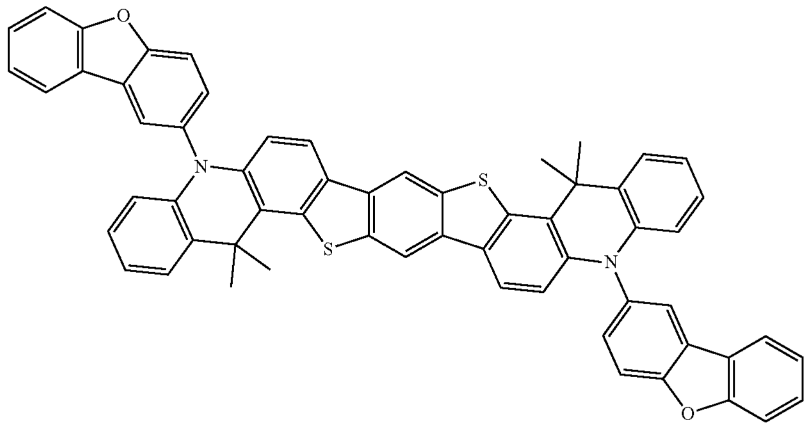
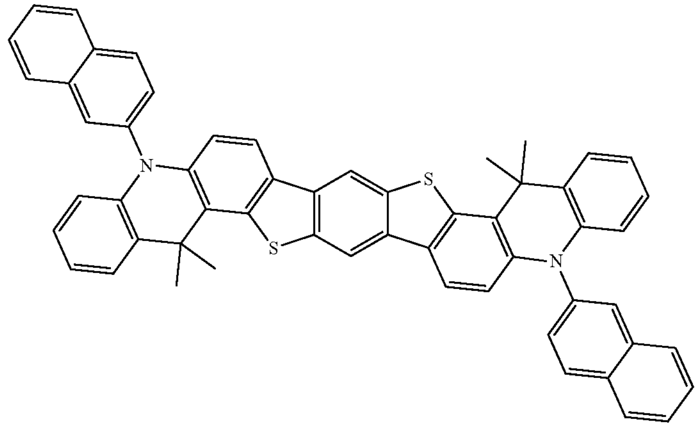
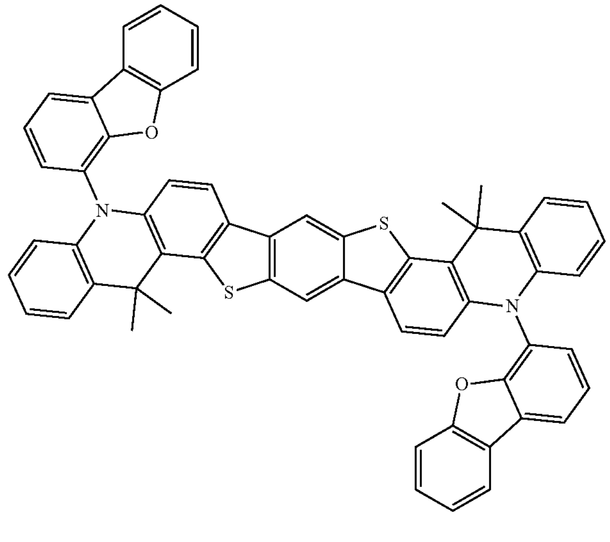

-continued

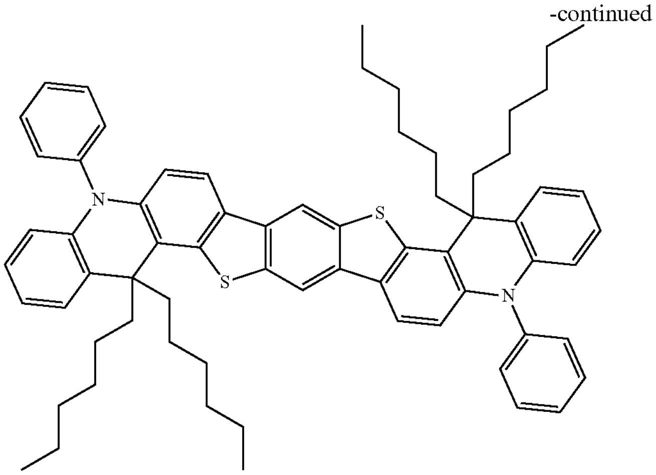

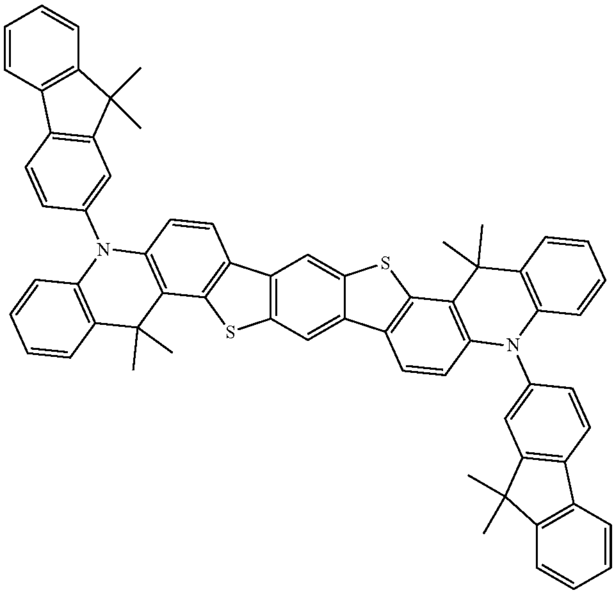

.

13. An organic light emitting device comprising: a first electrode; a second electrode that is provided opposite to the first electrode; and one or more organic material layers that are provided between the first electrode and the second electrode, wherein the one or more organic material layers include a layer comprising the compound of claim 1.

14. The organic light emitting device of claim 13, wherein:

the layer comprising the compound is a light emitting layer.

* * * * *